(12) United States Patent
Glezer

(10) Patent No.: US 11,434,525 B2
(45) Date of Patent: Sep. 6, 2022

(54) SPATIAL SEQUENCING

(71) Applicant: Singular Genomics Systems, Inc., La Jolla, CA (US)

(72) Inventor: Eli N. Glezer, Del Mar, CA (US)

(73) Assignee: SINGULAR GENOMICS SYSTEMS, INC., La Jolla, CA (US)

( * ) Notice: Subject to any disclaimer, the term of this patent is extended or adjusted under 35 U.S.C. 154(b) by 0 days.

(21) Appl. No.: 17/396,579

(22) Filed: Aug. 6, 2021

(65) Prior Publication Data
US 2022/0042084 A1    Feb. 10, 2022

Related U.S. Application Data

(60) Provisional application No. 63/209,903, filed on Jun. 11, 2021, provisional application No. 63/140,703, filed on Jan. 22, 2021, provisional application No. 63/062,047, filed on Aug. 6, 2020.

(51) Int. Cl.
| | | |
|---|---|---|
| C12Q 1/00 | (2006.01) | |
| C12Q 1/6869 | (2018.01) | |
| C12Q 1/6874 | (2018.01) | |
| C12Q 1/6841 | (2018.01) | |

(52) U.S. Cl.
CPC .................................. C12Q 1/6841 (2013.01)

(58) Field of Classification Search
None
See application file for complete search history.

(56) References Cited

U.S. PATENT DOCUMENTS

| | | | |
|---|---|---|---|
| 6,218,122 B1 | 4/2001 | Friend et al. | |
| 8,551,710 B2 | 10/2013 | Bernitz et al. | |
| 9,371,598 B2 | 6/2016 | Chee | |
| 9,556,473 B2 | 1/2017 | Bernitz et al. | |
| 9,593,365 B2 | 3/2017 | Frisen et al. | |
| 10,059,990 B2 | 8/2018 | Boyden et al. | |
| 10,138,509 B2 | 11/2018 | Church et al. | |
| 10,266,888 B2 | 4/2019 | Daugharthy et al. | |
| 10,323,272 B1 | 6/2019 | Rabbani et al. | |
| 10,495,554 B2 | 12/2019 | Deisseroth et al. | |
| 10,774,374 B2 | 9/2020 | Frisén et al. | |
| 2002/0064779 A1 | 5/2002 | Landegren et al. | |
| 2004/0137484 A1* | 7/2004 | Zhang ................... | C12Q 1/6834 435/6.16 |
| 2005/0287526 A1 | 12/2005 | Landegren et al. | |
| 2006/0292559 A1 | 12/2006 | Reddy et al. | |
| 2013/0296535 A1* | 11/2013 | Church ................... | G16B 20/00 530/387.1 |
| 2014/0170654 A1 | 6/2014 | Landegren et al. | |
| 2015/0225778 A1 | 8/2015 | Hindson et al. | |
| 2016/0116384 A1 | 4/2016 | Chen et al. | |
| 2016/0145696 A1 | 5/2016 | Brandon et al. | |
| 2016/0257993 A1 | 9/2016 | Fu et al. | |
| 2019/0017106 A1 | 1/2019 | Frisen et al. | |
| 2019/0055594 A1 | 2/2019 | Samusik et al. | |
| 2019/0113423 A1 | 4/2019 | Goodman et al. | |
| 2019/0119735 A1 | 4/2019 | Deisseroth et al. | |
| 2019/0161796 A1 | 5/2019 | Hauling et al. | |
| 2019/0241950 A1 | 8/2019 | Daugharthy et al. | |
| 2019/0264279 A1 | 8/2019 | Kain et al. | |
| 2019/0391140 A1 | 12/2019 | Aghvanyan et al. | |
| 2020/0071751 A1 | 3/2020 | Daugharthy et al. | |
| 2020/0224244 A1* | 7/2020 | Nilsson ................ | C12Q 1/6806 |
| 2020/0271556 A1 | 8/2020 | Sarkar et al. | |
| 2020/0277663 A1 | 9/2020 | Ramachandran Iyer et al. | |
| 2020/0277664 A1 | 9/2020 | Frenz | |
| 2021/0164029 A1 | 6/2021 | Sekedat et al. | |

FOREIGN PATENT DOCUMENTS

| | | |
|---|---|---|
| WO | WO-2018/091676 A1 | 5/2018 |
| WO | WO-2019/068880 A1 | 4/2019 |
| WO | WO-2019/199579 A1 | 10/2019 |
| WO | WO-2020/076976 A1 | 4/2020 |
| WO | WO-2020/076979 A1 | 4/2020 |
| WO | WO-2020/096687 A1 | 5/2020 |
| WO | WO-2020/099640 A1 | 5/2020 |

OTHER PUBLICATIONS

Mignardi et al. Fourth-generation sequencing in the cell and the clinic. Genome Medicine 2014, 6:31.*
Agrawal, S. et al. (Nov. 15, 2016). "Nivolumab dose selection: challenges, opportunities, and lessons learned for cancer immunotherapy," *J Immunotherapy Cancer* 4:72.
Alon, S.et al. (2020). "Expansion Sequencing: Spatially Precise In Situ Transcriptomics in Intact Biological Systems," *Biorxiv*, 2020, 2020.05.13.094268.
Arce, S. et al. (2013). "Fast and accurate automated cell boundary determination for fluorescence microscopy," *Sci Rep* 3:2266.
Bullinger, L. et al. (Apr. 15, 2004). "Use of gene-expression profiling to identify prognostic subclasses in adult acute myeloid leukemia," *N Engl J Med* 350(16):1605-1616.
Carow, B. et al. (2019). "Spatial and temporal localization of immune transcripts defines hallmarks and diversity in the tuberculosis granuloma," *Nature Comm.* 10(1):1823.
Carpenter, A. E. et al (2006, e-published Oct. 31, 2016). "CellProfiler: image analysis software for identifying and quantifying cell phenotypes," *Genome Biology* 7(10):R100.
Chen, F. et al. (Jan. 30, 2015, e-published Jan. 15, 2015). "Optical imaging. Expansion microscopy," *Science* 347(6221):543-548.
Chen, K. H. et al. (Apr. 24, 2015, e-published Apr. 9, 2015). "RNA imaging. Spatially resolved, highly multiplexed RNA profiling in single cells," *Science* 348(6233):aaa6090.
Christian, A.T. et al. (Dec. 4, 2001, e-published Nov. 27, 2001). "Detection of DNA point mutations and mRNA expression levels by rolling circle amplification in individual cells," *PNAS USA* 98(25):14238-14243.

(Continued)

*Primary Examiner* — Nianxiang Zou
(74) *Attorney, Agent, or Firm* — Mintz, Levin, Cohn, Ferris, Glovsky and Popeo, P.C.

(57) ABSTRACT

Disclosed herein, inter alia, are compositions and methods of use thereof for interrogating a sample comprising a cell.

28 Claims, 15 Drawing Sheets

Specification includes a Sequence Listing.

(56) References Cited

OTHER PUBLICATIONS

El-Sagheer, A. H. et al. (Aug. 21, 2012, e-published Mar. 22, 2012)."Click nucleic acid ligation: applications in biology and nanotechnology," *Accounts of chemical research* 45(8):1258-1267.
Gelali, E. et al. (Apr. 9, 2019). "iFISH is a publically available resource enabling versatile DNA FISH to study genome architecture," *Nat Commun* 10(1):1636.
Gore, A. et al. (Mar. 3, 2011). "Somatic coding mutations in human induced pluripotent stem cells," *Nature* 471(7336):63-67.
Gyllborg, D. et al. (Nov. 4, 2020). "Hybridization-based in situ sequencing (HybISS) for spatially resolved transcriptomics in human and mouse brain tissue," *Nucleic Acids Research* 48(19): e112.
Hagai, T. et al. (Nov. 2018, e-published Oct. 24, 2018). "Gene expression variability across cells and species shapes innate immunity," *Nature* 563(7730):197-202.
Heintzmann, R. et al. (Dec. 13, 2017, e-published Nov. 10, 2017). "Super-Resolution Structured Illumination Microscopy," *Chem. Rev.* 117(23):13890-13908.
Kappler, K. et al. (Aug. 2020, e-published Aug. 5, 2020). "Emergence and significance of carbohydrate-specific antibodies," *Genes Immun* 21(4):224-239.
Klein A.M. et al. (Jul. 25, 2017). "InDrops and Drop-seq technologies for single-cell sequencing," *Lab Chip* 17(15):2540-2541.
Lareau, C. A., et al. (Feb. 13, 2020). "Inference and effects of barcode multiplets in droplet-based single-cell assays," *Nature Communications* 11(1):866.
Larsson, C. et al., (May 2010, e-published Apr. 11, 2010). "In situ detection and genotyping of individual mRNA molecules," *Nat. Methods* 7(5):395-397.
Li, J. B. et al. (Sep. 2009, e-published Jun. 12, 2009). Multiplex padlock targeted sequencing reveals human hypermutable CpG variations, *Genome Res* 19(9):1606-1615.
Li, J. B. et al. (May 29, 2009). "Genome-wide identification of human RNA editing sites by parallel DNA capturing and sequencing," *Science* 324(5931):1210-1213.
Manuguerra I. et al. (May 1, 2018). "Gene assembly via one-pot chemical ligation of DNA promoted by DNA nanostructures," *Chem Commun (Camb)* 54(36):4529-4532.
Nilsson, M. et al. (Sep. 30, 1994). "Padlock probes: circularizing oligonucleotides for localized DNA detection," *Science* 265(5181):2085-2088.
Odeh, F., et al. (Dec. 18, 2019). "Aptamers Chemistry: Chemical Modifications and Conjugation Strategies," *Molecules* (Basel, Switzerland) 25(1):3.
Patel, A.P. et al. (Jun. 20, 2014, e-published Jun. 12, 2014). "Single-cell RNA-seq highlights intratumoral heterogeneity in primary glioblastoma," *Science* 344(6190):1396-1401.
Pearson, A. et al. (Aug. 2016, e-published May 13, 2016). "High-Level Clonal FGFR Amplification and Response to FGFR Inhibition in a Translational Clinical Trial," *Cancer Discov* 6(8):838-851.
Peters, J.M. et al. (Jan. 2011). "Multiparameter flow cytometry in the diagnosis and management of acute leukemia," *Arch Pathol Lab Med* 135(1):44-54.
Porreca, G. J. et al. (Nov. 2007, e-published Oct. 14, 2007). "Multiplex amplification of large sets of human exons," *Nat Methods* 4(11):931-936.
Sansone, A. (Jun. 2019). "Spatial transcriptomics levels up," *Nat Methods* 16(6):458.
Sapoznik, E. et al. (Nov. 12, 2020). "A versatile oblique plane microscope for large-scale and high-resolution imaging of subcellular dynamics," *eLife* 9:e57681.
Schlachter, S. et al. (2009). "A method to unmix multiple fluorophores in microscopy images with minimal a priori information," *Opt Express* 17(25):22747-22760.
Shirakawa, H. et al. (Mar. 2004). "Blind spectral decomposition of single-cell fluorescence by parallel factor analysis," *Biophysical Journal* 86(3):1739-1752.
Suzuki, A. et al. (Dec. 20, 2019). "Characterization of cancer omics and drug perturbations in panels of lung cancer cells," *Sci. Rep* 9(1):19529.
Van Der Velden, V.H.J. et al. (Jun. 2003). "Detection of minimal residual disease in hematologic malignancies by real-time quantitative PCR: principles, approaches, and laboratory aspects," *Leukemia* 17(6):1013-1034.
Vickovic, S.et al. (Oct. 2019, e-published Sep. 9, 2019). "High-definition spatial transcriptomics for in situ tissue profiling," *Nat. Methods* 16(10):987-990.
Wang X. et al. (Jul. 27, 2018, e-published Jun. 21, 2018). "Three-dimensional intact-tissue sequencing of single-cell transcriptional states," *Science* 361(6400):eaat5691.
Wang, G. et al. (Mar. 19, 2018). "Multiplexed imaging of high-density libraries of RNAs with MERFISH and expansion microscopy," *Sci Rep* 8(1):4847.
Wilson, C.S. et al. (Jul. 15, 2006, e-published Apr. 4, 2006). "Gene expression profiling of adult acute myeloid leukemia identifies novel biologic clusters for risk classification and outcome prediction," *Blood* 108(2):685-696.
York, A.G. et al. (Nov. 2013, e-published Oct. 6, 2013). "Instant super-resolution imaging in live cells and embryos via analog image processing," *Nature Methods* 10(11):1122-1126.
Zhang, K. et al. (Aug. 2009, e-published Jul. 20, 2009). "Digital RNA allelotyping reveals tissue-specific and allele-specific gene expression in human," *Nat Methods* 6(8):613-618.
Zheng, G. X. et al. (Jan. 16, 2017). "Massively parallel digital transcriptional profiling of single cells," *Nature Communications* 8:14049.
International Search Report dated Jan. 31, 2022 for PCT Application No. PCT/US2021/045105, filed Aug. 6, 2021, 7 pages.
Written Opinion dated Jan. 31, 2022 for PCT Application No. PCT/US2021/045105, filed Aug. 6, 2021, 11 pages.

\* cited by examiner

Target sequence

FIG. 9

| Drug Dose | Model AUC at Timepoint | | | | |
|---|---|---|---|---|---|
| | day 0 | 1 hr | 1 day | 10 days | 30 days |
| 0.1 mg/kg | 0.50 | 0.50 | 0.50 | 0.50 | 0.50 |
| 0.3 mg/kg | 0.50 | 0.50 | 0.50 | 0.52 | 0.50 |
| 1 mg/kg | 0.50 | 0.51 | 0.55 | 0.60 | 0.52 |
| 3 mg/kg | 0.50 | 0.53 | 0.62 | 0.81 | 0.56 |
| 10 mg/kg | 0.50 | 0.54 | 0.62 | 0.80 | 0.55 |

SEQUENCE LISTING

<160> NUMBER OF SEQ ID NOS: 9

<210> SEQ ID NO 1
<211> LENGTH: 13
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(13)

<400> SEQUENCE: 1
cgccgcggac acg                                                        13

<210> SEQ ID NO 2
<211> LENGTH: 9
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(9)

<400> SEQUENCE: 2 cgccgcgga                                                              9

<210> SEQ ID NO 3
<211> LENGTH: 17
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature

```
<222> LOCATION: (1)..(17)

<400> SEQUENCE: 3
cgccgcggac acggctg                                                  17

<210> SEQ ID NO 4
<211> LENGTH: 22
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(22)

<400> SEQUENCE: 4
cgccgcggac acggctgtgt at                                            22

<210> SEQ ID NO 5
<211> LENGTH: 30
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(30)

<400> SEQUENCE: 5
tgtattactg tgcgagagtt attactaggg                                    30

<210> SEQ ID NO 6
<211> LENGTH: 18
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(18)

<400> SEQUENCE: 6
gaggctgatt attactgc                                                 18

<210> SEQ ID NO 7
<211> LENGTH: 18
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(18)

<400> SEQUENCE: 7
gcggacacgg ctgtgtat                                                 18

<210> SEQ ID NO 8
<211> LENGTH: 11
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(11)

<400> SEQUENCE: 8
```

```
gacgtccata c                                                          11

<210> SEQ ID NO 9
<211> LENGTH: 14
<212> TYPE: DNA
<213> ORGANISM: Artificial Sequence
<220> FEATURE:
<223> OTHER INFORMATION: synthetic polynucleotide
<220> FEATURE:
<221> NAME/KEY: misc_feature
<222> LOCATION: (1)..(14)

<400> SEQUENCE: 9
gacgtccata ccgt                                                       14
```

SPATIAL SEQUENCING

CROSS-REFERENCES TO RELATED APPLICATIONS

This application claims the benefit of U.S. Provisional Application No. 63/062,047, filed Aug. 6, 2020; U.S. Provisional Application No. 63/140,703, filed Jan. 22, 2021; and U.S. Provisional Application No. 63/209,903, filed Jun. 11, 2021; each of which are incorporated herein by reference in their entirety and for all purposes.

SEQUENCE LISTING

The instant application contains a Sequence Listing which has been submitted electronically in ASCII format and is hereby incorporated by reference in its entirety. Said ASCII copy, created on Aug. 5, 2021, is named 051385-533001WO_ST25.txt and is 2,537 bytes in size.

BACKGROUND

Single-cell technologies have emerged to enable profiling the composition of the genome, epigenome, transcriptome, or proteome of a single cell. Uncovering the distribution, heterogeneity, spatial gene and protein co-expression patterns within cells and tissues is vital for understanding how cell co-localization influences tissue development and the spread of diseases such as cancer, which could lead to important new discoveries and therapeutics. Beyond quantifying gene and protein expression, obtaining precise sequencing information enables identification, monitoring, and possible treatment at the molecular level. Disclosed herein, inter alia, are solutions to these and other problems in the art.

BRIEF SUMMARY

In an aspect is provided a method of sequencing a plurality of target nucleic acids of a cell in situ. In embodiments, the method includes the following steps in situ for each of the plurality of target nucleic acids: i) hybridizing an oligonucleotide primer to the target nucleic acid, wherein the oligonucleotide primer includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region; ii) circularizing the oligonucleotide primer to generate a circular oligonucleotide, wherein circularizing includes extending the 3' end of the oligonucleotide primer along the target nucleic acid to generate a complementary sequence, and ligating the complementary sequence to the 5' end of the oligonucleotide primer; iii) amplifying the circular oligonucleotide by extending an amplification primer hybridized to the circular oligonucleotide with a strand-displacing polymerase, wherein the amplification primer extension generates an extension product including multiple complements of the circular oligonucleotide; and iv) sequencing the extension product of step (iii).

In an aspect is provided a method of sequencing an agent-mediated nucleic acid sequence of a cell, the method including administering a genetically modifying agent to the cell, and sequencing an agent-mediated nucleic acid sequence of the cell in situ according to the methods as described herein. In embodiments, the method includes the following steps in situ for each of the plurality of target nucleic acids: i) hybridizing an oligonucleotide primer to the target nucleic acid, wherein the oligonucleotide primer includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region; ii) circularizing the oligonucleotide primer to generate a circular oligonucleotide, wherein circularizing includes extending the 3' end of the oligonucleotide primer along the target nucleic acid to generate a complementary sequence, and ligating the complementary sequence to the 5' end of the oligonucleotide primer; iii) amplifying the circular oligonucleotide by extending an amplification primer hybridized to the circular oligonucleotide with a strand-displacing polymerase, wherein the amplification primer extension generates an extension product including multiple complements of the circular oligonucleotide; and iv) sequencing the extension product of step (iii).

In an aspect is provided a method of identifying a nucleic acid sequence as an agent-mediated nucleic acid sequence, the method including administering a genetically modifying agent to a cell, detecting whether an agent-mediated nucleic acid sequence is present in the cell by sequencing a plurality of target nucleic acids according to the methods as described herein, and identifying the nucleic acid sequence as an agent-mediated nucleic acid sequence when the presence of the agent-mediated nucleic acid is detected in the cell.

In an aspect is provided a method of identifying a cell that responds to a genetically modifying agent, the method including administering a genetically modifying agent to the cell, detecting whether an agent-mediated nucleic acid sequence is present in the cell by sequencing a plurality of target nucleic acids according to the methods as described herein, and identifying a cell that responds to a genetically modifying agent when the presence of the agent-mediated nucleic acid is detected in the cell.

In an aspect is provided a method of identifying an agent as a genetically modifying agent, the method including administering an agent to a cell, detecting whether an agent-mediated nucleic acid sequence is present in the cell by sequencing a plurality of target nucleic acids according to any of the methods as described herein, and identifying the genetically modifying agent when the presence of the agent-mediated nucleic acid is detected in the cell.

In an aspect is provided a polynucleotide including a plurality of units. In embodiments, each unit includes a portion of a genomic sequence and an oligonucleotide primer, wherein each oligonucleotide primer includes: a) a first region at a 3' end that is hybridized to a first complementary region of the polynucleotide, and b) a second region at a 5' end that is hybridized to a second complementary region of the polynucleotide, wherein the second complementary region is 5' with respect to the first complementary region.

BRIEF DESCRIPTION OF THE DRAWINGS

As shown in FIG. 1B, the oligonucleotide probe hybridizes to regions adjacent to (i.e., flanking) the target nucleic acid sequence, referred to as the first and the second complementary regions (depicted as white boxes). In the presence of a polymerase (e.g., a non-strand displacing polymerase), the complement to the target sequence is generated by extending from the first complementary region of the oligonucleotide primer, and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as depicted in FIG. 1D.

FIG. 3B shows two 16S rRNA genes wherein a plurality of circularized oligonucleotides generated according to the methods described herein overlap with variable and conserved regions. The degree of overlap can aid in alignment.

FIG. 4A depicts a plurality of circularized oligonucleotides being generated on the same target RNA molecule. FIG. 4B depicts sequencing the same region of interest utilizing a plurality of circularized oligonucleotide primers which target different sections of the region of interest. In this way, the entire region of interest may be copied, amplified, and sequenced. The probes are not bound to the same transcript simultaneously, but rather multiple transcripts containing the same region of interest. FIG. 4C depicts hybridizing two oligonucleotide primers to two distinct RNA molecules (referred to in FIG. 4C as RNA_1 and RNA_2) located in close proximity within a cell. Targeting two distinct targets provides spatial information about the colocalization efforts within a cell.

FIG. 9. Pharmacodynamic analysis of a T cell modulating immunotherapy using model performance as a Metric-of-Agent activity.

DETAILED DESCRIPTION

Figure 1A:
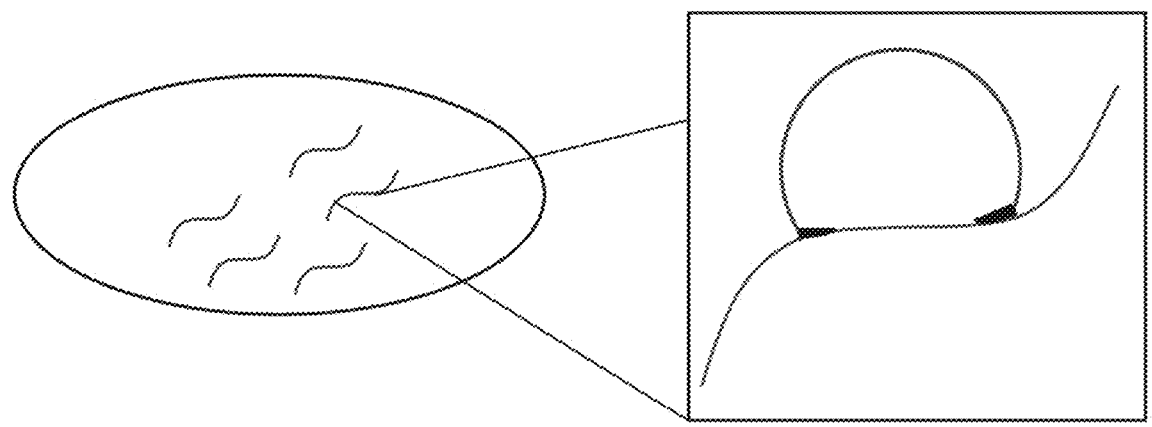
FIGS. 1A-1D. A cartoon depiction of a cell that is attached to a substrate surface (FIG. 1A) and fixed (e.g., using a fixing agent) and permeabilized according to known methods. The cell may have been cultured on the surface, or the cell may have been initially cultured in suspension and then fixed to the surface. The nucleic acid (e.g., mRNA, oncogene, or nucleic acid sequence of interest) present in the cell (depicted as a wavy line) is subjected to an amplification technique where a targeted oligonucleotide primer anneals to the nucleic acid of interest. The black wedges represent the first and second regions of the oligonucleotide primer that hybridize to the first and second complementary regions of the target nucleic acid.

The aspects and embodiments described herein relate to systems and methods for analyzing a cell and cellular components (e.g., RNA transcripts, proteins, or analytes). Data obtained from the proteome and transcriptome is used in research to gain insight into processes such as cellular differentiation, carcinogenesis, transcription regulation, and biomarker discovery, among others.

I. Definitions

The practice of the technology described herein will employ, unless indicated specifically to the contrary, conventional methods of chemistry, biochemistry, organic chemistry, molecular biology, bioinformatics, microbiology, recombinant DNA techniques, genetics, immunology, and cell biology that are within the skill of the art, many of which are described below for the purpose of illustration. Examples of such techniques are available in the literature. See, e.g., Singleton et al., DICTIONARY OF MICROBIOLOGY AND MOLECULAR BIOLOGY 2nd ed., J. Wiley & Sons (New York, N.Y. 1994); and Sambrook and Green, Molecular Cloning: A Laboratory Manual, 4th Edition (2012). Methods, devices, and materials similar or equivalent to those described herein can be used in the practice of embodiments of this invention.

All patents, patent applications, articles and publications mentioned herein, both supra and infra, are hereby expressly incorporated herein by reference in their entireties.

Unless defined otherwise herein, all technical and scientific terms used herein have the same meaning as commonly understood by one of ordinary skill in the art to which this disclosure belongs. Various scientific dictionaries that include the terms included herein are well known and available to those in the art. Although any methods and materials similar or equivalent to those described herein find use in the practice or testing of the disclosure, some preferred methods and materials are described. Accordingly, the terms defined immediately below are more fully described by reference to the specification as a whole. It is to be understood that this disclosure is not limited to the particular methodology, protocols, and reagents described, as these may vary, depending upon the context in which they are used by those of skill in the art. The following definitions are provided to facilitate understanding of certain terms used frequently herein and are not meant to limit the scope of the present disclosure.

As used herein, the singular terms "a", "an", and "the" include the plural reference unless the context clearly indicates otherwise. Reference throughout this specification to, for example, "one embodiment", "an embodiment", "another embodiment", "a particular embodiment", "a related embodiment", "a certain embodiment", "an additional embodiment", or "a further embodiment" or combinations thereof means that a particular feature, structure or characteristic described in connection with the embodiment is included in at least one embodiment of the present disclosure. Thus, the appearances of the foregoing phrases in various places throughout this specification are not necessarily all referring to the same embodiment. Furthermore, the particular features, structures, or characteristics may be combined in any suitable manner in one or more embodiments.

As used herein, the term "about" means a range of values including the specified value, which a person of ordinary skill in the art would consider reasonably similar to the specified value. In embodiments, the term "about" means within a standard deviation using measurements generally acceptable in the art. In embodiments, about means a range extending to +/−10% of the specified value. In embodiments, about means the specified value.

Throughout this specification, unless the context requires otherwise, the words "comprise", "comprises" and "comprising" will be understood to imply the inclusion of a stated step or element or group of steps or elements but not the exclusion of any other step or element or group of steps or elements. By "consisting of" is meant including, and limited to, whatever follows the phrase "consisting of" Thus, the phrase "consisting of" indicates that the listed elements are required or mandatory, and that no other elements may be present. By "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that no other elements are optional and may or may not be present depending upon whether or not they affect the activity or action of the listed elements.

As used herein, the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are "tethered", "coated", "attached", or "immobilized" to one another or to a common solid or semisolid support. An association may refer to a relationship, or connection, between two entities. Associated may refer to the relationship between a sample and the DNA molecules, RNA molecules, or polynucleotides originating from or derived from that sample. These relationships may be encoded in oligonucleotide barcodes, as described herein. A polynucleotide is associated with a sample if it is an endogenous polynucleotide, i.e., it occurs in the sample at the time the sample is obtained, or is derived from an endogenous polynucleotide. For example, the RNAs endogenous to a cell are associated with that cell. cDNAs resulting from reverse transcription of these RNAs, and DNA amplicons resulting from PCR amplification of the cDNAs, contain the sequences of the RNAs and are also associated with the cell. The polynucleotides associated with a sample need not be located or synthesized in the sample, and are considered associated with the sample even after the sample has been destroyed (for example, after a cell has been lysed). Barcoding can be used to determine which polynucleotides in a mixture are associated with a particular sample.

As used herein, the term "complementary" or "substantially complementary" refers to the hybridization, base pairing, or the formation of a duplex between nucleotides or nucleic acids. For example, complementarity exists between the two strands of a double stranded DNA molecule or between an oligonucleotide primer and a primer binding site on a single stranded nucleic acid when a nucleotide (e.g., RNA or DNA) or a sequence of nucleotides is capable of base pairing with a respective cognate nucleotide or cognate sequence of nucleotides. As described herein and commonly known in the art the complementary (matching) nucleotide of adenosine (A) is thymidine (T) and the complementary (matching) nucleotide of guanosine (G) is cytosine (C). Thus, a complement may include a sequence of nucleotides that base pair with corresponding complementary nucleotides of a second nucleic acid sequence. The nucleotides of a complement may partially or completely match the nucleotides of the second nucleic acid sequence. Where the nucleotides of the complement completely match each nucleotide of the second nucleic acid sequence, the complement forms base pairs with each nucleotide of the second nucleic acid sequence. Where the nucleotides of the complement partially match the nucleotides of the second nucleic acid sequence only some of the nucleotides of the complement form base pairs with nucleotides of the second nucleic acid sequence. Examples of complementary sequences include coding and non-coding sequences, wherein the non-coding sequence contains complementary nucleotides to the coding sequence and thus forms the complement of the coding sequence. A further example of complementary sequences are sense and antisense sequences, wherein the sense sequence contains complementary nucleotides to the antisense sequence and thus forms the complement of the antisense sequence. "Duplex" means at least two oligonucleotides and/or polynucleotides that are fully or partially complementary undergo Watson-Crick type base pairing among all or most of their nucleotides so that a stable complex is formed.

As described herein, the complementarity of sequences may be partial, in which only some of the nucleic acids match according to base pairing, or complete, where all the nucleic acids match according to base pairing. Thus, two sequences that are complementary to each other, may have a specified percentage of nucleotides that complement one another (e.g., about 60%, preferably 65%, 70%, 75%, 80%, 85%, 90%, 91%, 92%, 93%, 94%, 95%, 96%, 97%, 98%, 99%, or higher complementarity over a specified region). In embodiments, two sequences are complementary when they are completely complementary, having 100% complementarity. In embodiments, sequences in a pair of complementary sequences form portions of a single polynucleotide with non-base-pairing nucleotides (e.g., as in a hairpin structure, with or without an overhang) or portions of separate polynucleotides. In embodiments, one or both sequences in a pair of complementary sequences form portions of longer polynucleotides, which may or may not include additional regions of complementarity.

As used herein, the term "contacting" is used in accordance with its plain ordinary meaning and refers to the process of allowing at least two distinct species (e.g., chemical compounds, biomolecules, nucleotides, binding reagents, or cells) to become sufficiently proximal to react, interact or physically touch. However, the resulting reaction product can be produced directly from a reaction between the added reagents or from an intermediate from one or more of the added reagents that can be produced in the reaction mixture. The term "contacting" may include allowing two species to react, interact, or physically touch, wherein the two species may be a compound, a protein (e.g., an antibody), or enzyme.

As used herein, the term "hybridize" or "specifically hybridize" refers to a process where two complementary nucleic acid strands anneal to each other under appropriately stringent conditions. Hybridizations are typically and preferably conducted with oligonucleotides. The terms "annealing" and "hybridization" are used interchangeably to mean the formation of a stable duplex. Non-limiting examples of nucleic acid hybridization techniques are described in, for example, Sambrook, et al., Molecular Cloning: A Laboratory Manual (2nd Edition, 1989). Those skilled in the art understand how to estimate and adjust the stringency of hybridization conditions such that sequences having at least a desired level of complementarity will stably hybridize, while those having lower complementarity will not. As used herein, the term "stringent condition" refers to condition(s) under which a polynucleotide probe or primer will hybridize preferentially to its target sequence, and to a lesser extent to, or not at all to, other sequences. A "stringent hybridization" and "stringent hybridization wash conditions" in the context of nucleic acid hybridization are sequence dependent, and are different under different environmental parameters.

As used herein, the term "nucleic acid" refers to nucleotides (e.g., deoxyribonucleotides or ribonucleotides) and polymers thereof in either single-, double- or multiple-stranded form, or complements thereof. The terms "polynucleotide," "oligonucleotide," "oligo" or the like refer, in the usual and customary sense, to a sequence of nucleotides. The term "nucleotide" refers, in the usual and customary sense, to a single unit of a polynucleotide, i.e., a monomer.

Nucleotides can be ribonucleotides, deoxyribonucleotides, or modified versions thereof. Examples of polynucleotides contemplated herein include single and double stranded DNA, single and double stranded RNA, and hybrid molecules having mixtures of single and double stranded DNA and RNA with linear or circular framework. Non-limiting examples of polynucleotides include a gene, a gene fragment, an exon, an intron, intergenic DNA (including, without limitation, heterochromatic DNA), messenger RNA (mRNA), transfer RNA, ribosomal RNA, a ribozyme, cDNA, a recombinant polynucleotide, a branched polynucleotide, a plasmid, a vector, isolated DNA of a sequence, isolated RNA of a sequence, a nucleic acid probe, and a primer. Polynucleotides useful in the methods of the disclosure may comprise natural nucleic acid sequences and variants thereof, artificial nucleic acid sequences, or a combination of such sequences. Nucleic acids can be linear or branched. For example, nucleic acids can be a linear chain of nucleotides or the nucleic acids can be branched, e.g., such that the nucleic acids comprise one or more arms or branches of nucleotides. Optionally, the branched nucleic acids are repetitively branched to form higher ordered structures such as dendrimers and the like.

As used herein, the terms "polynucleotide primer" and "primer" refer to any polynucleotide molecule that may hybridize to a polynucleotide template, be bound by a polymerase, and be extended in a template-directed process for nucleic acid synthesis. The primer may be a separate polynucleotide from the polynucleotide template, or both may be portions of the same polynucleotide (e.g., as in a hairpin structure having a 3' end that is extended along another portion of the polynucleotide to extend a double-stranded portion of the hairpin. A primer can be of any length depending on the particular technique it will be used for. For example, amplification primers are generally between 10 and 40 nucleotides in length. The length and complexity of the primer onto the nucleic acid template may vary. One of skill can adjust these factors to provide optimum hybridization and signal production for a given hybridization procedure. The primer permits the addition of a nucleotide residue thereto, or oligonucleotide or polynucleotide synthesis therefrom, under suitable conditions. In an embodiment the primer is a DNA primer, i.e., a primer consisting of, or largely consisting of, deoxyribonucleotide residues. The primers are designed to have a sequence that is the complement of a region of template polynucleotide (e.g., a padlock probe) to which the primer hybridizes. The addition of a nucleotide residue to the 3' end of a primer by formation of a phosphodiester bond results in an extension product. The addition of a nucleotide residue to the 3' end of the extension product by formation of a phosphodiester bond results in a further extension product. In another embodiment the primer is an RNA primer. In embodiments, a primer is hybridized to a target polynucleotide. A "primer" is complementary to a polynucleotide template, and complexes by hydrogen bonding or hybridization with the template to give a primer/template complex for initiation of synthesis by a polymerase, which is extended by the addition of covalently bonded bases linked at its 3' end complementary to the template in the process of DNA synthesis. A primer typically has a length of 10 to 50 nucleotides. For example, a primer may have a length of 10 to 40, 10 to 30, 10 to 20, 25 to 50, 15 to 40, 15 to 30, 20 to 50, 20 to 40, or 20 to 30 nucleotides. In some embodiments, a primer has a length of 18 to 24 nucleotides. Examples of primers include, but are not limited to, P5 primer, P7 primer, PE1 primer, PE2 primer, A19 primer, or others known in the art.

Nucleic acids, including e.g., nucleic acids with a phosphorothioate backbone, can include one or more reactive moieties. As used herein, the term reactive moiety includes any group capable of reacting with another molecule, e.g., a nucleic acid or polypeptide through covalent, non-covalent or other interactions. By way of example, the nucleic acid can include an amino acid reactive moiety that reacts with an amino acid on a protein or polypeptide through a covalent, non-covalent or other interaction.

The term "messenger RNA" or "mRNA" refers to an RNA that is without introns and is capable of being translated into a polypeptide. The term "RNA" refers to any ribonucleic acid, including but not limited to mRNA, tRNA (transfer RNA), rRNA (ribosomal RNA), and/or noncoding RNA (such as lncRNA (long noncoding RNA)). The term "cDNA" refers to a DNA that is complementary or identical to an RNA, in either single stranded or double stranded form.

As used herein, the term "template polynucleotide" refers to any polynucleotide molecule that may be bound by a polymerase and utilized as a template for nucleic acid synthesis. A template polynucleotide may be a target polynucleotide. In general, the term "target polynucleotide" refers to a nucleic acid molecule or polynucleotide in a starting population of nucleic acid molecules having a target sequence whose presence, amount, and/or nucleotide sequence, or changes in one or more of these, are desired to be determined. In general, the term "target sequence" refers to a nucleic acid sequence on a single strand of nucleic acid. The target sequence may be a portion of a gene, a regulatory sequence, genomic DNA, cDNA, RNA including mRNA, microRNA (miRNA), rRNA, or others. The target sequence may be a target sequence from a sample or a secondary target such as a product of an amplification reaction. A target polynucleotide is not necessarily any single molecule or sequence. For example, a target polynucleotide may be any one of a plurality of target polynucleotides in a reaction, or all polynucleotides in a given reaction, depending on the reaction conditions. For example, in a nucleic acid amplification reaction with random primers, all polynucleotides in a reaction may be amplified. As a further example, a collection of targets may be simultaneously assayed using polynucleotide primers directed to a plurality of targets in a single reaction. As yet another example, all or a subset of polynucleotides in a sample may be modified by the addition of a primer-binding sequence (such as by the ligation of adapters containing the primer binding sequence), rendering each modified polynucleotide a target polynucleotide in a reaction with the corresponding primer polynucleotide(s).

A polynucleotide is typically composed of a specific sequence of four nucleotide bases: adenine (A); cytosine (C); guanine (G); and thymine (T) (uracil (U) for thymine (T) when the polynucleotide is RNA). Thus, the term "polynucleotide sequence" is the alphabetical representation of a polynucleotide molecule; alternatively, the term may be applied to the polynucleotide molecule itself. This alphabetical representation can be input into databases in a computer having a central processing unit and used for bioinformatics applications such as functional genomics and homology searching. Polynucleotides may optionally include one or more non-standard nucleotide(s), nucleotide analog(s) and/or modified nucleotides.

As used herein, the terms "analog" or "analogue", in reference to a chemical compound (e.g., a nucleotide), refers to compound having a structure similar to that of another one, but differing from it in respect of one or more different atoms, functional groups, or substructures that are replaced with one or more other atoms, functional groups, or substructures. In the context of a nucleotide useful in practicing embodiments of the invention, a nucleotide analog refers to a compound that, like the nucleotide of which it is an analog, can be incorporated into a nucleic acid molecule (e.g., an extension product) by a suitable polymerase, for example, a DNA polymerase in the context of a dNTP analogue. The terms also encompass nucleic acids containing known nucleotide analogs or modified backbone residues or linkages, which are synthetic, naturally occurring, and non-naturally occurring, which have similar binding properties as the reference nucleic acid, and which are metabolized in a manner similar to the reference nucleotides. Examples of such analogs include, include, without limitation, phosphodiester derivatives including, e.g., phosphoramidate, phosphorodiamidate, phosphorothioate (also known as phosphothioate having double bonded sulfur replacing oxygen in the phosphate), phosphorodithioate, phosphonocarboxylic acids, phosphonocarboxylates, phosphonoacetic acid, phosphonoformic acid, methyl phosphonate, boron phosphonate, or O-methylphosphoroamidite linkages (see, e.g., see Eckstein, OLIGONUCLEOTIDES AND ANALOGUES: A PRACTICAL APPROACH, Oxford University Press) as well as modifications to the nucleotide bases such as in 5-methyl cytidine or pseudouridine; and peptide nucleic acid backbones and linkages. Other analog nucleic acids include those with positive backbones; non-ionic backbones, modified sugars, and non-ribose backbones (e.g. phosphorodiamidate morpholino oligos or locked nucleic acids (LNA) as known in the art), including those described in U.S. Pat. Nos. 5,235,033 and 5,034,506, and Chapters 6 and 7, ASC Symposium Series 580, CARBOHYDRATE MODIFICATIONS IN ANTISENSE RESEARCH, Sanghui & Cook, eds. Nucleic acids containing one or more carbocyclic sugars are also included within one definition of nucleic acids. Modifications of the ribose-phosphate backbone may be done for a variety of reasons, e.g., to increase the stability and half-life of such molecules in physiological environments or as probes on a biochip. Mixtures of naturally occurring nucleic acids and analogs can be made; alternatively, mixtures of different nucleic acid analogs, and mixtures of naturally occurring nucleic acids and analogs may be made. In embodiments, the internucleotide linkages in DNA are phosphodiester, phosphodiester derivatives, or a combination of both.

As used herein, the term "modified nucleotide" refers to nucleotide modified in some manner. Typically, a nucleotide contains a single 5-carbon sugar moiety, a single nitrogenous base moiety and 1 to three phosphate moieties. In embodiments, a nucleotide can include a blocking moiety (i.e., a reversible terminator) or a label moiety (e.g., a label is attached to the modified nucleotide through a cleavable linker). A blocking moiety on a nucleotide prevents formation of a covalent bond between the 3' hydroxyl moiety of the nucleotide and the 5' phosphate of another nucleotide. A blocking moiety on a nucleotide can be reversible, whereby the blocking moiety can be removed or modified to allow the 3' hydroxyl to form a covalent bond with the 5' phosphate of another nucleotide. A blocking moiety can be effectively irreversible under particular conditions used in a method set forth herein. In embodiments, the blocking moiety is attached to the 3' oxygen of the nucleotide and is independently —NH$_2$, —CN, —CH$_3$, C$_2$-C$_6$ allyl (e.g., —CH$_2$—CH=CH$_2$), methoxyalkyl (e.g., —CH$_2$—O—CH$_3$), or —CH$_2$N$_3$. In embodiments, the blocking moiety is attached to the 3' oxygen of the nucleotide and is independently

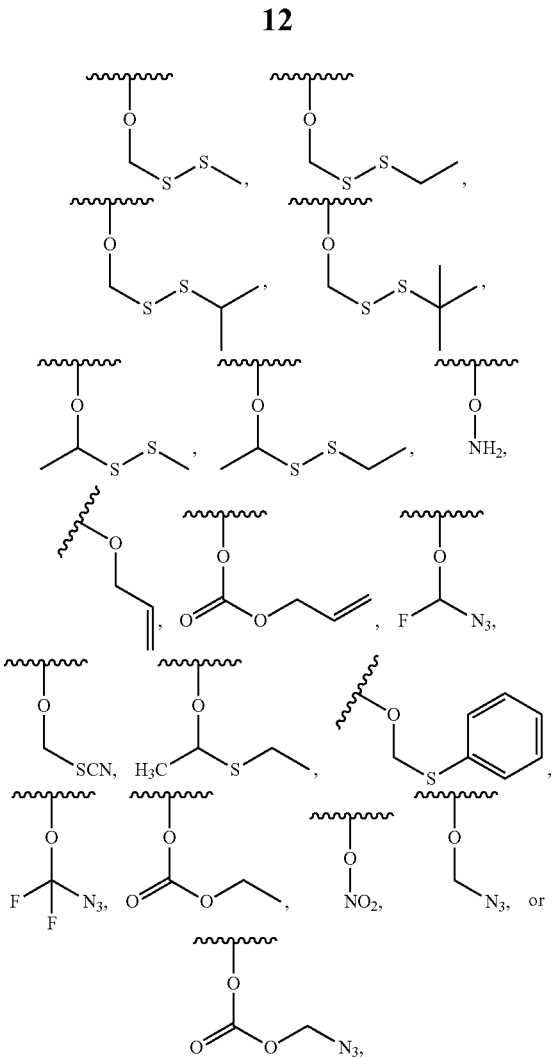

wherein the 3' oxygen of the nucleotide is explicitly shown in the formulae above. A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. Examples of nucleotide analogues include, without limitation, 7-deaza-adenine, 7-deaza-guanine, the analogues of deoxynucleotides shown herein, analogues in which a label is attached through a cleavable linker to the 5-position of cytosine or thymine or to the 7-position of deaza-adenine or deaza-guanine, and analogues in which a small chemical moiety is used to cap the OH group at the 3'-position of deoxyribose. Nucleotide analogues and DNA polymerase-based DNA sequencing are also described in U.S. Pat. No. 6,664,079, which is incorporated herein by reference in its entirety for all purposes.

The term "cleavable linker" or "cleavable moiety" as used herein refers to a divalent or monovalent, respectively, moiety which is capable of being separated (e.g., detached, split, disconnected, hydrolyzed, a stable bond within the moiety is broken) into distinct entities. A cleavable linker is cleavable (e.g., specifically cleavable) in response to external stimuli (e.g., enzymes, nucleophilic/basic reagents, reducing agents, photo-irradiation, electrophilic/acidic reagents, organometallic and metal reagents, or oxidizing reagents). A chemically cleavable linker refers to a linker which is capable of being split in response to the presence of a chemical (e.g., acid, base, oxidizing agent, reducing agent, Pd(0), tris-(2-carboxyethyl)phosphine, dilute nitrous acid, fluoride, tris(3-hydroxypropyl)phosphine), sodium dithionite ($Na_2S_2O_4$), or hydrazine ($N_2H_4$)). A chemically cleavable linker is non-enzymatically cleavable. In embodiments, the cleavable linker is cleaved by contacting the cleavable linker with a cleaving agent. In embodiments, the cleaving agent is a phosphine containing reagent (e.g., TCEP or THPP), sodium dithionite ($Na_2S_2O_4$), weak acid, hydrazine ($N_2H_4$), Pd(0), or light-irradiation (e.g., ultraviolet radiation). In embodiments, cleaving includes removing. A "cleavable site" or "scissile linkage" in the context of a polynucleotide is a site which allows controlled cleavage of the polynucleotide strand (e.g., the linker, the primer, or the polynucleotide) by chemical, enzymatic, or photochemical means known in the art and described herein. A scissile site may refer to the linkage of a nucleotide between two other nucleotides in a nucleotide strand (i.e., an internucleosidic linkage). In embodiments, the scissile linkage can be located at any position within the one or more nucleic acid molecules, including at or near a terminal end (e.g., the 3' end of an oligonucleotide) or in an interior portion of the one or more nucleic acid molecules. In embodiments, conditions suitable for separating a scissile linkage include modulating the pH and/or the temperature. In embodiments, a scissile site can include at least one acid-labile linkage. For example, an acid-labile linkage may include a phosphoramidate linkage. In embodiments, a phosphoramidate linkage can be hydrolysable under acidic conditions, including mild acidic conditions such as trifluoroacetic acid and a suitable temperature (e.g., 30° C.), or other conditions known in the art, for example Matthias Mag, et al Tetrahedron Letters, Volume 33, Issue 48, 1992, 7319-7322. In embodiments, the scissile site can include at least one photolabile internucleosidic linkage (e.g., o-nitrobenzyl linkages, as described in Walker et al, J. Am. Chem. Soc. 1988, 110, 21, 7170-7177), such as o-nitrobenzyloxymethyl or p-nitrobenzyloxymethyl group(s). In embodiments, the scissile site includes at least one uracil nucleobase. In embodiments, a uracil nucleobase can be cleaved with a uracil DNA glycosylase (UDG) or Formamidopyrimidine DNA Glycosylase Fpg. In embodiments, the scissile linkage site includes a sequence-specific nicking site having a nucleotide sequence that is recognized and nicked by a nicking endonuclease enzyme or a uracil DNA glycosylase.

As used herein, the terms "reversible blocking groups" and "reversible terminators" are used in accordance with their plain and ordinary meanings and refer to a blocking moiety located, for example, at the 3' position of the nucleotide and may be a chemically cleavable moiety such as an allyl group, an azidomethyl group or a methoxymethyl group, or may be an enzymatically cleavable group such as a phosphate ester. Non-limiting examples of nucleotide blocking moieties are described in applications WO 2004/018497, U.S. Pat. Nos. 7,057,026, 7,541,444, WO 96/07669, U.S. Pat. Nos. 5,763,594, 5,808,045, 5,872,244 and 6,232,465 the contents of which are incorporated herein by reference in their entirety. The nucleotides may be labelled or unlabeled. They may be modified with reversible terminators useful in methods provided herein and may be 3'-O-blocked reversible or 3'-unblocked reversible terminators. In nucleotides with 3'-O-blocked reversible terminators, the blocking group —OR [reversible terminating (capping) group] is linked to the oxygen atom of the 3'-OH of the pentose, while the label is linked to the base, which acts as a reporter and can be cleaved. The 3'-O-blocked reversible terminators are known in the art, and may be, for instance, a 3'-$ONH_2$ reversible terminator, a 3'-O-allyl reversible terminator, or a 3'-O-azidomethyl reversible terminator. In embodiments, the reversible terminator moiety is attached to the 3'-oxygen of the nucleotide, having the formula:

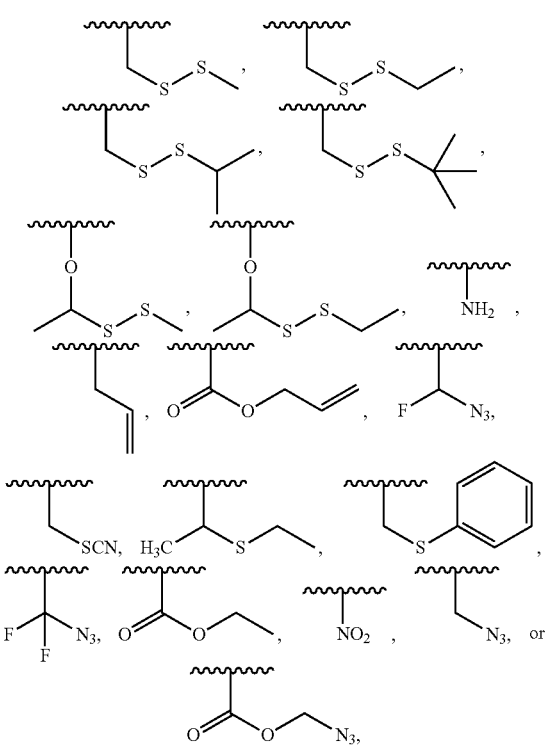

wherein the 3' oxygen of the nucleotide is not shown in the formulae above. The term "allyl" as described herein refers to an unsubstituted methylene attached to a vinyl group (i.e., —CH=$CH_2$). In embodiments, the reversible terminator moiety is

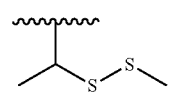 [SMILES: *C(C)SSC]

as described in U.S. Pat. No. 10,738,072, which is incorporated herein by reference for all purposes. For example, a nucleotide including a reversible terminator moiety may be represented by the formula:

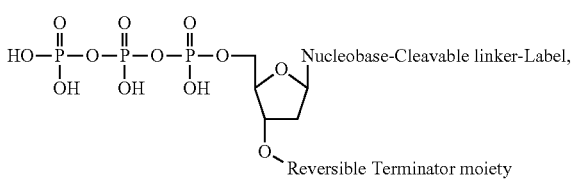

where the nucleobase is adenine or adenine analogue, thymine or thymine analogue, guanine or guanine analogue, or cytosine or cytosine analogue.

A label moiety of a nucleotide can be any moiety that allows the nucleotide to be detected, for example, using a spectroscopic method. Exemplary label moieties are fluorescent labels, mass labels, chemiluminescent labels, electrochemical labels, detectable labels and the like. One or more of the above moieties can be absent from a nucleotide used in the methods and compositions set forth herein. For example, a nucleotide can lack a label moiety or a blocking moiety or both. As used herein, the term "label" or "labels" generally refer to molecules that can directly or indirectly produce or result in a detectable signal either by themselves or upon interaction with another molecule. Non-limiting examples of detectable labels include labels comprising fluorescent dyes, biotin, digoxin, haptens, and epitopes. In general, a dye is a molecule, compound, or substance that can provide an optically detectable signal, such as a colorimetric, luminescent, bioluminescent, chemiluminescent, phosphorescent, or fluorescent signal. In embodiments, the dye is a fluorescent dye. Non-limiting examples of dyes, some of which are commercially available, include CF dyes (Biotium, Inc.), Alexa Fluor dyes (Thermo Fisher), DyLight dyes (Thermo Fisher), Cy dyes (GE Healthscience), IRDyes (Li-Cor Biosciences, Inc.), and HiLyte dyes (Anaspec, Inc.). In embodiments, the label is a fluorophore.

Examples of detectable agents (i.e., labels) include imaging agents, including fluorescent and luminescent substances, molecules, or compositions, including, but not limited to, a variety of organic or inorganic small molecules commonly referred to as "dyes," "labels," or "indicators." Examples include fluorescein, rhodamine, acridine dyes, Alexa dyes, and cyanine dyes. In embodiments, the detectable moiety is a fluorescent molecule (e.g., acridine dye, cyanine, dye, fluorine dye, oxazine dye, phenanthridine dye, or rhodamine dye). In embodiments, the detectable moiety is a fluorescent molecule (e.g., acridine dye, cyanine, dye, fluorine dye, oxazine dye, phenanthridine dye, or rhodamine dye). The term "cyanine" or "cyanine moiety" as described herein refers to a detectable moiety containing two nitrogen groups separated by a polymethine chain. In embodiments, the cyanine moiety has 3 methine structures (i.e. cyanine 3 or Cy3). In embodiments, the cyanine moiety has 5 methine structures (i.e. cyanine 5 or Cy5). In embodiments, the cyanine moiety has 7 methine structures (i.e., cyanine 7 or Cy7).

As used herein, the term "polymer" refers to macromolecules having one or more structurally unique repeating units. The repeating units are referred to as "monomers," which are polymerized for the polymer. Typically, a polymer is formed by monomers linked in a chain-like structure. A polymer formed entirely from a single type of monomer is referred to as a "homopolymer." A polymer formed from two or more unique repeating structural units may be referred to as a "copolymer." A polymer may be linear or branched, and may be random, block, polymer brush, hyperbranched polymer, bottlebrush polymer, dendritic polymer, or polymer micelles. The term "polymer" includes homopolymers, copolymers, tripolymers, tetra polymers and other polymeric molecules made from monomeric subunits. Copolymers include alternating copolymers, periodic copolymers, statistical copolymers, random copolymers, block copolymers, linear copolymers and branched copolymers. The term "polymerizable monomer" is used in accordance with its meaning in the art of polymer chemistry and refers to a compound that may covalently bind chemically to other monomer molecules (such as other polymerizable monomers that are the same or different) to form a polymer.

Polymers can be hydrophilic, hydrophobic or amphiphilic, as known in the art. Thus, "hydrophilic polymers" are substantially miscible with water and include, but are not limited to, polyethylene glycol and the like. "Hydrophobic polymers" are substantially immiscible with water and include, but are not limited to, polyethylene, polypropylene, polybutadiene, polystyrene, polymers disclosed herein, and the like. "Amphiphilic polymers" have both hydrophilic and hydrophobic properties and are typically copolymers having hydrophilic segment(s) and hydrophobic segment(s). Polymers include homopolymers, random copolymers, and block copolymers, as known in the art. The term "homopolymer" refers, in the usual and customary sense, to a polymer having a single monomeric unit. The term "copolymer" refers to a polymer derived from two or more monomeric species. The term "random copolymer" refers to a polymer derived from two or more monomeric species with no preferred ordering of the monomeric species. The term "block copolymer" refers to polymers having two or homopolymer subunits linked by covalent bond. Thus, the term "hydrophobic homopolymer" refers to a homopolymer which is hydrophobic. The term "hydrophobic block copolymer" refers to two or more homopolymer subunits linked by covalent bonds and which is hydrophobic.

As used herein, the term "hydrogel" refers to a three-dimensional polymeric structure that is substantially insoluble in water, but which is capable of absorbing and retaining large quantities of water to form a substantially stable, often soft and pliable, structure. In embodiments, water can penetrate in between polymer chains of a polymer network, subsequently causing swelling and the formation of a hydrogel. In embodiments, hydrogels are super-absorbent (e.g., containing more than about 90% water) and can be comprised of natural or synthetic polymers.

As used herein, the terms "solid support" and "substrate" and "substrate surface" and "solid surface" refers to discrete solid or semi-solid surfaces to which a plurality of functional groups (e.g., bioconjugate reactive moieties or specific binding reagents) may be attached. A solid support may encompass any type of solid, porous, or hollow sphere, ball, cylinder, or other similar configuration composed of plastic, ceramic, metal, or polymeric material (e.g., hydrogel) onto which a nucleic acid may be immobilized (e.g., covalently or non-covalently). A solid support may comprise a discrete particle that may be spherical (e.g., microspheres) or have a non-spherical or irregular shape, such as cubic, cuboid, pyramidal, cylindrical, conical, oblong, or disc-shaped, and the like. A bead can be non-spherical in shape. A solid support may be used interchangeably with the term "bead." A solid support may further comprise a polymer or hydrogel on the surface to which the primers are attached. Exemplary solid supports include, but are not limited to, glass and modified or functionalized glass, plastics (including acrylics, polystyrene and copolymers of styrene and other materials, polypropylene, polyethylene, polybutylene, polyurethanes, Teflon™, cyclic olefin copolymers, polyimides etc.), nylon, ceramics, resins, Zeonor, silica or silica-based materials including silicon and modified silicon, carbon, metals, inorganic glasses, optical fiber bundles, photopatternable dry film resists, UV-cured adhesives and polymers. The solid support, or regions thereof, can be substantially flat. The solid support can have surface features such as wells, pits, channels, ridges, raised regions, pegs, posts or the like. The term solid support is encompassing of a substrate having a surface comprising a plurality of functional groups covalently attached thereto, wherein the functional groups are selected to immobilize the sample.

As used herein, the term "selective" or "selectivity" or the like of a compound refers to the substance's ability to discriminate between molecular targets. As used herein, the terms "specific", "specifically", "specificity", or the like of a compound refers to the substance's ability to cause a particular action, such as binding, to a particular molecular target with minimal or no action to other substances (e.g., an antibody and antigen).

As used herein, the term "barcode" refers to a known nucleic acid sequence that allows some feature with which the barcode is associated to be identified. Typically, a barcode is unique to a particular feature in a pool of barcodes that differ from one another in sequence, and each of which is associated with a different feature. In embodiments, barcodes are about or at least about 5, 6, 7, 8, 9, 10, 15, 20, 25, 30, 40, 50, 75 or more nucleotides in length. In embodiments, barcodes are shorter than 20, 15, 10, 9, 8, 7, 6, or 5 nucleotides in length. In embodiments, barcodes are 10-50 nucleotides in length, such as 15-40 or 20-30 nucleotides in length. In a pool of different barcodes, barcodes may have the same or different lengths. In general, barcodes are of sufficient length and comprise sequences that are sufficiently different to allow the identification of associated features (e.g., a binding moiety or analyte) based on barcodes with which they are associated. In embodiments, a barcode can be identified accurately after the mutation, insertion, or deletion of one or more nucleotides in the barcode sequence, such as the mutation, insertion, or deletion of 1, 2, 3, 4, 5, or more nucleotides.

The terms "bind" and "bound" as used herein are used in accordance with their plain and ordinary meanings and refer to an association between atoms or molecules. The association can be direct or indirect. For example, bound atoms or molecules may be directly bound to one another, e.g., by a covalent bond or non-covalent bond (e.g. electrostatic interactions (e.g. ionic bond, hydrogen bond, halogen bond), van der Waals interactions (e.g. dipole-dipole, dipole-induced dipole, London dispersion), ring stacking (pi effects), hydrophobic interactions and the like). As a further example, two molecules may be bound indirectly to one another by way of direct binding to one or more intermediate molecules (e.g., as in a substrate, bound to a first antibody, bound to an analyte, bound to a second antibody), thereby forming a complex. As used herein, the term "attached" refers to the state of two things being joined, fastened, adhered, connected or bound to each other. For example, a sample such as a cell or tissue, can be attached to a material, such as a hydrogel, polymer, or solid support, by a covalent or non-covalent bond. In embodiments, attachment is a covalent attachment.

"Specific binding" is where the binding is selective between two molecules. A particular example of specific binding is that which occurs between an antibody and an antigen. Typically, specific binding can be distinguished from non-specific when the dissociation constant (KD) is less than about $1 \times 10^{-5}$ M or less than about $1 \times 10^{-6}$ M or $1 \times 10^{-7}$ M. Specific binding can be detected, for example, by ELISA, immunoprecipitation, coprecipitation, with or without chemical crosslinking, two-hybrid assays and the like.

Where a range of values is provided, it is understood that each intervening value, to the tenth of the unit of the lower limit unless the context clearly indicates otherwise, between the upper and lower limit of that range, and any other stated or unstated intervening value in, or smaller range of values within, that stated range is encompassed by such disclosure herein. The upper and lower limits of any such smaller range (within a more broadly recited range) may independently be included in the smaller ranges, or as particular values themselves, and are also encompassed by such disclosure herein, subject to any specifically excluded limit in the stated range. Where the stated range includes one or both of the limits, ranges excluding either or both of those included limits are also included by such disclosure herein.

As used herein, a "native nucleotide" is used in accordance with its plain and ordinary meaning and refers to a naturally occurring nucleotide that does not include an exogenous label (e.g., a fluorescent dye, or other label) or chemical modification such as may characterize a nucleotide analog. Examples of native nucleotides useful for carrying out procedures described herein include: dATP (2'-deoxyadenosine-5'-triphosphate); dGTP (2'-deoxyguanosine-5'-triphosphate); dCTP (2'-deoxycytidine-5'-triphosphate); dTTP (2'-deoxythymidine-5'-triphosphate); and dUTP (2'-deoxyuridine-5'-triphosphate).

Provided herein are methods, systems, and compositions for analyzing a sample (e.g., sequencing nucleic acids within a sample) in situ. The term "in situ" is used in accordance with its ordinary meaning in the art and refers to a sample surrounded by at least a portion of its native environment, such as may preserve the relative position of two or more elements. For example, an extracted human cell obtained is considered in situ when the cell is retained in its local microenvironment so as to avoid extracting the target (e.g., nucleic acid molecules or proteins) away from their native environment. An in situ sample (e.g., a cell) can be obtained from a suitable subject. An in situ cell sample may refer to a cell and its surrounding milieu, or a tissue. A sample can be isolated or obtained directly from a subject or part thereof. In embodiments, the methods described herein (e.g., sequencing a plurality of target nucleic acids of a cell in situ) are applied to an isolated cell (i.e., a cell not surrounded by least a portion of its native environment). For the avoidance of any doubt, when the method is performed within a cell (e.g., an isolated cell) the method may be considered in situ. In some embodiments, a sample is obtained indirectly from an individual or medical professional. A sample can be any specimen that is isolated or obtained from a subject or part thereof. A sample can be any specimen that is isolated or obtained from multiple subjects. Non-limiting examples of specimens include fluid or tissue from a subject, including, without limitation, blood or a blood product (e.g., serum, plasma, platelets, buffy coats, or the like), umbilical cord blood, chorionic villi, amniotic fluid, cerebrospinal fluid, spinal fluid, lavage fluid (e.g., lung, gastric, peritoneal, ductal, ear, arthroscopic), a biopsy sample, celocentesis sample, cells (blood cells, lymphocytes, placental cells, stem cells, bone marrow derived cells, embryo or fetal cells) or parts thereof (e.g., mitochondrial, nucleus, extracts, or the like), urine, feces, sputum, saliva, nasal mucous, prostate fluid, lavage, semen, lymphatic fluid, bile, tears, sweat, breast milk, breast fluid, the like or combinations thereof. Non-limiting examples of tissues include organ tissues (e.g., liver, kidney, lung, thymus, adrenals, skin, bladder, reproductive organs, intestine, colon, spleen, brain, the like or parts thereof), epithelial tissue, hair, hair follicles, ducts, canals, bone, eye, nose, mouth, throat, ear, nails, the like, parts thereof or combinations thereof. A sample may comprise cells or tissues that are normal, healthy, diseased (e.g., infected), and/or cancerous (e.g., cancer cells). A sample obtained from a subject may comprise cells or cellular material (e.g., nucleic acids) of multiple organisms (e.g., virus nucleic acid, fetal nucleic acid, bacterial nucleic acid, parasite nucleic acid). A sample may include a cell and RNA transcripts. A sample can comprise nucleic acids obtained from one or more subjects. In some embodiments a sample comprises nucleic acid obtained from a single subject. A subject can be any living or non-living organism, including but not limited to a human, non-human animal, plant, bacterium, fungus, virus, or protist. A subject may be any age (e.g., an embryo, a fetus, infant, child, adult). A subject can be of any sex (e.g., male, female, or combination thereof). A subject may be pregnant. In some embodiments, a subject is a mammal. In some embodiments, a subject is a plant. In some embodiments, a subject is a human subject. A subject can be a patient (e.g., a human patient). In some embodiments a subject is suspected of having a genetic variation or a disease or condition associated with a genetic variation.

As used herein, the term "disease state" is used in accordance with its plain and ordinary meaning and refers to any abnormal biological or aberrant state of a cell. The presence of a disease state may be identified by the same collection of biological constituents used to determine the cell's biological state. In general, a disease state will be detrimental to a biological system. A disease state may be a consequence of, inter alia, an environmental pathogen, for example a viral infection (e.g., HIV/AIDS, hepatitis B, hepatitis C, influenza, measles, etc.), a bacterial infection, a parasitic infection, a fungal infection, or infection by some other organism. A disease state may also be the consequence of some other environmental agent, such as a chemical toxin or a chemical carcinogen. As used herein, a disease state further includes genetic disorders wherein one or more copies of a gene is altered or disrupted, thereby affecting its biological function. Exemplary genetic diseases include, but are not limited to polycystic kidney disease, familial multiple endocrine neoplasia type I, neurofibromatoses, Tay-Sachs disease, Huntington's disease, sickle cell anemia, thalassemia, and Down's syndrome, as well as others (see, e.g., The Metabolic and Molecular Bases of Inherited Diseases, 7th ed., McGraw-Hill Inc., New York). Other exemplary diseases include, but are not limited to, cancer, hypertension, Alzheimer's disease, neurodegenerative diseases, and neuropsychiatric disorders such as bipolar affective disorders or paranoid schizophrenic disorders. Disease states are monitored to determine the level or severity (e.g., the stage or progression) of one or more disease states of a subject and, more specifically, detect changes in the biological state of a subject which are correlated to one or more disease states (see, e.g., U.S. Pat. No. 6,218,122, which is incorporated by reference herein in its entirety). In embodiments, methods provided herein are also applicable to monitoring the disease state or states of a subject undergoing one or more therapies. Thus, the present disclosure also provides, in some embodiments, methods for determining or monitoring efficacy of a therapy or therapies (i.e., determining a level of therapeutic effect) upon a subject. In embodiments, methods of the present disclosure can be used to assess therapeutic efficacy in a clinical trial, e.g., as an early surrogate marker for success or failure in such a clinical trial. Within eukaryotic cells, there are hundreds to thousands of signaling pathways that are interconnected. For this reason, perturbations in the function of proteins within a cell have numerous effects on other proteins and the transcription of other genes that are connected by primary, secondary, and sometimes tertiary pathways. This extensive interconnection between the function of various proteins means that the alteration of any one protein is likely to result in compensatory changes in a wide number of other proteins. In particular, the partial disruption of even a single protein within a cell, such as by exposure to a drug or by a disease state which modulates the gene copy number (e.g., a genetic mutation), results in characteristic compensatory changes in the transcription of enough other genes that these changes in transcripts can be used to define a "signature" of particular transcript alterations which are related to the disruption of function, e.g., a particular disease state or therapy, even at a stage where changes in protein activity are undetectable.

The terms "polypeptide," "peptide" and "protein" are used interchangeably herein to refer to a polymer of amino acid residues, wherein the polymer may optionally be conjugated to a moiety that does not consist of amino acids. The terms apply to amino acid polymers in which one or more amino acid residue is an artificial chemical mimetic of a corresponding naturally occurring amino acid, as well as to naturally occurring amino acid polymers and non-naturally occurring amino acid polymer. A protein may refer to a protein expressed in a cell.

A polypeptide, or a cell is "recombinant" when it is artificial or engineered, or derived from or contains an artificial or engineered protein or nucleic acid (e.g., non-natural or not wild type). For example, a polynucleotide that is inserted into a vector or any other heterologous location, e.g., in a genome of a recombinant organism, such that it is not associated with nucleotide sequences that normally flank the polynucleotide as it is found in nature is a recombinant polynucleotide. A protein expressed in vitro or in vivo from a recombinant polynucleotide is an example of a recombinant polypeptide. Likewise, a polynucleotide sequence that does not appear in nature, for example a variant of a naturally occurring gene, is recombinant.

As used herein, a "single cell" refers to one cell. Single cells useful in the methods described herein can be obtained from a tissue of interest, or from a biopsy, blood sample, or cell culture. Additionally, cells from specific organs, tissues, tumors, neoplasms, or the like can be obtained and used in the methods described herein. In general, cells from any population can be used in the methods, such as a population of prokaryotic or eukaryotic organisms, including bacteria or yeast.

The term "cellular component" is used in accordance with its ordinary meaning in the art and refers to any organelle, nucleic acid, protein, or analyte that is found in a prokaryotic, eukaryotic, archaeal, or other organismic cell type. Examples of cellular components (e.g., a component of a cell) include RNA transcripts, proteins, membranes, lipids, and other analytes.

A "gene" refers to a polynucleotide that is capable of conferring biological function after being transcribed and/or translated.

As used herein, the term "DNA polymerase" and "nucleic acid polymerase" are used in accordance with their plain ordinary meanings and refer to enzymes capable of synthesizing nucleic acid molecules from nucleotides (e.g., deoxyribonucleotides). Exemplary types of polymerases that may be used in the compositions and methods of the present disclosure include the nucleic acid polymerases such as DNA polymerase, DNA- or RNA-dependent RNA polymerase, and reverse transcriptase. In some cases, the DNA polymerase is 9°N polymerase or a variant thereof, *E. Coli* DNA polymerase I, Bacteriophage T4 DNA polymerase, Sequenase, Taq DNA polymerase, DNA polymerase from *Bacillus stearothermophilus*, Bst 2.0 DNA polymerase, 9°N polymerase (exo-)A485L/Y409V, Phi29 DNA Polymerase (φ29 DNA Polymerase), T7 DNA polymerase, DNA polymerase II, DNA polymerase III holoenzyme, DNA polymerase IV, DNA polymerase V, VentR DNA polymerase, Therminator™ II DNA Polymerase, Therminator™ III DNA Polymerase, or Therminator™ IX DNA Polymerase. In embodiments, the polymerase is a protein polymerase. Typically, a DNA polymerase adds nucleotides to the 3'-end of a DNA strand, one nucleotide at a time. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol DNA polymerase, or a thermophilic nucleic acid polymerase (e.g. Therminator γ, 9°N polymerase (exo-), Therminator II, Therminator III, or Therminator IX). In embodiments, the DNA polymerase is a modified archaeal DNA polymerase. In embodiments, the polymerase is a reverse transcriptase. In embodiments, the DNA polymerase is a *Thermus thermophilus* (Tth) DNA polymerase or mutant thereof (e.g., a Tth DNA polymerase exhibiting both reverse transcriptase and DNA polymerase activity as described in Myers T W and Gelfand D H. Biochem. 1991; 30(31): 7661-6 and Pantazaki A A et al. Appl. Microbiol. Biotechnol. 2002; 58:1-12, each of which are incorporated herein by reference for all purposes). In embodiments, the polymerase is a mutant *P. abyssi* polymerase (e.g., such as a mutant *P. abyssi* polymerase described in WO 2018/148723 or WO 2020/056044, each of which are incorporated herein by reference for all purposes).

As used herein, the term "thermophilic nucleic acid polymerase" refers to a family of DNA polymerases (e.g., 9°N™) and mutants thereof derived from the DNA polymerase originally isolated from the hyperthermophilic archaea, *Thermococcus* sp. 9 degrees N-7, found in hydrothermal vents at that latitude (East Pacific Rise) (Southworth M W, et al. *PNAS*. 1996; 93(11):5281-5285). A thermophilic nucleic acid polymerase is a member of the family B DNA polymerases. Site-directed mutagenesis of the 3'-5' exo motif I (Asp-Ile-Glu or DIE) to AIA, AIE, EIE, EID or DIA yielded polymerase with no detectable 3' exonuclease activity. Mutation to Asp-Ile-Asp (DID) resulted in reduction of 3'-5' exonuclease specific activity to <1% of wild type, while maintaining other properties of the polymerase including its high strand displacement activity. The sequence AIA (D141A, E143A) was chosen for reducing exonuclease. Subsequent mutagenesis of key amino acids results in an increased ability of the enzyme to incorporate dideoxynucleotides, ribonucleotides and acyclonucleotides (e.g., Therminator II enzyme from New England Biolabs with D141A/E143A/Y409V/A485L mutations); 3'-amino-dNTPs, 3'-azido-dNTPs and other 3'-modified nucleotides (e.g., NEB Therminator III DNA Polymerase with D141A/E143A/L4085/Y409A/P410V mutations, NEB Therminator IX DNA polymerase), or γ-phosphate labeled nucleotides (e.g., Therminator γ: D141A/E143A/W355A/L408W/R460A/Q4615/K464E/D480V/R484W/A485L). Typically, these enzymes do not have 5'-3' exonuclease activity. Additional information about thermophilic nucleic acid polymerases may be found in (Southworth M W, et al. *PNAS*. 1996; 93(11):5281-5285; Bergen K, et al. *ChemBioChem*. 2013; 14(9):1058-1062; Kumar S, et al. Scientific Reports. 2012; 2:684; Fuller C W, et al. 2016; 113(19):5233-5238; Guo J, et al. *Proceedings of the National Academy of Sciences of the United States of America*. 2008; 105(27): 9145-9150), which are incorporated herein in their entirety for all purposes.

As used herein, the term "exonuclease activity" is used in accordance with its ordinary meaning in the art, and refers to the removal of a nucleotide from a nucleic acid by a DNA polymerase. For example, during polymerization, nucleotides are added to the 3' end of the primer strand. Occasionally a DNA polymerase incorporates an incorrect nucleotide to the 3'-OH terminus of the primer strand, wherein the incorrect nucleotide cannot form a hydrogen bond to the corresponding base in the template strand. Such a nucleotide, added in error, is removed from the primer as a result of the 3' to 5' exonuclease activity of the DNA polymerase. In embodiments, exonuclease activity may be referred to as "proofreading." When referring to 3'-5' exonuclease activity, it is understood that the DNA polymerase facilitates a hydrolyzing reaction that breaks phosphodiester bonds at either the 3' end of a polynucleotide chain to excise the nucleotide. In embodiments, 3'-5' exonuclease activity refers to the successive removal of nucleotides in single-stranded DNA in a 3'→5' direction, releasing deoxyribonucleoside 5'-monophosphates one after another. Methods for quantifying exonuclease activity are known in the art, see for example Southworth et al, PNAS Vol 93, 8281-8285 (1996).

As used herein, the term "extension" or "elongation" is used in accordance with its plain and ordinary meanings and refer to synthesis by a polymerase of a new polynucleotide strand complementary to a template strand by adding free nucleotides (e.g., dNTPs) from a reaction mixture that are complementary to the template in the 5'-to-3' direction. Extension includes condensing the 5'-phosphate group of the dNTPs with the 3'-hydroxy group at the end of the nascent (elongating) polynucleotide strand.

As used herein, the term "kit" refers to any delivery system for delivering materials. In the context of reaction assays, such delivery systems include systems that allow for the storage, transport, or delivery of reaction reagents (e.g., oligonucleotides, enzymes, etc. in the appropriate containers) and/or supporting materials (e.g., buffers, written instructions for performing the assay, etc.) from one location to another. For example, kits include one or more enclosures (e.g., boxes) containing the relevant reaction reagents and/or supporting materials. As used herein, the term "fragmented kit" refers to a delivery system comprising two or more separate containers that each contain a subportion of the total kit components. The containers may be delivered to the intended recipient together or separately. For example, a first container may contain an enzyme for use in an assay, while a second container contains oligonucleotides. In contrast, a "combined kit" refers to a delivery system containing all of the components of a reaction assay in a single container (e.g., in a single box housing each of the desired components). The term "kit" includes both fragmented and combined kits.

As used herein the term "determine" can be used to refer to the act of ascertaining, establishing or estimating. A determination can be probabilistic. For example, a determination can have an apparent likelihood of at least 50%, 75%, 90%, 95%, 98%, 99%, 99.9% or higher. In some cases, a determination can have an apparent likelihood of 100%. An exemplary determination is a maximum likelihood analysis or report. As used herein, the term "identify," when used in reference to a thing, can be used to refer to recognition of the thing, distinction of the thing from at least one other thing or categorization of the thing with at least one other thing. The recognition, distinction or categorization can be probabilistic. For example, a thing can be identified with an apparent likelihood of at least 50%, 75%, 90%, 95%, 98%, 99%, 99.9% or higher. A thing can be identified based on a result of a maximum likelihood analysis. In some cases, a thing can be identified with an apparent likelihood of 100%.

As used herein, the terms "sequencing", "sequence determination", and "determining a nucleotide sequence", are used in accordance with their ordinary meaning in the art, and refer to determination of partial as well as full sequence information of the nucleic acid being sequenced, and particular physical processes for generating such sequence information. That is, the term includes sequence comparisons, fingerprinting, and like levels of information about a target nucleic acid, as well as the express identification and ordering of nucleotides in a target nucleic acid. The term also includes the determination of the identification, ordering, and locations of one, two, or three of the four types of nucleotides within a target nucleic acid. Sequencing produces a sequencing read.

As used herein, the term "sequencing cycle" is used in accordance with its plain and ordinary meaning and refers to incorporating one or more nucleotides (e.g., a compound described herein) to the 3' end of a polynucleotide with a polymerase, and detecting one or more labels that identify the one or more nucleotides incorporated. The sequencing may be accomplished by, for example, sequencing by synthesis, pyrosequencing, and the like. In embodiments, a sequencing cycle includes extending a complementary polynucleotide by incorporating a first nucleotide using a polymerase, wherein the polynucleotide is hybridized to a template nucleic acid, detecting the first nucleotide, and identifying the first nucleotide. In embodiments, to begin a sequencing cycle, one or more differently labeled nucleotides and a DNA polymerase can be introduced. Following nucleotide addition, signals produced (e.g., via excitation and emission of a detectable label) can be detected to determine the identity of the incorporated nucleotide (based on the labels on the nucleotides). Reagents can then be added to remove the 3' reversible terminator and to remove labels from each incorporated base. Reagents, enzymes and other substances can be removed between steps by washing. Cycles may include repeating these steps, and the sequence of each cluster is read over the multiple repetitions.

As used herein, the term "sequencing read" is used in accordance with its plain and ordinary meaning and refers to an inferred sequence of nucleotide base pairs (or nucleotide base pair probabilities) corresponding to all or part of a single polynucleotide fragment. A sequencing read may include 10, 20, 30, 40, 50, 60, 70, 80, 90, 100, 150, 200, 250, or more nucleotide base pairs. In embodiments, a sequencing read includes reading a barcode and a template nucleotide sequence. In embodiments, a sequencing read includes reading a template nucleotide sequence. As used herein, the term "sequencing read" refers to an inferred sequence of base pairs (or base pair probabilities) corresponding to all or part of a single DNA fragment.

As used herein a "genetically modifying agent" is a substance that alters the genetic sequence of a cell following exposure to the cell, resulting in an agent-mediated nucleic acid sequence. In embodiments, the genetically modifying agent is a small molecule, protein, pathogen (e.g., virus or bacterium), toxin, oligonucleotide, or antigen. In embodiments, the genetically modifying agent is a virus (e.g., influenza) and the agent-mediated nucleic acid sequence is the nucleic acid sequence that develops within a T-cell upon cellular exposure and contact with the virus. In embodiments, the genetically modifying agent modulates the expression of a nucleic acid sequence in a cell relative to a control (e.g., the absence of the genetically modifying agent).

The term "synthetic target" as used herein refers to a modified protein or nucleic acid such as those constructed by synthetic methods. In embodiments, a synthetic target is artificial or engineered, or derived from or contains an artificial or engineered protein or nucleic acid (e.g., non-natural or not wild type). For example, a polynucleotide that is inserted or removed such that it is not associated with nucleotide sequences that normally flank the polynucleotide as it is found in nature is a synthetic target polynucleotide.

The terms "bioconjugate group," "bioconjugate reactive moiety," and "bioconjugate reactive group" refer to a chemical moiety which participates in a reaction to form a bioconjugate linker (e.g., covalent linker). Non-limiting examples of bioconjugate groups include —$NH_2$, —COOH, —$COOCH_3$, —N-hydroxysuccinimide, -maleimide,

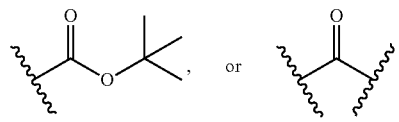

In embodiments, the bioconjugate reactive group may be protected (e.g., with a protecting group). In embodiments, the bioconjugate reactive moiety is

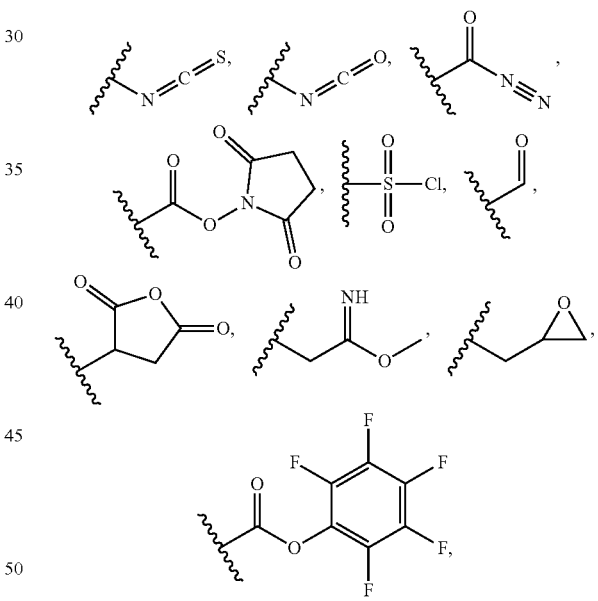

or —$NH_2$. Additional examples of bioconjugate reactive groups and the resulting bioconjugate reactive linkers may be found in the Bioconjugate Table below:

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| activated esters | amines/anilines | carboxamides |
| acrylamides | thiols | thioethers |
| acyl azides | amines/anilines | carboxamides |
| acyl halides | amines/anilines | carboxamides |
| acyl halides | alcohols/phenols | esters |

| Bioconjugate reactive group 1 (e.g., electrophilic bioconjugate reactive moiety) | Bioconjugate reactive group 2 (e.g., nucleophilic bioconjugate reactive moiety) | Resulting Bioconjugate reactive linker |
|---|---|---|
| acyl nitriles | alcohols/phenols | esters |
| acyl nitriles | amines/anilines | carboxamides |
| aldehydes | amines/anilines | imines |
| aldehydes or ketones | hydrazines | hydrazones |
| aldehydes or ketones | hydroxylamines | oximes |
| alkyl halides | amines/anilines | alkyl amines |
| alkyl halides | carboxylic acids | esters |
| alkyl halides | thiols | thioethers |
| alkyl halides | alcohols/phenols | ethers |
| alkyl sulfonates | thiols | thioethers |
| alkyl sulfonates | carboxylic acids | esters |
| alkyl sulfonates | alcohols/phenols | ethers |
| anhydrides | alcohols/phenols | esters |
| anhydrides | amines/anilines | carboxamides |
| aryl halides | thiols | thiophenols |
| aryl halides | amines | aryl amines |
| aziridines | thiols | thioethers |
| boronates | glycols | boronate esters |
| carbodiimides | carboxylic acids | N-acylureas or anhydrides |
| diazoalkanes | carboxylic acids | esters |
| epoxides | thiols | thioethers |
| haloacetamides | thiols | thioethers |
| haloplatinate | amino | platinum complex |
| haloplatinate | heterocycle | platinum complex |
| haloplatinate | thiol | platinum complex |
| halotriazines | amines/anilines | aminotriazines |
| halotriazines | alcohols/phenols | triazinyl ethers |
| halotriazines | thiols | triazinyl thioethers |
| imido esters | amines/anilines | amidines |
| isocyanates | amines/anilines | ureas |
| isocyanates | alcohols/phenols | urethanes |
| isothiocyanates | amines/anilines | thioureas |
| maleimides | thiols | thioethers |
| phosphoramidites | alcohols | phosphite esters |
| silyl halides | alcohols | silyl ethers |
| sulfonate esters | amines/anilines | alkyl amines |
| sulfonate esters | thiols | thioethers |
| sulfonate esters | carboxylic acids | esters |
| sulfonate esters | alcohols | ethers |
| sulfonyl halides | amines/anilines | sulfonamides |
| sulfonyl halides | phenols/alcohols | sulfonate esters |

As used herein, the term "bioconjugate" or "bioconjugate linker" refers to the resulting association between atoms or molecules of bioconjugate reactive groups. The association can be direct or indirect. For example, a conjugate between a first bioconjugate reactive group (e.g., —NH$_2$, —COOH, —N-hydroxysuccinimide, or -maleimide) and a second bioconjugate reactive group (e.g., sulfhydryl, sulfur-containing amino acid, amine, amine sidechain containing amino acid, or carboxylate) provided herein can be direct, e.g., by covalent bond or linker (e.g., a first linker of second linker), or indirect, e.g., by non-covalent bond (e.g., electrostatic interactions (e.g., ionic bond, hydrogen bond, halogen bond), van der Waals interactions (e.g., dipole-dipole, dipole-induced dipole, London dispersion), ring stacking (pi effects), hydrophobic interactions and the like). In embodiments, bioconjugates or bioconjugate linkers are formed using bioconjugate chemistry (i.e., the association of two bioconjugate reactive groups) including, but not limited to nucleophilic substitutions (e.g., reactions of amines and alcohols with acyl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the first bioconjugate reactive group (e.g., maleimide moiety) is covalently attached to the second bioconjugate reactive group (e.g., a sulfhydryl). In embodiments, the first bioconjugate reactive group (e.g., haloacetyl moiety) is covalently attached to the second bioconjugate reactive group (e.g., a sulfhydryl). In embodiments, the first bioconjugate reactive group (e.g., pyridyl moiety) is covalently attached to the second bioconjugate reactive group (e.g., a sulfhydryl). In embodiments, the first bioconjugate reactive group (e.g., —N-hydroxysuccinimide moiety) is covalently attached to the second bioconjugate reactive group (e.g., an amine). In embodiments, the first bioconjugate reactive groups (e.g., dibenzocyclooctyne (DBCO)) is covalently attached to the second bioconjugate reactive group (e.g., an azide). In embodiments, the first bioconjugate reactive group (e.g., maleimide moiety) is covalently attached to the second bioconjugate reactive group (e.g., a sulfhydryl). In embodiments, the first bioconjugate reactive group (e.g., -sulfo-N-hydroxysuccinimide moiety) is covalently attached to the second bioconjugate reactive group (e.g., an amine). In embodiments, the first bioconjugate reactive group (e.g., —COOH) is covalently attached to the second bioconjugate reactive group (e.g., 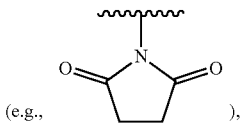 [SMILES: *N1C(=O)CCC1=O]), thereby forming a bioconjugate (e.g., 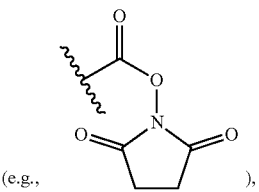 [SMILES: *C(=O)ON1C(=O)CCC1=O]).

In embodiments, the first bioconjugate reactive group (e.g., —NH$_2$) is covalently attached to the second bioconjugate reactive group (e.g., 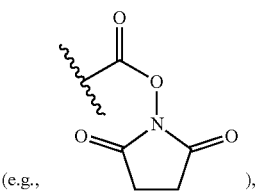 [SMILES: *C(=O)ON1C(=O)CCC1=O]), thereby forming a bioconjugate (e.g., 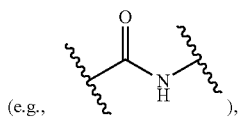 [SMILES: *NC(*)=O]), In embodiments, the first bioconjugate reactive group (e.g., a coupling reagent) is covalently attached to the second bioconjugate reactive group (e.g., 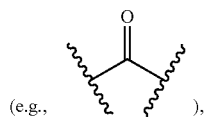), thereby forming a bioconjugate (e.g., 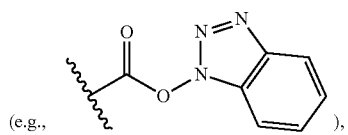), The bioconjugate reactive groups can be chosen such that they do not participate in, or interfere with, the chemical stability of the conjugate described herein. Alternatively, a reactive functional group can be protected from participating in the crosslinking reaction by the presence of a protecting group. In embodiments, the bioconjugate comprises a molecular entity derived from the reaction of an unsaturated bond, such as a maleimide, and a sulfhydryl group.

Useful bioconjugate reactive groups used for bioconjugate chemistries herein include, for example: (a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters; (b) hydroxyl groups which can be converted to esters, ethers, aldehydes, etc.; (c) haloalkyl groups wherein the halide can be later displaced with a nucleophilic group such as, for example, an amine, a carboxylate anion, thiol anion, carbanion, or an alkoxide ion, thereby resulting in the covalent attachment of a new group at the site of the halogen atom; (d) dienophile groups which are capable of participating in Diels-Alder reactions such as, for example, maleimido or maleimide groups; (e) aldehyde or ketone groups such that subsequent derivatization is possible via formation of carbonyl derivatives such as, for example, imines, hydrazones, semicarbazones or oximes, or via such mechanisms as Grignard addition or alkyllithium addition; (f) sulfonyl halide groups for subsequent reaction with amines, for example, to form sulfonamides; (g) thiol groups, which can be converted to disulfides, reacted with acyl halides, or bonded to metals such as gold, or react with maleimides; (h) amine or sulfhydryl groups (e.g., present in cysteine), which can be, for example, acylated, alkylated or oxidized; (i) alkenes, which can undergo, for example, cycloadditions, acylation, Michael addition, etc.; (j) epoxides, which can react with, for example, amines and hydroxyl compounds; (k) phosphoramidites and other standard functional groups useful in nucleic acid synthesis; (l) metal silicon oxide bonding; (m) metal bonding to reactive phosphorus groups (e.g., phosphines) to form, for example, phosphate diester bonds; (n) azides coupled to alkynes using copper catalyzed cycloaddition click chemistry; (o) biotin conjugate can react with avidin or strepavidin to form a avidin-biotin complex or streptavidin-biotin complex.

An "antibody" (Ab) is a protein that binds specifically to a particular substance, known as an "antigen" (Ag). An "antibody" or "antigen-binding fragment" is an immunoglobulin that binds a specific "epitope." The term encompasses polyclonal, monoclonal, and chimeric antibodies. In nature, antibodies are generally produced by lymphocytes in response to immune challenge, such as by infection or immunization. An "antigen" (Ag) is any substance that reacts specifically with antibodies or T lymphocytes (T cells). An antibody may include the entire antibody as well as any antibody fragments capable of binding the antigen or antigenic fragment of interest. Examples include complete antibody molecules, antibody fragments, such as Fab, F(ab')2, CDRs, VL, VH, and any other portion of an antibody which is capable of specifically binding to an antigen. Antibodies used herein are immunospecific for, and therefore specifically and selectively bind to, for example, proteins either detected (e.g., biological targets of interest) or used for detection (e.g., probes containing oligonucleotide barcodes) in the methods and devices as described herein.

As used herein, the term "control" or "control experiment" is used in accordance with its plain and ordinary meaning and refers to an experiment in which the subjects, cells, tissues, or reagents of the experiment are treated as in a parallel experiment except for omission of a procedure, reagent, or variable of the experiment. In some instances, the control is used as a standard of comparison in evaluating experimental effects. In embodiments, a control cell is the same cell type as the cell being examined, wherein the control cell does not include the variable or is subjected to conditions being examined.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

II. Compositions and Kits

In an aspect is provided a polynucleotide including a plurality of units. In embodiments, each unit includes a portion of a genomic sequence and an oligonucleotide primer, wherein each oligonucleotide primer includes: a) a first region at a 3' end that is hybridized to a first complementary region of the polynucleotide, and b) a second region at a 5' end that is hybridized to a second complementary region of the polynucleotide, wherein the second complementary region is 5' with respect to the first complementary region. In embodiments, the polynucleotide is within a cell. In embodiments, the polynucleotide includes three or more units. In embodiments, the polynucleotide is within a cell. In embodiments, the polynucleotide includes three or more units. In embodiments, the oligonucleotide primer has a first domain that is capable of hybridizing to a first target sequence domain, and a second domain capable of hybridizing to a second target sequence domain. In embodiments, the length of the first domain and second domain are the same length (e.g., both the first and the second domains are about 15 nucleotides). In embodiments, the length of the first domain and second domain are different lengths (e.g., the first domain is about 10 nucleotides and the second domain is about 20 nucleotides). In embodiments, an asymmetric oligonucleotide primer (i.e., an oligonucleotide primer having a first domain and second domain that are different lengths) may be advantageous in preventing non-specific hybridization. In embodiments, the total length of the first domain and second domain combined is about 25, 30, 35, or 40 nucleotides. In embodiments, the total length of the first domain and second domain combined is about 30 nucleotides.

In an aspect, provided herein are kits for use in accordance with any of the compounds, compositions, or methods disclosed herein, and including one or more elements thereof. In embodiments, a kit includes labeled nucleotides including differently labeled nucleotides, enzymes, buffers, oligonucleotides, and related solvents and solutions. In embodiments, the kit includes an oligonucleotide primer (e.g., an oligonucleotide primer as described herein). The kit may also include a template nucleic acid (DNA and/or RNA), one or more primer polynucleotides, nucleoside triphosphates (including, e.g., deoxyribonucleotides, dideoxynucleotides, ribonucleotides, labeled nucleotides, and/or modified nucleotides), buffers, salts, and/or labels (e.g., fluorophores). In embodiments, the kit includes components useful for circularizing template polynucleotides using a ligation enzyme (e.g., Circligase enzyme, Taq DNA Ligase, HiFi Taq DNA Ligase, T4 ligase, SplintR ligase, or Ampligase DNA Ligase). For example, such a kit further includes the following components: (a) reaction buffer for controlling pH and providing an optimized salt composition for a ligation enzyme (e.g., Circligase enzyme, Taq DNA Ligase, HiFi Taq DNA Ligase, T4 ligase, SplintR ligase, or Ampligase DNA Ligase), and (b) ligation enzyme cofactors. In embodiments, the kit further includes instructions for use thereof. In embodiments, kits described herein include a polymerase. In embodiments, the polymerase is a DNA polymerase. In embodiments, the DNA polymerase is a thermophilic nucleic acid polymerase. In embodiments, the DNA polymerase is a modified archaeal DNA polymerase. In embodiments, the kit includes a sequencing solution. In embodiments, the sequencing solution include labeled nucleotides including differently labeled nucleotides, wherein the label (or lack thereof) identifies the type of nucleotide. For example, each adenine nucleotide, or analog thereof; a thymine nucleotide; a cytosine nucleotide, or analog thereof; and a guanine nucleotide, or analog thereof may be labeled with a different fluorescent label.

III. Methods

In an aspect is provided a method of profiling a sample (e.g., a cell). In embodiments, the method includes determining information (e.g., gene and protein expression) about the transcriptome of an organism thus elucidating subcellular substances and processes while gaining valuable spatial localization information within a cell. In embodiments, the method includes simultaneously sequencing a plurality of nucleic acids, such as RNA transcripts, in situ within an optically resolved volume of a sample (e.g., a voxel). RNA transcripts are responsible for the process of converting DNA into an organism's phenotype, thus by determining the types and quantity of RNA present in a sample (e.g., a cell), it is possible to assign a phenotype to the cell. RNA transcripts include coding RNA and non-coding RNA molecules, such as messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA). In embodiments, the target is pre-mRNA. In embodiments, the target is heterogeneous nuclear RNA (hnRNA).

In an aspect is provided a method of sequencing a plurality of target nucleic acids of a cell in situ. In embodiments, the method includes the following steps in situ for each of the plurality of target nucleic acids: i) hybridizing an oligonucleotide primer to the target nucleic acid, wherein the oligonucleotide primer includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region; ii) circularizing the oligonucleotide primer to generate a circular oligonucleotide, wherein circularizing includes extending the 3' end of the oligonucleotide primer (e.g., extending the 3' end of the primer using a polymerase (e.g., a *Thermus thermophilus* (Tth) DNA polymerase) to incorporate one or more nucleotides) along the target nucleic acid to generate a complementary sequence (e.g., complementary to the target nucleic acid, for example a target RNA sequence), and ligating the complementary sequence to the 5' end of the oligonucleotide primer; iii) amplifying the circular oligonucleotide by extending an amplification primer hybridized to the circular oligonucleotide with a strand-displacing polymerase, wherein the amplification primer extension generates an extension product including multiple complements of the circular oligonucleotide; and iv) sequencing the extension product of step (iii).

In an aspect is provided a method of sequencing a plurality of target nucleic acids of a granuloma in situ. In embodiments, the method includes the following steps in situ for each of the plurality of target nucleic acids: i) hybridizing an oligonucleotide primer to the target nucleic acid, wherein the oligonucleotide primer includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region; ii) circularizing the oligonucleotide primer to generate a circular oligonucleotide, wherein circularizing includes extending the 3' end of the oligonucleotide primer (e.g., extending the 3' end of the primer using a polymerase (e.g., a *Thermus thermophilus* (Tth) DNA polymerase) to incorporate one or more nucleotides) along the target nucleic acid to generate a complementary sequence (e.g., complementary to the target nucleic acid, for example a target RNA sequence), and ligating the complementary sequence to the 5' end of the oligonucleotide primer; iii) amplifying the circular oligonucleotide by extending an amplification primer hybridized to the circular oligonucleotide with a strand-displacing polymerase, wherein the amplification primer extension generates an extension product including multiple complements of the circular oligonucleotide; and iv) sequencing the extension product of step (iii). In embodiments, the granuloma is a tuberculosis granuloma (i.e., a TB granuloma). In embodiments, the granuloma includes one or more of the following: a *Mycobacterium tuberculosis* (MTb) cell, macrophage (e.g., a histiocyte), multinucleated giant cell (e.g., Langhans giant cell), epithelioid cell, Foamy cell, and/or lymphocyte. In embodiments, the granuloma includes a *Mycobacterium tuberculosis* (MTb) nucleic acid. In embodiments, the TB granuloma is obtained from a tissue sample. In embodiments, the granuloma is a collection of a plurality of TB granuloma cells. In embodiments, the TB granuloma cell is obtained from a solid granuloma. A solid granuloma is characterized by an intact structure with the macrophage-rich center surrounded by T cells and B cells resulting in a lymphocytic cuff at the periphery. With time, however, some granulomas can undergo complex remodeling characterized by the accumulation of necrotic material that leads to the formation of caseum at the center. In embodiments, the TB granuloma cell is obtained from a caseous granuloma. The caseum may undergo liquefaction resulting in cavitation—the destructive fusion of a liquefying granuloma with an adjacent airway—which facilitates bacterial dissemination (see, e.g., Marakalala M J et al. Nat. Med. 2016; 22(5): 531-538). In embodiments, the TB granuloma cell is obtained from a subject with a cavitary or transmissive granuloma. The transmissive granuloma is characterized by high Mtb growth and dissemination, and high levels of polymorphonuclear neutrophil (PMN) (see, e.g., Ehlers S and Schaible U E. Front. Immunol. 2013; 3: 411).

In embodiments, the granuloma includes a gene for lipid sequestration and metabolism (see, e.g., Kim M J et al. EMBO Mol. Med. 2010; 2(7): 258-274), e.g., Carnitine 0-acetyltransferase (CRAT), Cytochrome P450, family 1, subfamily B, polypeptide 1 (CYP1B1), Cytochrome P450, family 27, subfamily A, polypeptide 1 (CYP27A1), adipophilin (ADFP), degenerative spermatocyte homologue 1, lipid desaturase (DEGS1), acyl-CoA synthetase long chain fatty acid family member 1 (ACSL1), acyl-CoA synthetase long chain fatty acid family member 3 (ACSL3), acyl-CoA synthetase long chain fatty acid family member 4 (ACSL4), acyl-CoA synthetase long chain fatty acid family member 5 (ACSL5), saposin C (SapC), 7-Dehydrocholesterol reductase (DHCR7), abhydrolase domain containing 5 (ABHDS), ATP citrate lyase (ACLY), Emopamil binding protein (EBP), Elovl family member 5, elongation of long chain fatty acids (ELOVLS), Fatty acid desaturase 1 (FADS1), Farnesyl diphosphate synthase (FDPS), Glucosidase, beta, acid (GBA), Galactosidase, alpha (GLA), Galactosidase, beta 1 (GLB1), Glycerol-3-phosphate dehydrogenase 2 (GPD2), Hydroxyacyl-Coenzyme A dehydrogenase/3-ketoacyl-Coenzyme A thiolase/enoyl-Coenzyme A hydratase, alpha subunit (HADHA), 3-Hydroxy-3methyl-glutaryl-Coenzyme A reductase (HMGCR), Isopentenyl-diphosphate delta isomerase 1 (IDI1), Lipase A, lysosomal acid, cholesterol esterase (LIPA), Lanosterol synthase (LSS), Phospholipid scramblase 1 (PLSCR1), Stearoyl-CoA desaturase (SCD), Sterol-C5-desaturase (SC5DL), Sterol O-acyltransferase 1 (SOAT1), Sphingosine kinase 2 (SPHK2), Triosephosphate isomerase 1 (TPI1), and/or pro-saposin (PSAP). In embodiments, the granuloma includes a gene for proteins that metabolize arachidonic acid (see, e.g., Marakalala M J et al. Nat. Med. 2016; 22(5): 531-538), e.g., Arachidonate 5-lipoxygenase (ALOX5), Arachidonate 5-lipoxygenase activating protein (ALOX5AP), and/or Leukotriene A4 hydrolase (LTA4H). In embodiments, the granuloma includes a gene for prostanoid synthesis, e.g., Cyclo-oxygenase 1 (COX1) and/or Cyclo-oxygenase 2 (COX2). In embodiments, the granuloma includes genes encoding cytokines, e.g., IFNγ and/or TGF-beta. In embodiments, the granuloma includes genes associated with immunosuppression, e.g., FOX3P and/or IL10. In embodiments, the granuloma includes genes that are involved in TB drug (e.g., rifampin, ethambutol, isoniazid, and/or pyrazinamide) resistance, e.g., rpoB, embB, inhA, and/or pncA. In embodiments, the granuloma includes the rpoB gene, or fragment thereof. In embodiments, the granuloma includes the embB gene, or fragment thereof. In embodiments, the granuloma includes the inhB gene, or fragment thereof. In embodiments, the granuloma includes the pncA gene, or fragment thereof. In embodiments, one or more of these genes comprises a mutation. In embodiments, the expression of one or more of these genes is altered (e.g., increased), relative to a normal control cell.

In embodiments, the granuloma cell is obtained (e.g., by fine-needle aspiration or surgical biopsy) from a tissue. In embodiments, the tissue is lung tissue, lymph node tissue, throat tissue, cervical tissue, intramammary tissue, inguinal tissue, mesenteric tissue, mediastinal tissue, intracranial tissue, gastrointestinal tissue, and/or bone tissue.

Typically, following a TB infection, the tissue site organizes into a granuloma, which includes of a core of infected macrophages surrounded by foamy and epithelioid macrophages, monocytes, and multinucleated giant cells (MGCs). The periphery of the granuloma includes fibroblasts which provides a fibrous capsule around the macrophage-rich core. Typically, lymphocytes abundant at the periphery of granuloma. In embodiments, the method further includes monitoring the disease state of an individual. In embodiments, monitoring the disease state of an individual includes comparing the plurality of detected targets in the granuloma cell to a reference cell. In embodiments, monitoring the disease state of an individual includes comparing the plurality of detected targets in the granuloma to a control (e.g., a reference cell, such as a cell from normal lunch parenchyma). In embodiments, monitoring the disease state of an individual includes comparing the plurality of detected targets in the granuloma to a plurality of detected targets in a normal cell over a period of time. In embodiments, the comparison is performed over a period of days, weeks, months, or years.

In an aspect is provided a method of sequencing a plurality of target nucleic acids of a triple negative breast cancer (TNBC) tumor cell in situ. In embodiments, the method includes the following steps in situ for each of the plurality of target nucleic acids: i) hybridizing an oligonucleotide primer to the target nucleic acid, wherein the oligonucleotide primer includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region; ii) circularizing the oligonucleotide primer to generate a circular oligonucleotide, wherein circularizing includes extending the 3' end of the oligonucleotide primer (e.g., extending the 3' end of the primer using a polymerase (e.g., a *Thermus thermophilus* (Tth) DNA polymerase) to incorporate one or more nucleotides) along the target nucleic acid to generate a complementary sequence (e.g., complementary to the target nucleic acid, for example a target RNA sequence), and ligating the complementary sequence to the 5' end of the oligonucleotide primer; iii) amplifying the circular oligonucleotide by extending an amplification primer hybridized to the circular oligonucleotide with a strand-displacing polymerase, wherein the amplification primer extension generates an extension product including multiple complements of the circular oligonucleotide; and iv) sequencing the extension product of step (iii). In embodiments, the TNBC tumor cell is obtained after a tumor has been surgically removed. In embodiments, the TNBC tumor cell is a residual tumor cell following surgical removal of a tumor. In embodiments, the TNBC tumor cell is obtained after a tumor has been contacted with a pharmacological agent. In embodiments, the TNBC tumor cell is obtained before a tumor has been contacted with a pharmacological agent. In embodiments, the method further includes monitoring the disease state of an individual. In embodiments, monitoring the disease state of an individual includes comparing the plurality of detected targets in the tumor cell to a reference cell. In embodiments, monitoring the disease state of an individual includes comparing the plurality of detected targets in the tumor cell to a plurality of detected targets in a normal cell. In embodiments, monitoring the disease state of an individual includes comparing the plurality of detected targets in the tumor cell to a plurality of detected targets in a normal cell over a period of time. In embodiments, the comparison is performed over a period of hours, days, weeks, months, or years.

In embodiments, the TNBC tumor includes one or more of the following: tumor-associated macrophages (TAMs), $CD4^+$ tumor-infiltrating lymphocytes (TILs), $CD8^+$ TILs, and/or $FOXP3^+$ TILs. In embodiments, the TNBC tumor cell includes a gene involved in homologous recombination repair (see, e.g., Cocco S et al. Int. J. Mol. Sci. 2020; 21(13): 4579), e.g., BRCA1, BRCA2, ATM, BARD1, BRIP1, CDK12, CHEK1, CHEK2, FANCL, PALB2, PPP2R2A, RAD51B, RAD51C, RAD51D, and/or RAD54L. In embodiments, one or more of these genes comprises a mutation. In embodiments, the expression of one or more of these genes is altered (e.g., decreased), relative to a normal control cell.

In embodiments, the TNBC tumor cell includes a gene involved in cell cycle and proliferation (see, e.g., Sporikova Z et al. Clin. Breast Cancer. 2018; 18(5): e841-e850), e.g., MYC, NRAS, Ki-67, EGFR, MET, EPHA2, and/or TP53. In embodiments, the TNBC tumor cell includes a gene involved in chemotherapeutic resistance, e.g., TNF, VEGFA, IL-6, TNFSF10, CLU, ABCC6, EGR1, SNAIL ABCC3, EPHX1, FASN, CXCL1, IL24, JUNB, and/or TP53I11. In embodiments, the TNBC tumor cell includes a gene involved in immune cell signaling processes, e.g., JAK1/2, STAT1/4, IRF1/7/8, and/or TNF. In embodiments, the TNBC tumor cell includes a gene involved in androgen/estrogen metabolism, steroid synthesis, porphyrin metabolism, e.g., AR, FOXA1, KRT18, and/or XBP1. In embodiments, one or more of these genes comprises a mutation. In embodiments, the expression of one or more of these genes is altered (e.g., increased), relative to a normal control cell.

In embodiments, the TNBC tumor includes one or more of the following cell types: breast cells, persister cells, and/or cancer stem-like cells. In embodiments, the TNBC tumor is classified as a basal-like 1 subtype, basal-like 2 subtype, an immunomodulatory subtype, a mesenchymal subtype, a mesenchymal stem-like subtype, or a luminal androgen receptor subtype (see, e.g., Lehmann B D et al. J. Clin. Invest. 2011; 121(7): 2750-67).

In an aspect is provided a method of sequencing a plurality of target nucleic acids of a glioblastoma multiforme (GBM) tumor cell in situ. In embodiments, the method includes the following steps in situ for each of the plurality of target nucleic acids: i) hybridizing an oligonucleotide primer to the target nucleic acid, wherein the oligonucleotide primer includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region; ii) circularizing the oligonucleotide primer to generate a circular oligonucleotide, wherein circularizing includes extending the 3' end of the oligonucleotide primer (e.g., extending the 3' end of the primer using a polymerase (e.g., a *Thermus thermophilus* (Tth) DNA polymerase) to incorporate one or more nucleotides) along the target nucleic acid to generate a complementary sequence (e.g., complementary to the target nucleic acid, for example a target RNA sequence), and ligating the complementary sequence to the 5' end of the oligonucleotide primer; iii) amplifying the circular oligonucleotide by extending an amplification primer hybridized to the circular oligonucleotide with a strand-displacing polymerase, wherein the amplification primer extension generates an extension product including multiple complements of the circular oligonucleotide; and iv) sequencing the extension product of step (iii). In embodiments, the GBM tumor cell includes cells from the tumor microenvironment. In embodiments, the GBM tumor cell is a residual tumor cell following surgical removal of a tumor. In embodiments, the GBM tumor cell is obtained after a tumor has been contacted with a pharmacological agent. In embodiments, the GBM tumor cell is obtained before a tumor has been contacted with a pharmacological agent. In embodiments, the method further includes monitoring the disease state of an individual. In embodiments, monitoring the disease state of an individual includes comparing the plurality of detected targets in the tumor cell to a reference cell. In embodiments, monitoring the disease state of an individual includes comparing the plurality of detected targets in the tumor cell to a plurality of detected targets in a normal cell. In embodiments, monitoring the disease state of an individual includes comparing the plurality of detected targets in the tumor cell to a plurality of detected targets in a normal cell over a period of time. In embodiments, the comparison is performed over a period of days, weeks, months, or years.

In embodiments, the GBM tumor includes one or more of the following: astrocytes, neurons, oligodendrocytes, oligodendrocyte progenitor cells, neural stem cells, microglia, monocyte-derived macrophages, tumor-associated macrophages (TAMs), neutrophils, tumor-infiltrating T cells, cytomegalovirus, herpes simplex virus, and/or Epstein-Barr virus. In embodiments, the GBM tumor cell includes a gene involved in extracellular matrix regulation (see, e.g., Klemm F et al. Cell. 2020; 181(7): 1643-1660), e.g., FN1, VCAN, THBS1, TGFB1, LGALS3, and/or ANGPTL4. In embodiments, the GMB tumor cell includes a gene involved in pro-tumorigenic macrophage polarization and inhibition of T cell activation, e.g., ANXA1 and/or GPNMB. In embodiments, the GBM tumor cell includes a microglial marker, e.g., P2RY12, TMEM119, SALL1, AHR, and/or VDR. In embodiments, the GBM tumor cell, includes a microglial homeostatic gene, e.g., CX3CR1, TMEM119, CSF1R, P2RY12, P2RY13, SELPLG, GLUT5, CD64, HLA-DR, TREM2, APOE, GPR56 and/or MARCKS. In embodiments, one or more of these genes comprises a mutation. In embodiments, the expression of one or more of these genes is altered (e.g., increased), relative to a normal control cell. In embodiments, the GBM tumor is classified based on isocitrate dehydrogenase (IDH) status (e.g., wild-type or mutant) and/or O6-methylguanine-DNA methyltransferase (MGMT) methylation status.

In embodiments, extending the 3' end of the oligonucleotide primer along the target nucleic acid to generate a complementary sequence includes extending the oligonucleotide primer by using a polymerase. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g., Therminator γ, 9°N polymerase (exo-), Therminator II, Therminator III, or Therminator IX). In embodiments, the DNA polymerase is a thermophilic nucleic acid polymerase. In embodiments, the polymerase is a bacterial DNA polymerase, eukaryotic DNA polymerase, archaeal DNA polymerase, viral DNA polymerase, or phage DNA polymerases. Bacterial DNA polymerases include *E. coli* DNA polymerases I, II and III, IV and V, the Klenow fragment of *E. coli* DNA polymerase, *Clostridium stercorarium* (Cst) DNA polymerase, *Clostridium thermocellum* (Cth) DNA polymerase and *Sulfolobus solfataricus* (Sso) DNA polymerase. Eukaryotic DNA polymerases include DNA polymerases α, β, γ, δ, ε, η, ζ, λ, σ, μ, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as *Thermus aquaticus* (Taq) DNA polymerase, *Thermus filiformis* (Tfi) DNA polymerase, *Thermococcus zilligi* (Tzi) DNA polymerase, *Thermus thermophilus* (Tth) DNA polymerase, *Thermus flavusu* (Tfl) DNA polymerase, *Pyrococcus woesei* (Pwo) DNA polymerase, *Pyrococcus furiosus* (Pfu) DNA polymerase and Turbo Pfu DNA polymerase, *Thermococcus litoralis* (Tli) DNA polymerase, *Pyrococcus* sp. GB-D polymerase, *Thermotoga maritima* (Tma) DNA polymerase, *Bacillus stearothermophilus* (Bst) DNA polymerase, *Pyrococcus Kodakaraensis* (KOD) DNA polymerase, Pfx DNA polymerase, *Thermococcus* sp. JDF-3 (JDF-3) DNA polymerase, *Thermococcus gorgonarius* (Tgo) DNA polymerase, *Thermococcus acidophilium* DNA polymerase; *Sulfolobus acidocaldarius* DNA polymerase; *Thermococcus* sp. go N-7 DNA polymerase; *Pyrodictium occultum* DNA polymerase; *Methanococcus voltae* DNA polymerase; *Methanococcus thermoautotrophicum* DNA polymerase; *Methanococcus jannaschii* DNA polymerase; *Desulfurococcus* strain TOK DNA polymerase (D. Tok Pol); *Pyrococcus abyssi* DNA polymerase; *Pyrococcus horikoshii* DNA polymerase; *Pyrococcus islandicum* DNA polymerase; *Thermococcus fumicolans* DNA polymerase; *Aeropyrum pernix* DNA polymerase; and the heterodimeric DNA polymerase DP1/DP2. In embodiments, the polymerase is 3PDX polymerase as disclosed in U.S. Pat. No. 8,703,461, the disclosure of which is incorporated herein by reference. In embodiments, the polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase. In embodiments, the polymerase is a *Thermus thermophilus* (Tth) DNA polymerase or mutant thereof. In embodiments, the polymerase is a Reverse Transcription Xenopolymerase (RTX).

In embodiments, the target nucleic acid can include any nucleic acid of interest. The nucleic acid can include DNA, RNA, peptide nucleic acid, morpholino nucleic acid, locked nucleic acid, glycol nucleic acid, threose nucleic acid, mixtures thereof, and hybrids thereof. In embodiments, the nucleic acid is obtained from one or more source organisms. In some embodiments, the nucleic acid can include a selected sequence or a portion of a larger sequence. In embodiments, sequencing a portion of a nucleic acid or a fragment thereof can be used to identify the source of the nucleic acid. With reference to nucleic acids, polynucleotides and/or nucleotide sequences a "portion," "fragment" or "region" can be at least 5 consecutive nucleotides, at least 10 consecutive nucleotides, at least 15 consecutive nucleotides, at least 20 consecutive nucleotides, at least 25 consecutive nucleotides, at least 50 consecutive nucleotides, at least 100 consecutive nucleotides, or at least 150 consecutive nucleotides.

In embodiments, the entire sequence of the target is about 1 to 3 kb, and only a portion of that target (e.g., 50 to 100 nucleotides) is sequenced. In embodiments, the target is about 1 to 3 kb. In embodiments, the target is about 1 to 2 kb. In embodiments, the target is about 1 kb. In embodiments, the target is about 2 kb. In embodiments, the target is less than 1 kb. In embodiments, the target is about 500 nucleotides. In embodiments, the target is about 200 nucleotides. In embodiments, the target is about 100 nucleotides. In embodiments, the target is less than 100 nucleotides. In embodiments, the target is about 5 to 50 nucleotides.

In embodiments the target is an RNA transcript. In embodiments the target is a single stranded RNA nucleic acid sequence. In embodiments, the target is an RNA nucleic acid sequence or a DNA nucleic acid sequence (e.g., cDNA). In embodiments, the target is a cDNA target nucleic acid sequence and before step i), the RNA nucleic acid sequence is reverse transcribed to generate the cDNA target nucleic acid sequence. In embodiments, reverse transcription of the RNA nucleic acid is performed with a reverse transcriptase, for example, Tth DNA polymerase or mutants thereof. In embodiments, the target is genomic DNA (gDNA), mitochondrial DNA, chloroplast DNA, episomal DNA, viral DNA, or copy DNA (cDNA). In embodiments, the target is coding RNA such as messenger RNA (mRNA), and non-coding RNA (ncRNA) such as transfer RNA (tRNA), microRNA (miRNA), small nuclear RNA (snRNA), or ribosomal RNA (rRNA). In embodiments, the target is a cancer-associated gene. In embodiments, to minimize amplification errors or bias, the target is not reverse transcribed to generate cDNA.

In embodiments, the target is an RNA nucleic acid sequence or DNA nucleic acid sequence. In embodiments, the target is an RNA nucleic acid sequence or DNA nucleic acid sequence from the same cell. In embodiments, the target is an RNA nucleic acid sequence. In embodiments, the RNA nucleic acid sequence is stabilized using known techniques in the art. For example, RNA degradation by RNase should be minimized using commercially available solutions, e.g., RNA Later®, RNA Lysis Buffer, or Keratinocyte serum-free medium). In embodiments, the target is messenger RNA (mRNA), transfer RNA (tRNA), micro RNA (miRNA), small interfering RNA (siRNA), small nucleolar RNA (snoRNA), small nuclear RNA (snRNA), Piwi-interacting RNA (piRNA), enhancer RNA (eRNA), or ribosomal RNA (rRNA). In embodiments, the target is pre-mRNA. In embodiments, the target is heterogeneous nuclear RNA (hnRNA). In embodiments, the target is mRNA, tRNA (transfer RNA), rRNA (ribosomal RNA), or noncoding RNA (such as lncRNA (long noncoding RNA)). In embodiments, the targets are on different regions of the same RNA nucleic acid sequence. In embodiments, the targets are cDNA target nucleic acid sequences and before step i), the RNA nucleic acid sequences are reverse transcribed to generate the cDNA target nucleic acid sequences. In embodiments, reverse transcription of the RNA nucleic acid is performed with a reverse transcriptase, for example, Tth DNA polymerase or mutants thereof. In embodiments, the targets are not reverse transcribed to cDNA, i.e., the oligonucleotide primer is hybridized directly to the target nucleic acid.

In embodiments, the methods and compositions described herein are utilized to analyze the various sequences of TCRs and BCRs from immune cells, for example various clonotypes. In embodiments, the target nucleic acid includes a nucleic acid sequence encoding a TCR alpha chain, a TCR beta chain, a TCR delta chain, a TCR gamma chain, or any fragment thereof (e.g., variable regions including VDJ or VJ regions, constant regions, transmembrane regions, fragments thereof, combinations thereof, and combinations of fragments thereof). In embodiments, the target nucleic acid includes a nucleic acid sequence encoding a B cell receptor heavy chain, B cell receptor light chain, or any fragment thereof (e.g., variable regions including VDJ or VJ regions, constant regions, transmembrane regions, fragments thereof, combinations thereof, and combinations of fragments thereof). In embodiments, the target nucleic acid includes a CDR3 nucleic acid sequence. In embodiments, the target nucleic acid includes a TCRA gene sequence or a TCRB gene sequence. In embodiments, the target nucleic acid includes a TCRA gene sequence and a TCRB gene sequence. In embodiments, the target nucleic acid includes sequences of various T cell receptor alpha variable genes (TRAV genes), T cell receptor alpha joining genes (TRAJ genes), T cell receptor alpha constant genes (TRAC genes), T cell receptor beta variable genes (TRBV genes), T cell receptor beta diversity genes (TRBD genes), T cell receptor beta joining genes (TRBJ genes), T cell receptor beta constant genes (TRBC genes), T cell receptor gamma variable genes (TRGV genes), T cell receptor gamma joining genes (TRGJ genes), T cell receptor gamma constant genes (TRGC genes), T cell receptor delta variable genes (TRDV genes), T cell receptor delta diversity genes (TRDD genes), T cell receptor delta joining genes (TRDJ genes), or T cell receptor delta constant genes (TRDC genes).

RNA, including mRNA, is highly susceptible to degradation upon exposure to one or more RNAses. RNAses are present in a wide range of locations, including water, many reagents, laboratory equipment and surfaces, skin, and mucous membranes. Working with RNA often requires preparing an RNAse-free environment and materials, as well as taking precautions to avoid introducing RNAses into an RNAse-free environment. These precautions include, but are not limited to, cleaning surfaces with an RNAse cleaning product (e.g., RNASEZAP™ and other commercially available products or 0.5% sodium dodecyl sulfate [SDS] followed by 3% $H_2O_2$); using a designated workspace, materials, and equipment (e.g., pipets, pipet tips); using barrier tips; baking designated glassware (e.g., 300° C. for 2 hours) prior to use; treating enzymes, reagents, and other solutions (e.g., with diethyl pyrocarbonate [DEPC] or dimethyl pyrocarbonate [DMPC]) or using commercially available, certified RNAse-free water or solutions, or ultrafiltered water (e.g., for Tris-based solutions); including an RNAse inhibitor while avoiding temperatures or denaturing conditions that could deactivate the inhibitor; and wearing clean gloves (while avoiding contaminated surfaces) and a clean lab coat.

In embodiments, the cell forms part of a tissue in situ. In embodiments, the cell is an isolated single cell. In embodiments, the cell is a prokaryotic cell. In embodiments, the cell is a eukaryotic cell. In embodiments, the cell is a bacterial cell (e.g., a bacterial cell or bacterial spore), a fungal cell (e.g., a fungal spore), a plant cell, or a mammalian cell. In embodiments, the cell is a stem cell. In embodiments, the stem cell is an embryonic stem cell, a tissue-specific stem cell, a mesenchymal stem cell, or an induced pluripotent stem cell. In embodiments, the cell is an endothelial cell, muscle cell, myocardial, smooth muscle cell, skeletal muscle cell, mesenchymal cell, epithelial cell; hematopoietic cell, such as lymphocytes, including T cell, e.g., (Th1 T cell, Th2 T cell, ThO T cell, cytotoxic T cell); B cell, pre-B cell; monocytes; dendritic cell; neutrophils; or a macrophage. In embodiments, the cell is a stem cell, an immune cell, a cancer cell (e.g., a circulating tumor cell or cancer stem cell), a viral-host cell, or a cell that selectively binds to a desired target. In embodiments, the cell includes a T cell receptor gene sequence, a B cell receptor gene sequence, or an immunoglobulin gene sequence. In embodiments, the cell includes a Toll-like receptor (TLR) gene sequence. In embodiments, the cell includes a gene sequence corresponding to an immunoglobulin light chain polypeptide and a gene sequence corresponding to an immunoglobulin heavy chain polypeptide. In embodiments, the cell is a genetically modified cell. In embodiments, the cell is a circulating tumor cell or cancer stem cell.

In embodiments, the cell is a prokaryotic cell. In embodiments, the cell is a bacterial cell. In embodiments, the bacterial cell is a *Bacteroides, Clostridium, Faecalibacterium, Eubacterium, Ruminococcus, Peptococcus, Peptostreptococcus*, or *Bifidobacterium* cell. In embodiments, the bacterial cell is a *Bacteroides fragilis, Bacteroides melaninogenicus, Bacteroides oralis, Enterococcus faecalis, Escherichia coli, Enterobacter* sp., *Klebsiella* sp., *Bifidobacterium bifidum, Staphylococcus aureus, Lactobacillus, Clostridium perfringens, Proteus mirabilis, Clostridium tetani, Clostridium septicum, Pseudomonas aeruginosa, Salmonella enterica, Faecalibacterium prausnitzii, Peptostreptococcus* sp., or *Peptococcus* sp. cell. In embodiments, the cell is a fungal cell. In embodiments, the fungal cell is a *Candida, Saccharomyces, Aspergillus, Penicillium, Rhodotorula, Trametes, Pleospora, Sclerotinia, Bullera*, or a *Galactomyces* cell.

In embodiments, the cell is a viral-host cell. A "viral-host cell" is used in accordance with its ordinary meaning in virology and refers to a cell that is infected with a viral genome (e.g., viral DNA or viral RNA). The cell, prior to infection with a viral genome, can be any cell that is susceptible to viral entry. In embodiments, the viral-host cell is a lytic viral-host cell. In embodiments, the viral-host cell is capable of producing viral protein. In embodiments, the viral-host cell is a lysogenic viral-host cell. In embodiments, the cell is a viral-host cell including a viral nucleic acid sequence, wherein the viral nucleic acid sequence is from a Hepadnaviridae, Adenoviridae, Herpesviridae, Poxviridae, Parvoviridae, Reoviridae, Coronaviridae, Retroviridae virus.

In embodiments, the cell is an adherent cell (e.g., epithelial cell, endothelial cell, or neural cell). Adherent cells are usually derived from tissues of organs and attach to a substrate (e.g., epithelial cells adhere to an extracellular matrix coated substrate via transmembrane adhesion protein complexes). Adherent cells typically require a substrate, e.g., tissue culture plastic, which may be coated with extracellular matrix (e.g., collagen and laminin) components to increase adhesion properties and provide other signals needed for growth and differentiation. In embodiments, the cell is a neuronal cell, an endothelial cell, epithelial cell, germ cell, plasma cell, a muscle cell, peripheral blood mononuclear cell (PBMC), a myocardial cell, or a retina cell. In embodiments, the cell is a suspension cell (e.g., a cell free-floating in the culture medium, such a lymphoblast or hepatocyte). In embodiments, the cell is a glial cell (e.g., astrocyte, radial glia), pericyte, or stem cell (e.g., a neural stem cell). In embodiments, the cell is a neuronal cell. In embodiments, the cell is an endothelial cell. In embodiments, the cell is an epithelial cell. In embodiments, the cell is a germ cell. In embodiments, the cell is a plasma cell. In embodiments, the cell is a muscle cell. In embodiments, the cell is a peripheral blood mononuclear cell (PBMC). In embodiments, the cell is a myocardial cell. In embodiments, the cell is a retina cell. In embodiments, the cell is a lymphoblast. In embodiments, the cell is a hepatocyte. In embodiments, the cell is a glial cell. In embodiments, the cell is an astrocyte. In embodiments, the cell is a radial glia. In embodiments, the cell is a pericyte. In embodiments, the cell is a stem cell. In embodiments, the cell is a neural stem cell.

In embodiments, the cell is bound to a known antigen. In embodiments, the cell is a cell that selectively binds to a desired target, wherein the target is an antibody, or antigen binding fragment, an aptamer, affimer, non-immunoglobulin scaffold, small molecule, or genetic modifying agent. In embodiments, the cell is a leukocyte (i.e., a white-blood cell). In embodiments, leukocyte is a granulocyte (neutrophil, eosinophil, or basophil), monocyte, or lymphocyte (T cells and B cells). In embodiments, the cell is a lymphocyte. In embodiments, the cell is a T cell, an NK cell, or a B cell.

In embodiments, the cell is an immune cell. In embodiments, the immune cell is a granulocyte, a mast cell, a monocyte, a neutrophil, a dendritic cell, or a natural killer (NK) cell. In embodiments, the immune cell is an adaptive cell, such as a T cell, NK cell, or a B cell. In embodiments, the cell includes a T cell receptor gene sequence, a B cell receptor gene sequence, or an immunoglobulin gene sequence. In embodiments, the immune cell is a granulocyte. In embodiments, the immune cell is a mast cell. In embodiments, the immune cell is a monocyte. In embodiments, the immune cell is a neutrophil. In embodiments, the immune cell is a dendritic cell. In embodiments, the immune cell is a natural killer (NK) cell. In embodiments, the immune cell is a T cell. In embodiments, the immune cell is a B cell. In embodiments, the cell includes a T cell receptor gene sequence. In embodiments, the cell includes a B cell receptor gene sequence. In embodiments, the cell includes an immunoglobulin gene sequence. In embodiments, the plurality of target nucleic acids includes non-contiguous regions of a nucleic acid molecule. In embodiments, the non-contiguous regions include regions of a VDJ recombination of a B cell or T cell.

In embodiments, the cell is a cancer cell. In embodiments, the cancer is lung cancer, colorectal cancer, skin cancer, colon cancer, pancreatic cancer, breast cancer, cervical cancer, lymphoma, leukemia, or a cancer associated with aberrant K-Ras, aberrant APC, aberrant Smad4, aberrant p53, or aberrant TGFβ. In embodiments, the cancer cell includes a ERBB2, KRAS, TP53, PIK3CA, or FGFR2 gene. In embodiments, the cancer cell includes a HER2 gene (see for example FIG. 6). In embodiments, the cancer cell includes a cancer-associated gene (e.g., an oncogene associated with kinases and genes involved in DNA repair) or a cancer-associated biomarker. A "biomarker" is a substance that is associated with a particular characteristic, such as a disease or condition. A change in the levels of a biomarker may correlate with the risk or progression of a disease or with the susceptibility of the disease to a given treatment. In embodiments, the cancer is Acute Myeloid Leukemia, Adrenocortical Carcinoma, Bladder Urothelial Carcinoma, Breast Ductal Carcinoma, Breast Lobular Carcinoma, Cervical Carcinoma, Cholangiocarcinoma, Colorectal Adenocarcinoma, Esophageal Carcinoma, Gastric Adenocarcinoma, Glioblastoma Multiforme, Head and Neck Squamous Cell Carcinoma, Hepatocellular Carcinoma, Kidney Chromophobe Carcinoma, Kidney Clear Cell Carcinoma, Kidney Papillary Cell Carcinoma, Lower Grade Glioma, Lung Adenocarcinoma, Lung Squamous Cell Carcinoma, Mesothelioma, Ovarian Serous Adenocarcinoma, Pancreatic Ductal Adenocarcinoma, Paraganglioma & Pheochromocytoma, Prostate Adenocarcinoma, Sarcoma, Skin Cutaneous Melanoma, Testicular Germ Cell Cancer, Thymoma, Thyroid Papillary Carcinoma, Uterine Carcinosarcoma, Uterine Corpus Endometrioid Carcinoma, or Uveal Melanoma. In embodiments, the cancer-associated gene is a nucleic acid sequence identified within The Cancer Genome Atlas Program, accessible at www.cancer.gov/tcga.

In embodiments, the cancer-associated biomarker is MDC, NME-2, KGF, PlGF, Flt-3L, HGF, MCP1, SAT-1, MIP-1-b, GCLM, OPG, TNF RII, VEGF-D, ITAC, MMP-10, GPI, PPP2R4, AKR1B1, Amy1A, MIP-1b, P-Cadherin, or EPO. In embodiments, the cancer-associated gene is a AKT1, AKT2, AKT3, ALK, AR, ARAF, ARID1A, ATM, ATR, ATRX, AXL, BAP1, BRAF, BRCA1, BRCA2, BTK, CBL, CCND1, CCND2, CCND3, CCNE1, CDK12, CDK2, CDK4, CDK6, CDKN1B, CDKN2A, CDKN2B, CHEK1, CHEK2, CREBBP, CSF1R, CTNNB1, DDR2, EGFR, ERBB2, ERBB3, ERBB4, ERCC2, ERG, ESR1, ETV1, ETV4, ETV5, EZH2, FANCA, FANCD2, FANCI, FBXW7, FGF19, FGF3, FGFR1, FGFR2, FGFR3, FGFR4, FGR, FLT3, FOXL2, GATA2, GNA11, GNAQ, GNAS, H3F3A, HIST1H3B, HNF1A, HRAS, IDH1, IDH2, IGF1R, JAK1, JAK2, JAK3, KDR, KIT, KNSTRN, KRAS, MAGOH, MAP2K1, MAP2K2, MAP2K4, MAPK1, MAX, MDM2, MDM4, MED12, MET, MLH1, MRE11A, MSH2, MSH6, MTOR, MYB, MYBL1, MYC, MYCL, MYCN, MYD88, NBN, NF1, NF2, NFE2L2, NOTCH1, NOTCH2, NOTCH3, NOTCH4, NRAS, NRG1, NTRK1, NTRK2, NTRK3, NUTM1, PALB2, PDGFRA, PDGFRB, PIK3CA, PIK3CB, PIK3R1, PMS2, POLE, PPARG, PPP2R1A, PRKACA, PRKACB, PTCH1, PTEN, PTPN11, RAC1, RAD50, RAD51, RAD51B, RAD51C, RAD51D, RAF1, RB1, RELA, RET, RHEB, RHOA, RICTOR, RNF43, ROS1, RSPO2, RSPO3, SETD2, SF3B1, SLX4, SMAD4, SMARCA4, SMARCB1, SMO, SPOP, SRC, STAT3, STK11, TERT, TOP1, TP53, TSC1, TSC2, U2AF1, or XPO1 gene. In embodiments, the cancer-associated gene is a ABL1, AKT1, ALK, APC, ATM, BRAF, CDH1, CDKN2A, CSF1R, CTNNB1, EGFR, ERBB2, ERBB4, EZH2, FBXW7, FGFR1, FGFR2, FGFR3, FLT3, GNA11, GNAQ, GNAS, HNF1A, HRAS, IDHL IDH2, JAK2, JAK3, KDR, KIT, KRAS, MET, MLH1, MPL, NOTCH1, NPM1, NRAS, PDGFRA, PIK3CA, PTEN, PTPN11, RB1, RET, SMAD4, SMARCB1, SMO, SRC, STK11, TP53, or VHL gene. In embodiments, the cell is a cell (e.g., a T cell) within a tumor. In embodiments, the cell is a non-allogenic cell (i.e., native cell to the subject) within a tumor. In embodiments, the cell is a tumor infiltrating lymphocyte (TIL). In embodiments, the cell is an allogenic cell. In embodiments, the cell is a circulating tumor cell.

In embodiments, the cell in situ is obtained from a subject (e.g., human or animal tissue). Once obtained, the cell is placed in an artificial environment in plastic or glass containers supported with specialized medium containing essential nutrients and growth factors to support proliferation. In embodiments, the cell is permeabilized and immobilized to a solid support surface. In embodiments, the cell is permeabilized and immobilized to an array (i.e., to discrete locations arranged in an array). In embodiments, the cell is immobilized to a solid support surface. In embodiments, the surface includes a patterned surface (e.g., suitable for immobilization of a plurality of cells in an ordered pattern. The discrete regions of the ordered pattern may have defined locations in a regular array, which may correspond to a rectilinear pattern, circular pattern, hexagonal pattern, or the like. These discrete regions are separated by interstitial regions. As used herein, the term "interstitial region" refers to an area in a substrate or on a surface that separates other areas of the substrate or surface. In embodiments, a plurality of cells are immobilized on a patterned surface that have a mean or median separation from one another of about 10-20 µm. In embodiments, a plurality of cells are immobilized on a patterned surface that have a mean or median separation from one another of about 10-20; 10-50; or 100 µm. In embodiments, a plurality of cells are arrayed on a substrate. In embodiments, a plurality of cells are immobilized in a 96-well microplate having a mean or median well-to-well spacing of about 8 mm to about 12 mm (e.g., about 9 mm). In embodiments, a plurality of cells are immobilized in a 384-well microplate having a mean or median well-to-well spacing of about 3 mm to about 6 mm (e.g., about 4.5 mm).

In embodiments, the cell is attached to the substrate via a bioconjugate reactive linker. In embodiments, the cell is attached to the substrate via a specific binding reagent. In embodiments, the specific binding reagent includes an antibody, single-chain Fv fragment (scFv), antibody fragment-antigen binding (Fab), or an aptamer. In embodiments, the specific binding reagent includes an antibody, or antigen binding fragment, an aptamer, affimer, or non-immunoglobulin scaffold. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. Substrates may be prepared for selective capture of particular cells. For example, a substrate containing a plurality of bioconjugate reactive moieties or a plurality of specific binding reagents, optionally in an ordered pattern, contacts a plurality of cells. Only cells containing complementary bioconjugate reactive moieties or complementary specific binding reagents are capable of reacting, and thus adhering, to the substrate.

In embodiments, the methods are performed in situ on isolated cells or in tissue sections that have been prepared according to methodologies known in the art. Methods for permeabilization and fixation of cells and tissue samples are known in the art, as exemplified by Cremer et al., The Nucleus: Volume 1: Nuclei and Subnuclear Components, R. Hancock (ed.) 2008; and Larsson et al., Nat. Methods (2010) 7:395-397, the content of each of which is incorporated herein by reference in its entirety. In embodiments, the cell is cleared (e.g., digested) of proteins, lipids, or proteins and lipids.

In embodiments, the cell is immobilized to a substrate. The cell may have been cultured on the surface, or the cell may have been initially cultured in suspension and then fixed to the surface. Substrates can be two- or three-dimensional and can include a planar surface (e.g., a glass slide). A substrate can include glass (e.g., controlled pore glass (CPG)), quartz, plastic (such as polystyrene (low cross-linked and high cross-linked polystyrene), polycarbonate, polypropylene and poly(methymethacrylate)), acrylic copolymer, polyamide, silicon, metal (e.g., alkanethiolate-derivatized gold), cellulose, nylon, latex, dextran, gel matrix (e.g., silica gel), polyacrolein, or composites. In embodiments, the substrate includes a polymeric coating, optionally containing bioconjugate reactive moieties capable of affixing the sample. Suitable three-dimensional substrates include, for example, spheres, microparticles, beads, membranes, slides, plates, micromachined chips, tubes (e.g., capillary tubes), microwells, microfluidic devices, channels, filters, or any other structure suitable for anchoring a sample. In embodiments, the substrate is not a flow cell. In embodiments, the substrate includes a polymer matrix material (e.g., polyacrylamide, cellulose, alginate, polyamide, cross-linked agarose, cross-linked dextran or cross-linked polyethylene glycol), which may be referred to herein as a "matrix", "synthetic matrix", "exogenous polymer" or "exogenous hydrogel". In embodiments, a matrix may refer to the various components and organelles of a cell, for example, the cytoskeleton (e.g., actin and tubulin), endoplasmic reticulum, Golgi apparatus, vesicles, etc. In embodiments, the matrix is endogenous to a cell. In embodiments, the matrix is exogenous to a cell. In embodiments, the matrix includes both the intracellular and extracellular components of a cell. In embodiments, polynucleotide primers may be immobilized on a matrix including the various components and organelles of a cell. Immobilization of polynucleotide primers on a matrix of cellular components and organelles of a cell is accomplished as described herein, for example, through the interaction/reaction of complementary bioconjugate reactive moieties. In embodiments, the exogenous polymer may be a matrix or a network of extracellular components that act as a point of attachment (e.g., act as an anchor) for the cell to a substrate."

In embodiments, the cell is exposed to paraformaldehyde (i.e., by contacting the cell with paraformaldehyde). Any suitable permeabilization and fixation technologies can be used for making the cell available for the detection methods provided herein. In embodiments the method includes affixing single cells or tissues to a transparent substrate. Exemplary tissue include those from skin tissue, muscle tissue, bone tissue, organ tissue and the like. In embodiments, the method includes immobilizing the cell in situ to a substrate and permeabilized for delivering probes, enzymes, nucleotides and other components required in the reactions. In embodiments, the cell includes many cells from a tissue section in which the original spatial relationships of the cells are retained. In embodiments, the cell in situ is within a Formalin-Fixed Paraffin-Embedded (FFPE) sample. In embodiments, the cell is subjected to paraffin removal methods, such as methods involving incubation with a hydrocarbon solvent, such as xylene or hexane, followed by two or more washes with decreasing concentrations of an alcohol, such as ethanol. The cell may be rehydrated in a buffer, such as PBS, TBS or MOPs. In embodiments, the FFPE sample is incubated with xylene and washed using ethanol to remove the embedding wax, followed by treatment with Proteinase K to permeabilized the tissue. In embodiments, the cell is fixed with a chemical fixing agent. In embodiments, the chemical fixing agent is formaldehyde or glutaraldehyde. In embodiments, the chemical fixing agent is glyoxal or dioxolane. In embodiments, the chemical fixing agent includes one or more of ethanol, methanol, 2-propanol, acetone, and glyoxal. In embodiments, the chemical fixing agent includes formalin, Greenfix®, Greenfix® Plus, UPM, CyMol®, HOPE®, CytoSkelFix™, F-Solv®, FineFIX®, RCL2/KINFix, UMFIX, Glyo-Fixx®, Histochoice®, or PAXgene®. In embodiments, the cell is fixed within a synthetic three-dimensional matrix (e.g., polymeric material). In embodiments, the synthetic matrix includes polymeric-crosslinking material. In embodiments, the material includes polyacrylamide, poly-ethylene glycol (PEG), poly(acrylate-co-acrylic acid) (PAA), or Poly(N-isopropylacrylamide) (NIPAM).

In embodiments the cell is lysed to release nucleic acid or other materials from the cells. For example, the cells may be lysed using reagents (e.g., a surfactant such as Triton-X or SDS, an enzyme such as lysozyme, lysostaphin, zymolase, cellulase, mutanolysin, glycanases, proteases, mannase, proteinase K, etc.) or a physical lysing mechanism a physical condition (e.g., ultrasound, ultraviolet light, mechanical agitation, etc.). The cells may release, for instance, DNA, RNA, mRNA, proteins, or enzymes. The cells may arise from any suitable source. For instance, the cells may be any cells for which nucleic acid from the cells is desired to be studied or sequenced, etc., and may include one, or more than one, cell type. The cells may be for example, from a specific population of cells, such as from a certain organ or tissue (e.g., cardiac cells, immune cells, muscle cells, cancer cells, etc.), cells from a specific individual or species (e.g., human cells, mouse cells, bacteria, etc.), cells from different organisms, cells from a naturally-occurring sample (e.g., pond water, soil, etc.), or the like. In some cases, the cells may be dissociated from tissue. In embodiments, the method does not include dissociating the cell from the tissue or the cellular microenvironment. In embodiments, the method does not include lysing the cell.

In embodiments, the method further includes subjecting the cell to expansion microscopy methods and techniques. Expansion allows individual targets (e.g., mRNA or RNA transcripts) which are densely packed within a cell, to be resolved spatially in a high-throughput manner. Expansion microscopy techniques are known in the art and can be performed as described in US 2016/0116384 and Chen et al., Science, 347, 543 (2015), each of which are incorporated herein by reference in their entirety.

In embodiments, the method does not include subjecting the cell to expansion microscopy. Typically, expansion microscopy techniques utilize a swellable polymer or hydrogel (e.g., a synthetic matrix-forming material) which can significantly slow diffusion of enzymes and nucleotides. Matrix (e.g., synthetic matrix) forming materials include polyacrylamide, cellulose, alginate, polyamide, cross-linked agarose, cross-linked dextran or cross-linked polyethylene glycol. The matrix forming materials can form a matrix by polymerization and/or crosslinking of the matrix forming materials using methods specific for the matrix forming materials and methods, reagents and conditions known to those of skill in the art. Additionally, expansion microscopy techniques may render the temperature of the cell sample difficult to modulate in a uniform, controlled manner. Modulating temperature provides a useful parameter to optimize amplification and sequencing methods. In embodiments, the method does not include an exogenous matrix.

In embodiments, the oligonucleotide primer is about 50 to about 500 nucleotides in length. In embodiments, the oligonucleotide primer is about 50 to about 300 nucleotides in length. In embodiments, the oligonucleotide primer is about 80 to about 300 nucleotides in length. In embodiments, the oligonucleotide primer is about 50 to about 150 nucleotides in length. In embodiments, the oligonucleotide primer is about or more than about 40, 50, 75, 100, 125, 150, 175, 200, 250, 300, 350, 400, or 500 nucleotides in length. In embodiments, the oligonucleotide primer is less than about 50, 75, 100, 125, 150, 175, 200, 250, 300, 350, 400, or 500 nucleotides in length.

In embodiments, the oligonucleotide primer is a single-stranded polynucleotide having at least one primer binding sequence. In embodiments, the oligonucleotide primer includes at least one amplification primer binding sequence and at least one sequencing primer binding sequence. In embodiments, the oligonucleotide primer includes at least two primer binding sequences. In embodiments, the oligonucleotide primer includes an amplification primer binding sequence. In embodiments, the oligonucleotide primer includes a sequencing primer binding sequence. The amplification primer binding sequence refers to a nucleotide sequence that is complementary to a primer useful in initiating amplification (i.e., an amplification primer). Likewise, a sequencing primer binding sequence is a nucleotide sequence that is complementary to a primer useful in initiating sequencing (i.e., a sequencing primer). Primer binding sequences usually have a length in the range of between 3 to 36 nucleotides, also 5 to 24 nucleotides, also from 14 to 36 nucleotides. In embodiments, the oligonucleotide primer does not include a barcode. In embodiments, an amplification primer and a sequencing primer are complementary to the same primer binding sequence, or overlapping primer binding sequences. In embodiments, an amplification primer and a sequencing primer are complementary to different primer binding sequences. In embodiments, the primer binding sequence is complementary to a fluorescent in situ hybridization (FISH) probe. FISH probes may be custom designed using known techniques in the art, see for example Gelali, E., Girelli, G., Matsumoto, M. et al. Nat Commun 10, 1636 (2019).

In embodiments, the oligonucleotide primer includes at least one primer binding sequence. In embodiments, the oligonucleotide primer includes at least two primer binding sequences. In embodiments, the oligonucleotide primer includes an amplification primer binding sequence. In embodiments, the oligonucleotide primer includes a sequencing primer binding sequence. The amplification primer binding sequence refers to a nucleotide sequence that is complementary to a primer useful in initiating amplification (i.e., an amplification primer). Likewise, a sequencing primer binding sequence is a nucleotide sequence that is complementary to a primer useful in initiating sequencing (i.e., a sequencing primer). Primer binding sequences usually have a length in the range of between 3 to 36 nucleotides, also 5 to 24 nucleotides, also from 14 to 36 nucleotides. In embodiments, an amplification primer and a sequencing primer are complementary to the same primer binding sequence, or overlapping primer binding sequences. In embodiments, an amplification primer and a sequencing primer are complementary to different primer binding sequences.

In embodiments, the oligonucleotide primer includes a primer binding sequence from a known set of primer binding sequences. In embodiments, the oligonucleotide primer includes at least two primer binding sequences from a known set of primer binding sequences. In embodiments, the oligonucleotide primer includes two or more primer binding sequences from a known set of primer binding sequences. In embodiments, the oligonucleotide primer includes up to 50 different primer binding sequences from a known set of primer binding sequences. In embodiments, the oligonucleotide primer includes up to 10 different primer binding sequences from a known set of primer binding sequences. In embodiments, the oligonucleotide primer includes up to 5 different primer binding sequences from a known set of primer binding sequences. In embodiments, the oligonucleotide primer includes two or more sequencing primer binding sequences from a known set of sequencing primer binding sequences. In embodiments, the oligonucleotide primer includes 1, 2, 3, 4, 5, 6, 7, 8, 9, or 10 primer binding sequences from a known set of primer binding sequences. In embodiments, the oligonucleotide primer includes two or more different primer binding sequences from a known set of primer binding sequences. In embodiments, the oligonucleotide primer includes 1, 2, 3, 4, 5, 6, 7, 8, 9, or 10 different primer binding sequences from a known set of primer binding sequences. In embodiments, the oligonucleotide primer includes 2 to 5 primer binding sequences from a known set of primer binding sequences. In embodiments, the oligonucleotide primer includes 2 to 5 different primer binding sequences from a known set of primer binding sequences. In embodiments, the oligonucleotide primer includes 2 to 5 sequencing primer binding sequences from a known set of sequencing primer binding sequences. In embodiments, the oligonucleotide primer includes 2 to 5 different sequencing primer binding sequences from a known set of sequencing primer binding sequences. In embodiments, the oligonucleotide primer includes at least two different primer binding sequences. In embodiments, the oligonucleotide primer includes two different sequencing primer binding sequences.

In embodiments, the known set of primer binding sequences includes at least 2 different primer binding sequences. In embodiments, the known set of primer binding sequences includes two or more different primer binding sequences. In embodiments, the known set of primer binding sequences includes at least 3 different primer binding sequences. In embodiments, the known set of primer binding sequences includes three or more different primer binding sequences. In embodiments, the known set of primer binding sequences includes at least 2 different sequencing primer binding sequences. In embodiments, the known set of primer binding sequences includes two or more different sequencing primer binding sequences. In embodiments, the known set of primer binding sequences includes 2 to 10 different sequencing primer binding sequences. In embodiments, the known set of primer binding sequences includes 2 to 6 different sequencing primer binding sequences. In embodiments, the known set of primer binding sequences includes 3 to 8 different sequencing primer binding sequences.

The oligonucleotide primer is similar to a padlock probe, however with an important distinction. Typically, padlock probes hybridize to adjacent sequences and are then ligated together to form a circular oligonucleotide. The oligonucleotide primers hybridize to sequences adjacent to the target nucleic acid sequence resulting in a gap (e.g., a gap spanning the length of the target nucleic acid sequence) as observed in FIG. 1B. Padlock probes are specialized ligation probes, examples of which are known in the art, see for example Nilsson M, et al. Science. 1994; 265(5181):2085-2088), and has been applied to detect transcribed RNA in cells, see for example Christian A T, et al. Proc Natl Acad Sci USA. 2001; 98(25):14238-14243, both of which are incorporated herein by reference in their entireties. The construction of the oligonucleotide primer allows for selective targeting, enabling detection of specific targets within the cell.

In embodiments, the oligonucleotide primer is approximately 50 to 200 nucleotides. In embodiments, the oligonucleotide primer has a first domain that is capable of hybridizing to a first target sequence domain, and a second ligation domain, capable of hybridizing to a target nucleic acid sequence-adjacent second sequence domain. In embodiments, following hybridization there is a gap between the first target sequence domain, and the second ligation domain, wherein the gap spans the length of the target nucleic acid sequence. In embodiments, the oligonucleotide primer has a first domain that is capable of hybridizing to a first target sequence domain, and a second domain capable of hybridizing to a second target sequence domain. In embodiments, the length of the first domain and second domain are the same length (e.g., both the first and the second domains are about 15 nucleotides). In embodiments, the length of the first domain and second domain are different lengths (e.g., the first domain is about 10 nucleotides and the second domain is about 20 nucleotides). In embodiments, an asymmetric oligonucleotide primer (i.e., an oligonucleotide primer having a first domain and second domain that are different sequence lengths) may be advantageous in preventing non-specific hybridization. In embodiments, the total length of the first domain and second domain is about 25, 30, 35, or 40 nucleotides. In embodiments, the total length of the first domain and second domain is about 30 nucleotides. In embodiments, the total length of the first domain and second domain is about 15 to 25 nucleotides. In embodiments, the total length of the first domain is about 15 to 25 nucleotides and the total length of the second domain is about 20 to 25 nucleotides.

In embodiments, the oligonucleotide primer contains one or more functional moieties (e.g., bioconjugate reactive groups) that serve as attachment points to the cell (i.e., the internal cellular scaffold) or to the matrix in which the cell is embedded (e.g. a hydrogel). In embodiments, the bioconjugate reactive group is located at the 5' and/or 3' end of the primer. In embodiments, the bioconjugate reactive group is located at an internal position of the primer e.g., the primer contains one or more modified nucleotides, such as amino-allyl deoxyuridine 5'-triphosphate (dUTP) nucleotide(s). In embodiments, the functional moiety can be covalently cross-linked, copolymerize with or otherwise non-covalently bound to the matrix. In embodiments, the functional moiety can react with a cross-linker. In embodiments, the functional moiety can be part of a ligand-ligand binding pair. Suitable exemplary functional moieties include an amine, acrydite, alkyne, biotin, azide, and thiol. In embodiments of cross-linking, the functional moiety is cross-linked to modified dNTP or dUTP or both. In embodiments, suitable exemplary cross-linker reactive groups include imidoester (DMP), succinimide ester (NETS), maleimide (Sulfo-SMCC), carbodiimide (DCC, EDC) and phenyl azide. Cross-linkers within the scope of the present disclosure may include a spacer moiety. In embodiments, such spacer moieties may be functionalized. In embodiments, such spacer moieties may be chemically stable. In embodiments, such spacer moieties may be of sufficient length to allow amplification of the nucleic acid bound to the matrix. In embodiments, suitable exemplary spacer moieties include polyethylene glycol, carbon spacers, photo-cleavable spacers and other spacers known to those of skill in the art and the like. In embodiments, the oligonucleotide primer contains a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, prior to amplification, the modified nucleotide-containing primer is attached to the cell protein matrix by using a cross-linking reagent (e.g., an amine-reactive crosslinking agent with PEG spacers, such as (PEGylated bis(sulfosuccinimidyl)suberate) (BS(PEG)9)).

In embodiments, the oligonucleotide primer includes at least one target-specific region. In embodiments, the oligonucleotide primer includes two target-specific regions. In embodiments, the oligonucleotide primer includes at least one flanking-target region (i.e., an oligonucleotide sequence that flanks the region of interest). In embodiments, the oligonucleotide primer includes two flanking-target regions. A target-specific region is a single stranded polynucleotide that is at least 50% complementary, at least 75% complementary, at least 85% complementary, at least 90% complementary, at least 95% complementary, at least 98%, at least 99% complementary, or 100% complementary to a portion of a nucleic acid molecule that includes a target sequence (e.g., a gene of interest). In embodiments, the target-specific region is capable of hybridizing to at least a portion of the target sequence. In embodiments, the target-specific region is substantially non-complementary to other target sequences present in the sample.

In embodiments, the circular oligonucleotide is about 100 to about 1000 nucleotides in length, about 100 to about 300 nucleotides in length, about 300 to about 500 nucleotides in length, or about 500 to about 1000 nucleotides in length. In embodiments, the circular oligonucleotide includes a plurality of sequencing primer binding sequences. In embodiments, the circular oligonucleotide includes a plurality of different sequencing primer binding sequences. In embodiments, the circular oligonucleotide is about 100 to about 1000 nucleotides in length. In embodiments, the circular oligonucleotide is about 100 to about 300 nucleotides in length. In embodiments, the circular oligonucleotide is about 300 to about 500 nucleotides in length. In embodiments, the circular oligonucleotide is about 500 to about 1000 nucleotides in length. In embodiments, the circular oligonucleotide is about or more than about 100, 150, 200, 250, 300, 350, 400, 500, 750, 1000, or more nucleotides in length.

In embodiments, the method includes circularizing and ligating the complementary sequence to the 5' end of the oligonucleotide primer (e.g., as illustrated in FIGS. 1A-1D). In embodiments, circularizing the oligonucleotide primer to generate a circular oligonucleotide includes extending the 3' end of the oligonucleotide primer (e.g., extending the 3' end of the primer using a polymerase (e.g., a *Thermus thermophilus* (Tth) DNA polymerase) to incorporate one or more nucleotides) along the target nucleic acid to generate a complementary sequence (e.g., complementary to the target nucleic acid, for example a target RNA sequence), and ligating the complementary sequence to the 5' end of the oligonucleotide primer. In embodiments, the ligation includes enzymatic ligation. In embodiments, ligating includes enzymatic ligation including a ligation enzyme (e.g., Circligase enzyme, Taq DNA Ligase, HiFi Taq DNA Ligase, T4 ligase, PBCV-1 DNA Ligase (also known as SplintR ligase) or Ampligase DNA Ligase). Non-limiting examples of ligases include DNA ligases such as DNA Ligase I, DNA Ligase II, DNA Ligase III, DNA Ligase IV, T4 DNA ligase, T7 DNA ligase, T3 DNA Ligase, *E. coli* DNA Ligase, PBCV-1 DNA Ligase (also known as SplintR ligase) or a Taq DNA Ligase. In embodiments, the ligase enzyme includes a T4 DNA ligase, T4 RNA ligase 1, T4 RNA ligase 2, T3 DNA ligase or T7 DNA ligase. In embodiments, the enzymatic ligation is performed by a mixture of ligases. In embodiments, the ligation enzyme is selected from the group consisting of T4 DNA ligase, T4 RNA ligase 1, T4 RNA ligase 2, RtcB ligase, T3 DNA ligase, T7 DNA ligase, Taq DNA ligase, PBCV-1 DNA Ligase, a thermostable DNA ligase (e.g., 5'AppDNA/RNA ligase), an ATP dependent DNA ligase, an RNA-dependent DNA ligase (e.g., SplintR ligase), and combinations thereof.

In embodiments, ligating includes chemical ligation (e.g., enzyme-free, click-mediated ligation). In embodiments, the oligonucleotide primer includes a first bioconjugate reactive moiety capable of bonding upon contact with a second (complementary) bioconjugate reactive moiety. In embodiments, the oligonucleotide primer includes an alkynyl moiety at the 3' and an azide moiety at the 5' end that, upon hybridization to the target nucleic acid react to form a triazole linkage during suitable reaction conditions. Reaction conditions and protocols for chemical ligation techniques that are compatible with nucleic acid amplification methods are known in the art, for example El-Sagheer, A. H., & Brown, T. (2012). *Accounts of chemical research*, 45(8), 1258-1267; Manuguerra I. et al. *Chem Commun (Camb)*. 2018; 54(36):4529-4532; and Odeh, F., et al. (2019). *Molecules* (Basel, Switzerland), 25(1), 3, each of which is incorporated herein by reference in their entirety. In embodiments, the first region of the oligonucleotide primer or the second region of the oligonucleotide primer are, independently, about or more than about 3, 4, 5, 6, 7, 8, 9, 10, 11, 12, 13, 14, 15, 20, or more nucleotides in length. In embodiments, the first region of the oligonucleotide primer or the second region of the oligonucleotide primer are, independently, less than about 3, 4, 5, 6, 7, 8, 9, 10, 11, 12, 13, 14, 15, 20, or more nucleotides in length. In embodiments, the first region of the oligonucleotide primer and the second region of the oligonucleotide primer are the same length. In embodiments, the first region of the oligonucleotide primer and the second region of the oligonucleotide primer are different lengths.

In embodiments, the first region (alternatively referred to as flanking-target-region) of the oligonucleotide primer or the second region (alternatively referred to as flanking-target-region) of the oligonucleotide primer includes about 5 to about 15 nucleotides. In embodiments, the first region (alternatively referred to as flanking-target-region) of the oligonucleotide primer or the second region (alternatively referred to as flanking-target-region) of the oligonucleotide primer includes about 10 to about 25 nucleotides. In embodiments, the first region (alternatively referred to as flanking-target-region) of the oligonucleotide primer or the second region (alternatively referred to as flanking-target-region) of the oligonucleotide primer includes about 10 to about 20 nucleotides. In embodiments, the first region (alternatively referred to as flanking-target-region) of the oligonucleotide primer or the second region (alternatively referred to as flanking-target-region) of the oligonucleotide primer includes about 15 to about 25 nucleotides. In embodiments, the first region of the oligonucleotide primer or the second region of the oligonucleotide primer includes about 3 to about 5 nucleotides. In embodiments, the first region of the oligonucleotide primer includes about 3 to about 5 nucleotides and second region of the oligonucleotide primer includes about 6 to about 10 nucleotides. In embodiments, the first region of the oligonucleotide primer includes about 10 to about 15 nucleotides and the second region of the oligonucleotide primer includes about 15 to about 30 nucleotides. In embodiments, the first region includes at least one target-specific region. In embodiments, the second region includes at least one target-specific region. A target-specific region is a single stranded polynucleotide that is at least 50% complementary, at least 75% complementary, at least 85% complementary, at least 90% complementary, at least 95% complementary, at least 98%, at least 99% complementary, or 100% complementary to a portion of a nucleic acid molecule that includes a target sequence (e.g., a gene of interest). In embodiments, the target-specific region is capable of hybridizing to at least a portion of the target sequence. In embodiments, the target-specific region is substantially non-complementary to other target sequences present in the sample. In embodiments, the length of the first region and second region are the same length (e.g., both the first and the second regions are each about 15 nucleotides). In embodiments, the length of the first region and second region are different lengths (e.g., the first region is about 10 nucleotides and the second region is about 20 nucleotides). In embodiments, an asymmetric oligonucleotide primer (i.e., an oligonucleotide primer having a first region and second region that are different lengths) may be advantageous in preventing non-specific hybridization. In embodiments, the total length of the first region and second region combined is about 25, 30, 35, or 40 nucleotides. In embodiments, the total length of the first domain and second domain is combined about 30 to 40 nucleotides.

In embodiments, the method further includes an amplification method for amplifying the circular polynucleotide. In embodiments, the method further includes amplifying the circular polynucleotide by extending an amplification primer with a polymerase (e.g., a strand-displacing polymerase), wherein the primer extension generates an extension product including multiple complements of the circular polynucleotide, referred to as an amplicon. An amplicon typically contains multiple, tandem copies of the circularized nucleic acid molecule of the corresponding sample nucleic acid. The number of copies can be varied by appropriate modification of the reaction conditions, such as varying the number of amplification cycles, using polymerases of varying processivity in the amplification reaction, or varying the length of time that the amplification reaction is run. In embodiments, the circular polynucleotide is copied about 5-50 times (i.e., the extension product includes about 5 to 50 complements of the circular polynucleotide). In embodiments, the circular polynucleotide is copied about 100-300 times (i.e., the extension product includes about 100 to 300 complements of the circular polynucleotide). In embodiments, the method includes hybridizing an amplification primer and oligonucleotide primer in the same reaction (e.g., simultaneously). In embodiments, the method includes contacting the target with an amplification primer and oligonucleotide primer in the same reaction (e.g., simultaneously).

In embodiments, the method includes subjecting the cell to a polymer comprising a plurality of immobilized oligonucleotide primers (e.g., primers covalently attached to components within the matrix forming polymer). In embodiments, the method includes contacting the cell with a plurality of oligonucleotide primers that are capable of forming a covalent attachment to one or more cellular components; when the oligonucleotide primers form a covalent attachment to a cellular component, they may be referred to as immobilized oligonucleotide primers. In embodiments, the covalent attachment of the oligonucleotide primers to one or more cellular components does not require cross-linking. In embodiments, the attachment of the oligonucleotide primers to one or more cellular components includes hybridization of modified oligonucleotides (e.g., LNA-containing oligonucleotides that provide increased thermal hybridization stability). Non-limiting examples of covalent attachment include amine-modified polynucleotides within the primer reacting with epoxy or isothiocyanate groups within the matrix, succinylated polynucleotides within the primer reacting with aminophenyl or aminopropyl functional groups within the matrix, dibenzocyclooctyne-modified polynucleotides within the primer reacting with azide functional groups within the matrix (or vice versa), trans-cyclooctyne-modified polynucleotides within the primer reacting with tetrazine or methyl tetrazine groups within the matrix (or vice versa), disulfide modified polynucleotides within the primer reacting with mercapto-functional groups within the matrix, amine-functionalized polynucleotides within the primer reacting with carboxylic acid groups within the matrix or cellular component via 1-ethyl-3-(3-dimethylaminopropyl)-carbodiimide hydrochloride (EDC) chemistry, thiol-modified polynucleotides within the primer attaching to the matrix or cellular component via a disulfide bond or maleimide linkage, alkyne-modified polynucleotides within the primer attaching to a matrix via copper-catalyzed click reactions to azide functional groups within the matrix, azide-modified polynucleotides within the primer attaching to the matrix via copper-catalyzed click reactions to alkyne functional groups within the matrix, and acrydite-modified polynucleotides within the primer polymerizing with free acrylic acid monomers within the matrix to form polyacrylamide. In embodiments, the primer is attached to the matrix through electrostatic binding. For example, the negatively charged phosphate backbone of the primer may be bound electrostatically to positively charged monomers in the matrix.

In embodiments, the plurality of oligonucleotide primers form covalent attachments (i.e., bioconjugate linkers) to one or more cellular components through bioconjugate reactive moieties. In embodiments, the 5' end of the primer contains a functional group that is capable of reacting with a complementary group so the primer may be tethered to a cellular component (e.g., a protein). In embodiments, the primers may be used to aid in tethering the extension product to a confined area and may not be extended. In embodiments, the immobilized oligonucleotides include blocking groups at their 3' ends that prevent polymerase extension. A blocking moiety prevents formation of a covalent bond between the 3' hydroxyl moiety of the nucleotide and the 5' phosphate of another nucleotide. In embodiments, the method includes extending the one or more immobilized oligonucleotides hybridized to an extension product with a polymerase. For example, the one or more immobilized oligonucleotides may be used to aid in tethering the extension product to a localized area and may be extended in an exponential RCA amplification reaction. In embodiments, the 5' end of the primer is covalently attached to a cellular component. In embodiments, the 5' end of the primer is covalently attached to the matrix. In embodiments, the 3' end of the primer is covalently attached to a cellular component. In embodiments, the 3' end of the primer is covalently attached to the matrix. The primers can include one or more reactive moieties. As used herein, the term reactive moiety includes any group capable of reacting with another molecule, e.g., a nucleic acid or polypeptide through covalent, non-covalent or other interactions. By way of example, the primer can include an amino acid reactive moiety that reacts with an amino acid on a protein or polypeptide through a covalent, non-covalent or other interaction.

In embodiments, the amplifying includes rolling circle amplification (RCA) or rolling circle transcription (RCT) (see, e.g., Lizardi et al., Nat. Genet. 19:225-232 (1998), which is incorporated herein by reference in its entirety).

Several suitable rolling circle amplification methods are known in the art. For example, RCA amplifies a circular polynucleotide (e.g., DNA) by polymerase extension of an amplification primer complementary to a portion of the template polynucleotide. This process generates copies of the circular polynucleotide template such that multiple complements of the template sequence arranged end to end in tandem are generated (i.e., a concatemer) locally preserved at the site of the circle formation. In embodiments, the amplifying occurs at isothermal conditions. In embodiments, the amplifying includes hybridization chain reaction (HCR). HCR uses a pair of complementary, kinetically trapped hairpin oligomers to propagate a chain reaction of hybridization events, as described in Dirks, R. M., & Pierce, N. A. (2004) PNAS USA, 101(43), 15275-15278, which is incorporated herein by reference for all purposes. In embodiments, the amplifying includes branched rolling circle amplification (BRCA); e.g., as described in Fan T, Mao Y, Sun Q, et al. Cancer Sci. 2018; 109:2897-2906, which is incorporated herein by reference in its entirety. In embodiments, the amplifying includes hyberbranched rolling circle amplification (HRCA). Hyperbranched RCA uses a second primer complementary to the first amplification product. This allows products to be replicated by a strand-displacement mechanism, which yields drastic amplification within an isothermal reaction (Lage et al., Genome Research 13:294-307 (2003), which is incorporated herein by reference in its entirety). In embodiments, amplifying includes polymerase extension of an amplification primer. In embodiments, the polymerase is T4, T7, Sequenase, Taq, Klenow, and Pol I DNA polymerases. SD polymerase, Bst large fragment polymerase, or a phi29 polymerase or mutant thereof. In embodiments, the strand-displacing enzyme is an SD polymerase, Bst large fragment polymerase, or a phi29 polymerase or mutant thereof. In embodiments, the strand-displacing polymerase is phi29 polymerase, phi29 mutant polymerase or a thermostable phi29 mutant polymerase. A "phi polymerase" (or "Φ29 polymerase") is a DNA polymerase from the Φ29 phage or from one of the related phages that, like Φ29, contain a terminal protein used in the initiation of DNA replication. For example, phi29 polymerases include the B103, GA-1, PZA, Φ15, BS32, M2Y (also known as M2), Nf, G1, Cp-1, PRD1, PZE, SFS, Cp-5, Cp-7, PR4, PR5, PR722, L17, Φ21, and AV-1 DNA polymerases, as well as chimeras thereof. A phi29 mutant DNA polymerase includes one or more mutations relative to naturally-occurring wild-type phi29 DNA polymerases, for example, one or more mutations that alter interaction with and/or incorporation of nucleotide analogs, increase stability, increase read length, enhance accuracy, increase photo-tolerance, and/or alter another polymerase property, and can include additional alterations or modifications over the wild-type phi29 DNA polymerase, such as one or more deletions, insertions, and/or fusions of additional peptide or protein sequences. Thermostable phi29 mutant polymerases are known in the art, see for example US 2014/0322759, which is incorporated herein by reference for all purposes. For example, a thermostable phi29 mutant polymerase refers to an isolated bacteriophage phi29 DNA polymerase including at least one mutation selected from the group consisting of M8R, V51A, M97T, L123S, G197D, K209E, E221K, E239G, Q497P, K512E, E515A, and F526 (relative to wild type phi29 polymerase). In embodiments, the polymerase is a phage or bacterial RNA polymerases (RNAPs). In embodiments, the polymerase is a T7 RNA polymerase. In embodiments, the polymerase is an RNA polymerase. Useful RNA polymerases include, but are not limited to, viral RNA polymerases such as T7 RNA polymerase, T3 polymerase, SP6 polymerase, and K11 polymerase; Eukaryotic RNA polymerases such as RNA polymerase I, RNA polymerase II, RNA polymerase III, RNA polymerase IV, and RNA polymerase V; and Archaea RNA polymerase.

In embodiments, the amplification method includes a standard dNTP mixture including dATP, dCTP, dGTP and dTTP (for DNA) or dATP, dCTP, dGTP and dUTP (for RNA). In embodiments, the amplification method includes a mixture of standard dNTPs and modified nucleotides that contain functional moieties (e.g., bioconjugate reactive groups) that serve as attachment points to the cell or the matrix in which the cell is embedded (e.g. a hydrogel). In embodiments, the amplification method includes a mixture of standard dNTPs and modified nucleotides that contain functional moieties (e.g., bioconjugate reactive groups) that participate in the formation of a bioconjugate linker. The modified nucleotides may react and link the amplification product to the surrounding cell scaffold. For example, amplifying may include an extension reaction wherein the polymerase incorporates a modified nucleotide into the amplification product, wherein the modified nucleotide includes a bioconjugate reactive moiety (e.g., an alkynyl moiety) attached to the nucleobase. The bioconjugate reactive moiety of the modified nucleotide participates in the formation of a bioconjugate linker by reacting with a complementary bioconjugate reactive moiety present in the cell (e.g., a crosslinking agent, such as NHS-PEG-azide, or an amine moiety) thereby attaching the amplification product to the internal scaffold of the cell. In embodiments, the functional moiety can be covalently cross-linked, copolymerize with or otherwise non-covalently bound to the matrix. In embodiments, the functional moiety can react with a cross-linker. In embodiments, the functional moiety can be part of a ligand-ligand binding pair. Suitable exemplary functional moieties include an amine, acrydite, alkyne, biotin, azide, and thiol. In embodiments of crosslinking, the functional moiety is cross-linked to modified dNTP or dUTP or both. In embodiments, suitable exemplary cross-linker reactive groups include imidoester (DMP), succinimide ester (NHS), maleimide (Sulfo-SMCC), carbodiimide (DCC, EDC) and phenyl azide. Cross-linkers within the scope of the present disclosure may include a spacer moiety. In embodiments, such spacer moieties may be functionalized. In embodiments, such spacer moieties may be chemically stable. In embodiments, such spacer moieties may be of sufficient length to allow amplification of the nucleic acid bound to the matrix. In embodiments, suitable exemplary spacer moieties include polyethylene glycol, carbon spacers, photo-cleavable spacers and other spacers known to those of skill in the art and the like. In embodiments, amplification reactions include standard dNTPs and a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, during amplification a mixture of standard dNTPs and aminoallyl deoxyuridine 5'-triphosphate (dUTP) nucleotides may be incorporated into the amplicon and subsequently cross-linked to the cell protein matrix by using a cross-linking reagent (e.g., an amine-reactive crosslinking agent with PEG spacers, such as (PEGylated bis(sulfosuccinimidyl)suberate) (BS(PEG)9)).

In embodiments, the amplification primer and the sequencing primer includes an oligonucleotide, either natural or synthetic, that is capable, upon forming a duplex with a polynucleotide template, of acting as a point of initiation of nucleic acid synthesis and being extended from its 3' end along the template so that an extended duplex is formed. The sequence of nucleotides added during the extension process is determined by the sequence of the template polynucleotide. Primers (e.g., amplification primer or sequencing primer) include nucleotides ranging from 17 to 30 nucleotides. In embodiments, the primer is at least 17 nucleotides, or alternatively, at least 18 nucleotides, or alternatively, at least 19 nucleotides, or alternatively, at least 20 nucleotides, or alternatively, at least 21 nucleotides, or alternatively, at least 22 nucleotides, or alternatively, at least 23 nucleotides, or alternatively, at least 24 nucleotides, or alternatively, at least 25 nucleotides, or alternatively, at least 26 nucleotides, or alternatively, at least 27 nucleotides, or alternatively, at least 28 nucleotides, or alternatively, at least 29 nucleotides, or alternatively, at least 30 nucleotides, or alternatively at least 50 nucleotides, or alternatively at least 75 nucleotides or alternatively at least 100 nucleotides.

In embodiments, one or more nucleotides within the amplification primer sequence, the sequencing primer sequence, and/or the immobilized oligonucleotide primer contains one or more functional moieties (e.g., bioconjugate reactive groups) that serve as attachment points to the cell (e.g., to an internal cellular component, such as a protein) or the matrix in which the cell is embedded (e.g. a hydrogel). In embodiments, one or more nucleotides within the amplification primer sequence, the sequencing primer sequence, and/or the immobilized oligonucleotide primer contains one or more functional moieties (e.g., bioconjugate reactive groups) that serve as attachment points to complementary bioconjugate reactive groups within the cell (e.g., a protein). In embodiments, a plurality of oligonucleotide primers are provided to the matrix in which the cell is embedded prior to amplification. In embodiments, a plurality of oligonucleotide primers are provided to the matrix in which the cell is embedded concurrently with amplification. In embodiments, the bioconjugate reactive group is located at the 5' or 3' end of the primer. In embodiments, the bioconjugate reactive group is located at an internal position of the primer e.g., the primer contains one or more modified nucleotides, such as aminoallyl deoxyuridine 5'-triphosphate (dUTP) nucleotide(s). In embodiments, the functional moiety can be covalently cross-linked, copolymerize with or otherwise non-covalently bound to the matrix. In embodiments, the functional moiety can react with a cross-linker. In embodiments, the functional moiety can be part of a ligand-ligand binding pair. Suitable exemplary functional moieties include an amine, acrydite, alkyne, biotin, azide, and thiol. In embodiments of crosslinking, the functional moiety is cross-linked to modified dNTP or dUTP or both. In embodiments, suitable exemplary cross-linker reactive groups include imidoester (DMP), succinimide ester (NETS), maleimide (Sulfo-SMCC), carbodiimide (DCC, EDC) and phenyl azide. Cross-linkers within the scope of the present disclosure may include a spacer moiety. In embodiments, such spacer moieties may be functionalized. In embodiments, such spacer moieties may be chemically stable. In embodiments, such spacer moieties may be of sufficient length to allow amplification of the nucleic acid bound to the matrix. In embodiments, suitable exemplary spacer moieties include polyethylene glycol, carbon spacers, photo-cleavable spacers and other spacers known to those of skill in the art and the like. In embodiments, the amplification primer and/or the sequencing primer contains a modified nucleotide (e.g., amino-allyl dUTP, 5-TCO-PEG4-dUTP, C8-Alkyne-dUTP, 5-Azidomethyl-dUTP, 5-Vinyl-dUTP, or 5-Ethynyl dLTTP). For example, prior to amplification, the modified nucleotide-containing primer is attached to the cell protein matrix by using a cross-linking reagent (e.g., an amine-reactive cross-linking agent with PEG spacers, such as (PEGylated bis (sulfosuccinimidyl)suberate) (BS(PEG)9)).

In embodiments, the primer oligonucleotide is covalently attached to the matrix or to a cellular component via a bioconjugate reactive linker. In embodiments, the 5' end of the primer contains a functional group that is capable of reacting with a complementary group so the primer may be tethered to a cellular component (e.g., a protein). Non-limiting examples of covalent attachment include amine-modified polynucleotides within the primer reacting with epoxy or isothiocyanate groups within the matrix, succinylated polynucleotides within the primer reacting with aminophenyl or aminopropyl functional groups within the matrix, dibenzocyclooctyne-modified polynucleotides within the primer reacting with azide functional groups within the matrix (or vice versa), trans-cyclooctyne-modified polynucleotides within the primer reacting with tetrazine or methyl tetrazine groups within the matrix (or vice versa), disulfide modified polynucleotides within the primer reacting with mercapto-functional groups within the matrix, amine-functionalized polynucleotides within the primer reacting with carboxylic acid groups within the matrix or cellular component via 1-ethyl-3-(3-dimethylaminopropyl)-carbodiimide hydrochloride (EDC) chemistry, thiol-modified polynucleotides within the primer attaching to the matrix or cellular component via a disulfide bond or maleimide linkage, alkyne-modified polynucleotides within the primer attaching to a matrix via copper-catalyzed click reactions to azide functional groups within the matrix, azide-modified polynucleotides within the primer attaching to the matrix via copper-catalyzed click reactions to alkyne functional groups within the matrix, and acrydite-modified polynucleotides within the primer polymerizing with free acrylic acid monomers within the matrix to form polyacrylamide. In embodiments, the primer is attached to the matrix through electrostatic binding. For example, the negatively charged phosphate backbone of the primer may be bound electrostatically to positively charged monomers in the solid support.

In embodiments, the primer includes a first bioconjugate reactive group. In embodiments, the primer is attached to a cellular compartment. In embodiments, the cellular component includes a second bioconjugate reactive group. In embodiments, the first bioconjugate reactive group is attached to the second bioconjugate reactive group by covalent or non-covalent bonding. In embodiments, the primer is covalently attached to a cellular component. In embodiments, the 5' end of the primer contains a functional group that is tethered to the cellular component. In embodiments, the primer is covalently attached to a matrix within the cell. In embodiments, the 5' end of the primer contains a functional group that is tethered to the matrix within the cell. Non-limiting examples of covalent attachment include amine-modified polynucleotides reacting with epoxy or isothiocyanate groups in the cell or matrix within the cell, succinylated polynucleotides reacting with aminophenyl or aminopropyl functional groups in the cell or matrix within the cell, dibenzocyclooctyne-modified polynucleotides reacting with azide functional groups in the cell or matrix within the cell (or vice versa), trans-cyclooctyne-modified polynucleotides reacting with tetrazine or methyl tetrazine groups in the cell or matrix within the cell (or vice versa), disulfide modified polynucleotides reacting with mercapto-functional groups in the cell or matrix within the cell, amine-functionalized polynucleotides reacting with carboxylic acid groups in the cell or matrix within the cell via 1-ethyl-3-(3-dimethylaminopropyl)-carbodiimide hydrochloride (EDC) chemistry, thiol-modified polynucleotides attaching to cell or matrix within the cell via a disulphide bond or maleimide linkage, alkyne-modified polynucleotides attaching to the cell or matrix within the cell via copper-catalyzed click reactions to azide functional groups in the cell or matrix within the cell, and acrydite-modified polynucleotides polymerizing with free acrylic acid monomers in the cell or matrix within the cell to form polyacrylamide or reacting with thiol groups in the cell or matrix within the cell. In embodiments, the primer is attached to the polymer through electrostatic binding. For example, the negatively charged phosphate backbone of the primer may be bound electrostatically to positively charged monomers in the matrix.

In embodiments, the primer oligonucleotide is attached to the matrix or to a cellular component via a specific binding reagent. In embodiments, the specific binding reagent includes an antibody, single-chain Fv fragment (scFv), antibody fragment-antigen binding (Fab), or an aptamer. In embodiments, the specific binding reagent includes an antibody, or antigen binding fragment, an aptamer, affimer, or non-immunoglobulin scaffold. In embodiments, the specific binding reagent is a peptide, a cell penetrating peptide, an aptamer, a DNA aptamer, an RNA aptamer, an antibody, an antibody fragment, a light chain antibody fragment, a single-chain variable fragment (scFv), a lipid, a lipid derivative, a phospholipid, a fatty acid, a triglyceride, a glycerolipid, a glycerophospholipid, a sphingolipid, a saccharolipid, a polyketide, a polylysine, polyethyleneimine, diethylaminoethyl (DEAE)-dextran, cholesterol, or a sterol moiety. For example, the matrix or cellular component (e.g., a protein) may contain a complementary specific binding reagent to the primer containing a specific binding reagent.

In embodiments, the method includes contacting the cell with a plurality of specific binding reagents, wherein the specific binding reagent includes an oligonucleotide primer. In embodiments, the oligonucleotide primer may be used to aid in tethering the extension product to a confined area and may not be extended. In embodiments, the oligonucleotide primer includes a blocking group at the 3' end that prevents polymerase extension. In embodiments, the method includes extending the one or more oligonucleotide primers hybridized to an extension product with a polymerase. For example, the one or more oligonucleotide primers attached to the specific binding reagent (e.g., an antibody) may be used to aid in tethering the extension product to a localized area and may be extended in an exponential RCA amplification reaction. In embodiments, the 5' end of the primer is attached to the specific binding reagent. In embodiments, the specific binding reagent includes an antibody, single-chain Fv fragment (scFv), antibody fragment-antigen binding (Fab), or an aptamer. For example, the matrix or cellular component (e.g., a protein) may contain a complementary specific binding reagent to the primer containing a specific binding reagent.

In embodiments, the method includes amplifying the circular polynucleotide by extending an amplification primer with a strand-displacing polymerase, wherein the primer extension generates an extension product including multiple complements of the circular polynucleotide. In embodiments, the method of amplifying includes an isothermal amplification method. In embodiments, the method of amplifying includes rolling circle amplification (RCA) or rolling circle transcription (RCT). In embodiments, the method of amplifying is rolling circle amplification (RCA). In embodiments, amplifying includes exponential rolling circle amplification (eRCA). Exponential RCA is similar to the linear process except that it uses a second primer (e.g., one or more immobilized oligonucleotide(s)) having a sequence that is identical to at least a portion of the circular template (Lizardi et al. Nat. Genet. 19:225 (1998)). This two-primer system achieves isothermal, exponential amplification. Exponential RCA has been applied to the amplification of non-circular DNA through the use of a linear probe that binds at both of its ends to contiguous regions of a target DNA followed by circularization using DNA ligase (Nilsson et al. Science 265(5181):208 5 (1994)).

In embodiments, amplifying the circular oligonucleotide includes incubation with a strand-displacing polymerase. In embodiments, amplifying includes incubation with a strand-displacing polymerase for about 10 seconds to about 60 minutes. In embodiments, amplifying includes incubation with a strand-displacing polymerase for about 60 seconds to about 60 minutes. In embodiments, amplifying includes incubation with a strand-displacing polymerase for about 10 minutes to about 60 minutes. In embodiments, amplifying includes incubation with a strand-displacing polymerase for about 10 minutes to about 30 minutes. In embodiments, amplifying includes incubation with a strand-displacing polymerase at a temperature of about 20° C. to about 50° C. In embodiments, incubation with the strand-displacing polymerase is at a temperature of about 35° C. to 42° C. In embodiments, the strand-displacing polymerase is phi29 polymerase, SD polymerase, Bst large fragment polymerase, phi29 mutant polymerase, or a thermostable phi29 mutant polymerase.

In embodiments, the extension product includes three or more copies of the target nucleic acid. In embodiments, the extension product includes at least three or more copies of the target nucleic acid. In embodiments, the extension product includes at least five or more copies of the target nucleic acid. In embodiments, the extension product includes at 5 to 10 copies of the target nucleic acid. In embodiments, the extension product includes 10 to 20 copies of the target nucleic acid. In embodiments, the extension product includes 20 to 50 copies of the target nucleic acid.

In embodiments, the method includes sequencing the extension products, which includes the target nucleic acid sequence. A variety of sequencing methodologies can be used such as sequencing-by synthesis (SBS), pyrosequencing, sequencing by ligation (SBL), or sequencing by hybridization (SBH). Pyrosequencing detects the release of inorganic pyrophosphate (PPi) as particular nucleotides are incorporated into a nascent nucleic acid strand (Ronaghi, et al., Analytical Biochemistry 242(1), 84-9 (1996); Ronaghi, Genome Res. 11(1), 3-11 (2001); Ronaghi et al. Science 281(5375), 363 (1998); U.S. Pat. Nos. 6,210,891; 6,258,568; and 6,274,320, each of which is incorporated herein by reference in its entirety). In pyrosequencing, released PPi can be detected by being converted to adenosine triphosphate (ATP) by ATP sulfurylase, and the level of ATP generated can be detected via light produced by luciferase. In this manner, the sequencing reaction can be monitored via a luminescence detection system. In both SBL and SBH methods, target nucleic acids, and amplicons thereof, are subjected to repeated cycles of oligonucleotide delivery and detection. SBL methods, include those described in Shendure et al. Science 309:1728-1732 (2005); U.S. Pat. Nos. 5,599,675; and 5,750,341, each of which is incorporated herein by reference in its entirety; and the SBH methodologies are as described in Bains et al., Journal of Theoretical Biology 135(3), 303-7 (1988); Drmanac et al., Nature Biotechnology 16, 54-58 (1998); Fodor et al., Science 251

(4995), 767-773 (1995); and WO 1989/10977, each of which is incorporated herein by reference in its entirety.

In SBS, extension of a nucleic acid primer along a nucleic acid template is monitored to determine the sequence of nucleotides in the template. The underlying chemical process can be catalyzed by a polymerase, wherein fluorescently labeled nucleotides are added to a primer (thereby extending the primer) in a template dependent fashion such that detection of the order and type of nucleotides added to the primer can be used to determine the sequence of the template. In embodiments, sequencing includes annealing and extending a sequencing primer to incorporate a detectable label that indicates the identity of a nucleotide in the target polynucleotide, detecting the detectable label, and repeating the extending and detecting of steps. In embodiments, the methods include sequencing one or more bases of a target nucleic acid by extending a sequencing primer hybridized to a target nucleic acid (e.g., an amplification product produced by the amplification methods described herein). In embodiments, sequencing may be accomplished by a sequencing-by-synthesis (SBS) process. In embodiments, sequencing includes a sequencing by synthesis process, where individual nucleotides are identified iteratively, as they are polymerized to form a growing complementary strand. In embodiments, nucleotides added to a growing complementary strand include both a label and a reversible chain terminator that prevents further extension, such that the nucleotide may be identified by the label before removing the terminator to add and identify a further nucleotide. Such reversible chain terminators include removable 3' blocking groups, for example as described in U.S. Pat. Nos. 7,541,444 and 7,057,026. Once such a modified nucleotide has been incorporated into the growing polynucleotide chain complementary to the region of the template being sequenced, there is no free 3'-OH group available to direct further sequence extension and therefore the polymerase cannot add further nucleotides. Once the identity of the base incorporated into the growing chain has been determined, the 3' reversible terminator may be removed to allow addition of the next successive nucleotide. By ordering the products derived using these modified nucleotides it is possible to deduce the DNA sequence of the oligonucleotide target nucleic acid sequence.

In embodiments, the methods of sequencing a nucleic acid include a extending a polynucleotide by using a polymerase. In embodiments, the polymerase is a DNA polymerase. In embodiments, the DNA polymerase is a Pol I DNA polymerase, Pol II DNA polymerase, Pol III DNA polymerase, Pol IV DNA polymerase, Pol V DNA polymerase, Pol β DNA polymerase, Pol μ DNA polymerase, Pol λ DNA polymerase, Pol σ DNA polymerase, Pol α DNA polymerase, Pol δ DNA polymerase, Pol ε DNA polymerase, Pol η DNA polymerase, Pol ι DNA polymerase, Pol κ DNA polymerase, Pol ζ DNA polymerase, Pol γ DNA polymerase, Pol θ DNA polymerase, Pol ν DNA polymerase, or a thermophilic nucleic acid polymerase (e.g., Terminator γ, 9°N polymerase (exo-), Terminator II, Terminator III, or Terminator IX). In embodiments, the DNA polymerase is a thermophilic nucleic acid polymerase. In embodiments, the DNA polymerase is a modified archaeal DNA polymerase. In embodiments, the polymerase is a mutant $P.$ $abyssi$ polymerase (e.g., such as a mutant $P.$ $abyssi$ polymerase described in WO 2018/148723 or WO 2020/056044, each of which are incorporated herein by reference for all purposes). In embodiments, the polymerase is a bacterial DNA polymerase, eukaryotic DNA polymerase, archaeal DNA polymerase, viral DNA polymerase, or phage DNA polymerases. Bacterial DNA polymerases include $E. coli$ DNA polymerases I, II and III, IV and V, the Klenow fragment of $E. coli$ DNA polymerase, $Clostridium$ $stercorarium$ (Cst) DNA polymerase, $Clostridium$ $thermocellum$ (Cth) DNA polymerase and $Sulfolobus$ $solfataricus$ (Sso) DNA polymerase. Eukaryotic DNA polymerases include DNA polymerases α, β, γ, δ, ε, η, ζ, λ, σ, μ, and k, as well as the Rev1 polymerase (terminal deoxycytidyl transferase) and terminal deoxynucleotidyl transferase (TdT). Viral DNA polymerases include T4 DNA polymerase, phi-29 DNA polymerase, GA-1, phi-29-like DNA polymerases, PZA DNA polymerase, phi-15 DNA polymerase, Cpl DNA polymerase, Cpl DNA polymerase, T7 DNA polymerase, and T4 polymerase. Other useful DNA polymerases include thermostable and/or thermophilic DNA polymerases such as $Thermus$ $aquaticus$ (Taq) DNA polymerase, $Thermus$ $filiformis$ (Tfi) DNA polymerase, $Thermococcus$ $zilligi$ (Tzi) DNA polymerase, $Thermus$ $thermophilus$ (Tth) DNA polymerase, $Thermus$ $flavusu$ (Tfl) DNA polymerase, $Pyrococcus$ $woesei$ (Pwo) DNA polymerase, $Pyrococcus$ $furiosus$ (Pfu) DNA polymerase and Turbo Pfu DNA polymerase, $Thermococcus$ $litoralis$ (Tli) DNA polymerase, $Pyrococcus$ sp. GB-D polymerase, $Thermotoga$ $maritima$ (Tma) DNA polymerase, $Bacillus$ $stearothermophilus$ (Bst) DNA polymerase, $Pyrococcus$ $Kodakaraensis$ (KOD) DNA polymerase, Pfx DNA polymerase, $Thermococcus$ sp. JDF-3 (JDF-3) DNA polymerase, $Thermococcus$ $gorgonarius$ (Tgo) DNA polymerase, $Thermococcus$ $acidophilium$ DNA polymerase; $Sulfolobus$ $acidocaldarius$ DNA polymerase; $Thermococcus$ sp. go N-7 DNA polymerase; $Pyrodictium$ $occultum$ DNA polymerase; $Methanococcus$ $voltae$ DNA polymerase; $Methanococcus$ $thermoautotrophicum$ DNA polymerase; $Methanococcus$ $jannaschii$ DNA polymerase; $Desulfurococcus$ strain TOK DNA polymerase (D. Tok Pol); $Pyrococcus$ $abyssi$ DNA polymerase; $Pyrococcus$ $horikoshii$ DNA polymerase; $Pyrococcus$ $islandicum$ DNA polymerase; $Thermococcus$ $fumicolans$ DNA polymerase; $Aeropyrum$ $pernix$ DNA polymerase; and the heterodimeric DNA polymerase DP1/DP2. In embodiments, the polymerase is 3PDX polymerase as disclosed in U.S. Pat. No. 8,703,461, the disclosure of which is incorporated herein by reference. In embodiments, the polymerase is a reverse transcriptase. Exemplary reverse transcriptases include, but are not limited to, HIV-1 reverse transcriptase from human immunodeficiency virus type 1 (PDB 1HMV), HIV-2 reverse transcriptase from human immunodeficiency virus type 2, M-MLV reverse transcriptase from the Moloney murine leukemia virus, AMV reverse transcriptase from the avian myeloblastosis virus, and Telomerase reverse transcriptase.

In embodiments, sequencing includes a plurality of sequencing cycles. In embodiments, sequencing includes 20 to 100 sequencing cycles. In embodiments, sequencing includes 50 to 100 sequencing cycles. In embodiments, sequencing includes 50 to 300 sequencing cycles. In embodiments, sequencing includes 50 to 150 sequencing cycles. In embodiments, sequencing includes at least 10, 20, 30 40, or 50 sequencing cycles. In embodiments, sequencing includes at least 10 sequencing cycles. In embodiments, sequencing includes 10 to 20 sequencing cycles. In embodiments, sequencing includes 10, 11, 12, 13, 14, or 15 sequencing cycles. In embodiments, sequencing includes (a) extending a sequencing primer by incorporating a labeled nucleotide, or labeled nucleotide analogue and (b) detecting the label to generate a signal for each incorporated nucleotide or nucleotide analogue.

In embodiments, sequencing includes sequentially extending a plurality of sequencing primers (e.g., sequencing a first region of a target nucleic acid followed by sequencing a second region of a target nucleic acid, followed by sequencing N regions, where N is the number of sequencing primers in the known sequencing primer set). In embodiments, sequencing includes generating a plurality of sequencing reads.

In embodiments, sequencing includes extending a sequencing primer to generate a sequencing read. In embodiments, sequencing includes extending a sequencing primer by incorporating a labeled nucleotide, or labeled nucleotide analogue and detecting the label to generate a signal for each incorporated nucleotide or nucleotide analogue. In embodiments, the labeled nucleotide or labeled nucleotide analogue further includes a reversible terminator moiety.

In embodiments, the labeled nucleotide or labeled nucleotide analogue further includes a reversible terminator moiety. In embodiments, the reversible terminator moiety is attached to

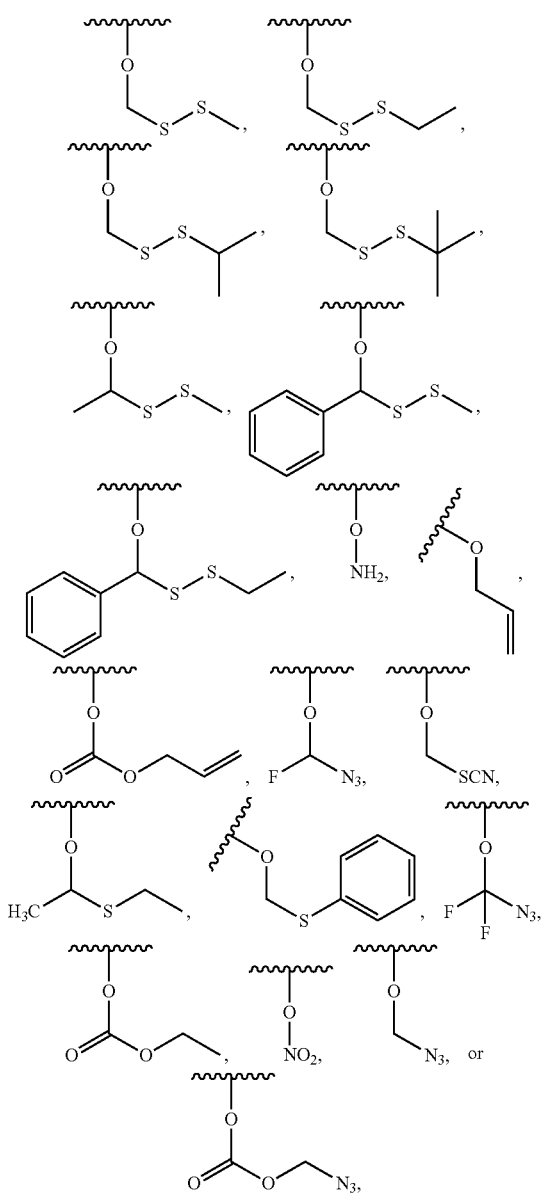

the 3' oxygen of the nucleotide and is independently wherein the 3' oxygen is explicitly depicted in the above formulae. Additional examples of reversible terminators may be found in U.S. Pat. No. 6,664,079, Ju J. et al. (2006) *Proc Natl Acad Sci USA* 103(52):19635-19640; Ruparel H. et al. (2005) *Proc Natl Acad Sci USA* 102(17):5932-5937; Wu J. et al. (2007) *Proc Natl Acad Sci USA* 104(104):16462-16467; Guo J. et al. (2008) *Proc Natl Acad Sci USA* 105(27): 9145-9150 Bentley D. R. et al. (2008) *Nature* 456(7218): 53-59; or Hutter D. et al. (2010) *Nucleosides Nucleotides & Nucleic Acids* 29:879-895, which are incorporated herein by reference in their entirety for all purposes. In embodiments, a polymerase-compatible cleavable moiety includes an azido moiety or a dithiol moiety.

In embodiments, sequencing includes sequencing by synthesis, sequencing by ligation, or pyrosequencing. In embodiments, sequencing includes a plurality of sequencing cycles. In embodiments, sequencing includes extending one or more sequencing primers hybridized to the extension product. In embodiments, sequencing includes extending a sequencing primer by incorporating a labeled nucleotide, or labeled nucleotide analogue and detecting the label to generate a signal for each incorporated nucleotide or nucleotide analogue, wherein the sequencing primer is hybridized to the amplification product. In embodiments, the labeled nucleotide or labeled nucleotide analogue further includes a reversible terminator moiety.

In embodiments, detecting includes two-dimensional (2D) or three-dimensional (3D) fluorescent microscopy. Suitable imaging technologies are known in the art, as exemplified by Larsson et al., Nat. Methods (2010) 7:395-397 and associated supplemental materials, the entire content of which is incorporated by reference herein in its entirety. In embodiments of the methods provided herein, the imaging is accomplished by confocal microscopy. Confocal fluorescence microscopy involves scanning a focused laser beam across the sample, and imaging the emission from the focal point through an appropriately-sized pinhole. This suppresses the unwanted fluorescence from sections at other depths in the sample. In embodiments, the imaging is accomplished by multi-photon microscopy (e.g., two-photon excited fluorescence or two-photon-pumped microscopy). Unlike conventional single-photon emission, multi-photon microscopy can utilize much longer excitation wavelength up to the red or near-infrared spectral region. This lower energy excitation requirement enables the implementation of semiconductor diode lasers as pump sources to significantly enhance the photostability of materials. Scanning a single focal point across the field of view is likely to be too slow for many sequencing applications. To speed up the image acquisition, an array of multiple focal points can be used. The emission from each of these focal points can be imaged onto a detector, and the time information from the scanning mirrors can be translated into image coordinates. Alternatively, the multiple focal points can be used just for the purpose of confining the fluorescence to a narrow axial section, and the emission can be imaged onto an imaging detector, such as a CCD, EMCCD, or s-CMOS detector. A scientific grade CMOS detector offers an optimal combination of sensitivity, readout speed, and low cost. One configuration used for confocal microscopy is spinning disk confocal microscopy. In 2-photon microscopy, the technique of using multiple focal points simultaneously to parallelize the readout has been called Multifocal Two-Photon Microscopy (MTPM). Several techniques for MTPM are available, with applications typically involving imaging in biological tissue. In embodiments of the methods provided herein, the imaging is accomplished by light sheet fluorescence microscopy (LSFM). In embodiments, detecting includes 3D structured illumination (3DSIM). In 3DSIM, patterned light is used for excitation, and fringes in the Moiré pattern generated by interference of the illumination pattern and the sample, are used to reconstruct the source of light in three dimensions. In order to illuminate the entire field, multiple spatial patterns are used to excite the same physical area, which are then digitally processed to reconstruct the final image. See York, Andrew G., et al. "Instant super-resolution imaging in live cells and embryos via analog image processing." *Nature methods* 10.11 (2013): 1122-1126 which is incorporated herein by reference. In embodiments, detecting includes selective planar illumination microscopy, light sheet microscopy, emission manipulation, pinhole confocal microscopy, aperture correlation confocal microscopy, volumetric reconstruction from slices, deconvolution microscopy, or aberration-corrected multifocus microscopy. In embodiments, detecting includes digital holographic microscopy (see for example Manoharan, V. N. Frontiers of Engineering: Reports on Leading-edge Engineering from the 2009 Symposium, 2010, 5-12, which is incorporated herein by reference). In embodiments, detecting includes confocal microscopy, light sheet microscopy, or multi-photon microscopy.

In embodiments, the method includes sequencing a plurality of target nucleic acids of a cell in situ within an optically resolved volume. In embodiments, the number of unique targets detected within an optically resolved volume of a sample is about 3, 10, 30, 50, or 100. In embodiments, the number of unique targets detected within an optically resolved volume of a sample is about 1 to 10. In embodiments, the number of unique targets detected within an optically resolved volume of a sample is about 5 to 10. In embodiments, the number of unique targets detected within an optically resolved volume of a sample is about 1 to 5. In embodiments, the number of unique targets detected within an optically resolved volume of a sample is at least 3, 10, 30, 50, or 100. In embodiments, the number of unique targets detected within an optically resolved volume of a sample is less than 3, 10, 30, 50, or 100. In embodiments, the number of unique targets detected within an optically resolved volume of a sample is about 1, 2, 3, 4, 5, 6, 7, 8, 9, 10, 20, 50, 100, 500, 1,000, 5,000, 10,000, or 200,000. In embodiments, the methods allow for detection of a single target of interest. In embodiments, the methods allow for multiplex detection of a plurality of targets of interest.

Figure 5:
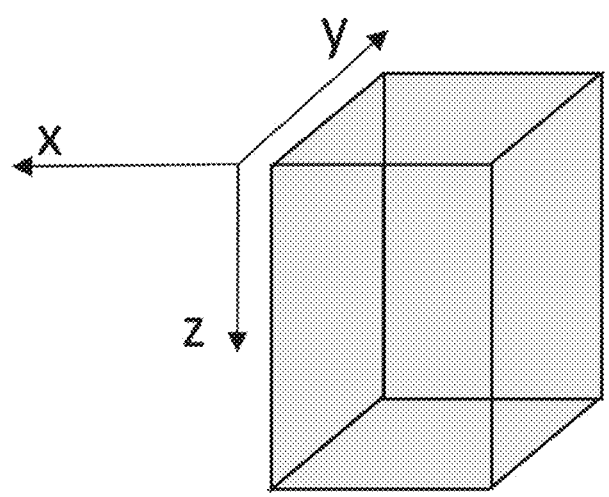
FIG. 5. A cartoon depiction of a voxel with the primary coordinate system in Cartesian coordinates. The optically resolved volume has a lateral resolution corresponding to the xy plane, and an axial resolution, corresponding to the z axis as observed in FIG. 5. In embodiments, the dimensions (i.e., the x, y, and z dimensions) of the optically resolved volume are given as (x-dimension)×(y-dimension)×(z-dimension); for example 0.5 µm×0.5 µm×2 µm.

In embodiments, the optically resolved volume has an axial resolution (i.e., depth, or z) that is greater than the lateral resolution (i.e., xy plane). In embodiments, the optically resolved volume has an axial resolution that is greater than twice the lateral resolution. In embodiments, the dimensions (i.e., the x, y, and z dimensions) of the optically resolved volume are about 0.5 μm×0.5 μm×0.5 μm; 1 μm×1 μm×1 μm; 2 μm×2 μm×2 μm; 0.5 μm×0.5 μm×1 μm; 0.5 μm×0.5 μm×2 μm; 2 μm×2 μm×1 μm; or 1 μm×1 μm×2 μm. In embodiments, the dimensions (i.e., the x, y, and z dimensions) of the optically resolved volume are about 1 μm×1 μm×2 μm; 1 μm×1 μm×3 μm; 1 μm×1 μm×4 μm; or about 1 μm×1 μm×5 μm. See FIG. 5, for example. In embodiments, the dimensions (i.e., the x, y, and z dimensions) of the optically resolved volume are about 1 μm×1 μm×5 μm. In embodiments, the dimensions (i.e., the x, y, and z dimensions) of the optically resolved volume are about 1 μm×1 μm×6 μm. In embodiments, the dimensions (i.e., the x, y, and z dimensions) of the optically resolved volume are about 1 μm×1 μm×7 μm. In embodiments, the optically resolved volume is a cubic micron. In embodiments, the optically resolved volume has a lateral resolution from about 100 to 200 nanometers, from 200 to 300 nanometers, from 300 to 400 nanometers, from 400 to 500 nanometers, from 500 to 600 nanometers, or from 600 to 1000 nanometers. In embodiments, the optically resolved volume has a axial resolution from about 100 to 200 nanometers, from 200 to 300 nanometers, from 300 to 400 nanometers, from 400 to 500 nanometers, from 500 to 600 nanometers, or from 600 to 1000 nanometers. In embodiments, the optically resolved volume has a axial resolution from about 1 to 2 μm, from 2 to 3 μm, from 3 to 4 μm, from 4 to 5 μm, from 5 to 6 μm, or from 6 to 10 μm.

In embodiments, the method further includes an additional imaging modality, immunofluorescence (IF), or immunohistochemistry modality (e.g., immunostaining). In embodiments, the method includes ER staining (e.g., contacting the cell with a cell-permeable dye which localizes to the endoplasmic reticula), Golgi staining (e.g., contacting the cell with a cell-permeable dye which localizes to the Golgi), F-actin staining (e.g., contacting the cell with a phalloidin-conjugated dye that binds to actin filaments), lysosomal staining (e.g., contacting the cell with a cell-permeable dye that accumulates in the lysosome via the lysosome pH gradient), mitochondrial staining (e.g., contacting the cell with a cell-permeable dye which localizes to the mitochondria), nucleolar staining, or plasma membrane staining. For example, the method includes live cell imaging (e.g., obtaining images of the cell) prior to or during fixing, immobilizing, and permeabilizing the cell. Immunohistochemistry (IHC) is a powerful technique that exploits the specific binding between an antibody and antigen to detect and localize specific antigens in cells and tissue, commonly detected and examined with the light microscope. Known IHC modalities may be used, such as the protocols described in Magaki, S., Hojat, S. A., Wei, B., So, A., & Yong, W. H. (2019). *Methods in molecular biology* (*Clifton, N.J.*), 1897, 289-298, which is incorporated herein by reference. In embodiments, the additional imaging modality includes bright field microscopy, phase contrast microscopy, Nomarski differential-interference-contrast microscopy, or dark field microscopy. In embodiments, the method further includes determining the cell morphology (e.g., the cell boundary or cell shape) using known methods in the art. For example, to determining the cell boundary includes comparing the pixel values of an image to a single intensity threshold, which may be determined quickly using histogram-based approaches as described in Carpenter, A. et al Genome Biology 7, R100 (2006) and Arce, S., Sci Rep 3, 2266 (2013)).

In aspects and embodiments described herein, the methods are useful in the field of predictive medicine in which diagnostic assays, prognostic assays, pharmacogenomics, and monitoring clinical trials are used for prognostic (i.e., predictive) purposes to thereby treat an individual prophylactically. Accordingly, in embodiments the methods of diagnosing and/or prognosing one or more diseases and/or disorders using one or more of expression profiling methods described herein are provided.

In an aspect is provided a method of detecting a disorder (e.g., cancer) or a disease-causing mutation or allele in a cell. In embodiments, the cell includes an oncogene (e.g., HER2, BRAF, EGFR, KRAS) and utilizing the methods described herein the oncogene is identified, thereby detecting a disorder when the presence of the oncogene is identified. In embodiments, the sample includes a nucleic acid molecule which includes a disease-causing mutation or allele. In embodiments, the method includes hybridizing an oligonucleotide primer which is correlated with the disease-causing mutation or allele. In embodiments, the method includes ligating a mutation-specific oligonucleotide primer only when the disease-causing mutation or allele is present in the nucleic acid target. In embodiments, the disease-causing mutation or allele is a base substitution, an insertion mutation, a deletion mutation, a gene amplification, a gene deletion, a gene fusion event, or a gene inversion event.

In embodiments, the mutation or allele is associated with an increased predisposition for one or more diseases, disorders, or other phenotypes. In embodiments, the mutation or allele is associated with a decreased predisposition for one or more diseases, disorders, or other phenotypes. For example, some mutations or alleles are associated with a cancer phenotype, such as decreased growth inhibition, evasion of immune detection, or dedifferentiation. Mutations that can be detected using the method provided herein include for example, mutations to BRAF, EGFR, Her2/ERBB2, and other somatic mutations as exemplified by Greenman et al., Nature (2007) 446:153-158, hereby incorporated by reference in its entirety.

In an aspect is provided a method of sequencing an agent-mediated nucleic acid sequence of a cell, the method including administering a genetically modifying agent to the cell, sequencing an agent-mediated nucleic acid sequence of the cell in situ according to the methods as described herein. In embodiments, the method includes the following steps in situ for each of the plurality of target nucleic acids: i) hybridizing an oligonucleotide primer to the target nucleic acid, wherein the oligonucleotide primer includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region (e.g., 5' with respect to the first complementary region of the target nucleic acid); ii) circularizing the oligonucleotide primer to generate a circular oligonucleotide, wherein circularizing includes extending the 3' end of the oligonucleotide primer (e.g., extending the 3' end of the primer using a polymerase (e.g., a *Thermus thermophilus* (Tth) DNA polymerase) to incorporate one or more nucleotides) along the target nucleic acid to generate a complementary sequence (e.g., complementary to the target nucleic acid, for example a target RNA sequence), and ligating the complementary sequence to the 5' end of the oligonucleotide primer; iii) amplifying the circular oligonucleotide by extending an amplification primer hybridized to the circular oligonucleotide with a strand-displacing polymerase, wherein the amplification primer extension generates an extension product including multiple complements of the circular oligonucleotide; and iv) sequencing the extension product of step (iii).

In an aspect is provided a method of identifying a nucleic acid sequence as an agent-mediated nucleic acid sequence, the method including administering a genetically modifying agent to a cell, detecting whether an agent-mediated nucleic acid sequence is present in the cell by sequencing a plurality of target nucleic acids according to the methods as described herein, and identifying the nucleic acid sequence as an agent-mediated nucleic acid sequence when the presence of the agent-mediated nucleic acid is detected in the cell. In embodiments, the method includes the following steps in situ for each of the plurality of target nucleic acids: i) hybridizing an oligonucleotide primer to the target nucleic acid, wherein the oligonucleotide primer includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region; ii) circularizing the oligonucleotide primer to generate a circular oligonucleotide, wherein circularizing includes extending the 3' end of the oligonucleotide primer (e.g., extending the 3' end of the primer using a polymerase (e.g., a *Thermus thermophilus* (Tth) DNA polymerase) to incorporate one or more nucleotides) along the target nucleic acid to generate a complementary sequence (e.g., complementary to the target nucleic acid, for example a target RNA sequence), and ligating the complementary sequence to the 5' end of the oligonucleotide primer; iii) amplifying the circular oligonucleotide by extending an amplification primer hybridized to the circular oligonucleotide with a strand-displacing polymerase, wherein the amplification primer extension generates an extension product including multiple complements of the circular oligonucleotide; and iv) sequencing the extension product of step (iii).

In an aspect is provided a method of identifying a cell that responds to a genetically modifying agent, the method including administering a genetically modifying agent to the cell, detecting whether an agent-mediated nucleic acid sequence is present in the cell by sequencing a plurality of target nucleic acids according to the methods as described herein, and identifying a cell that responds to a genetically modifying agent when the presence of the agent-mediated nucleic acid is detected in the cell. In embodiments, the method includes the following steps in situ for each of the plurality of target nucleic acids: i) hybridizing an oligonucleotide primer to the target nucleic acid, wherein the oligonucleotide primer includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region; ii) circularizing the oligonucleotide primer to generate a circular oligonucleotide, wherein circularizing includes extending the 3' end of the oligonucleotide primer (e.g., extending the 3' end of the primer using a polymerase (e.g., a *Thermus thermophilus* (Tth) DNA polymerase) to incorporate one or more nucleotides) along the target nucleic acid to generate a complementary sequence (e.g., complementary to the target nucleic acid, for example a target RNA sequence), and ligating the complementary sequence to the 5' end of the oligonucleotide primer; iii) amplifying the circular oligonucleotide by extending an amplification primer hybridized to the circular oligonucleotide with a strand-displacing polymerase, wherein the amplification primer extension generates an extension product including multiple complements of the circular oligonucleotide; and iv) sequencing the extension product of step (iii).

In an aspect is provided a method of identifying an agent as a genetically modifying agent, the method including administering an agent to a cell, detecting whether an agent-mediated nucleic acid sequence is present in the cell by sequencing a plurality of target nucleic acids according to any of the methods as described herein, and identifying the genetically modifying agent when the presence of the agent-mediated nucleic acid is detected in the cell. In embodiments, the method includes the following steps in situ for each of the plurality of target nucleic acids: i) hybridizing an oligonucleotide primer to the target nucleic acid, wherein the oligonucleotide primer includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region; ii) circularizing the oligonucleotide primer to generate a circular oligonucleotide, wherein circularizing includes extending the 3' end of the oligonucleotide primer along the target nucleic acid to generate a complementary sequence, and ligating the complementary sequence to the 5' end of the oligonucleotide primer; iii) amplifying the circular oligonucleotide by extending an amplification primer hybridized to the circular oligonucleotide with a strand-displacing polymerase, wherein the amplification primer extension generates an extension product including multiple complements of the circular oligonucleotide; and iv) sequencing the extension product of step (iii).

In embodiments, the genetically modifying agent is a pathogen. In embodiments, the genetically modifying agent is a virus. In embodiments, the genetically modifying agent is a DNA virus (e.g., pox virus, herpesvirus, adenovirus, parvovirus, or warts virus). In embodiments, the genetically modifying agent is an RNA virus (e.g., influenza virus, rotavirus, mumps virus, rabies virus, eastern equine encephalitis virus, corona virus, LCM virus, polio virus, or HIV virus). In embodiments, the genetically modifying agent is a toxin. In embodiments, the genetically modifying agent is a peptide. In embodiments, the genetically modifying agent is a prion. In embodiments, the genetically modifying agent is a small molecule (e.g., a pharmaceutical agent).

In an aspect is provided a method of identifying a cell that includes a synthetic target. In embodiments, the method includes detecting whether a synthetic target is present in the cell by detecting a plurality of different targets within an optically resolved volume of a cell in situ, according to the methods described herein, including embodiments, and identifying a cell that includes a synthetic target when the presence of the synthetic target is detected in the cell. In embodiments, the method includes the following steps in situ for each of the plurality of target nucleic acids: i) hybridizing an oligonucleotide primer to the target nucleic acid, wherein the oligonucleotide primer includes a first region at a 3' end that hybridizes to a first complementary region of the target nucleic acid, and a second region at a 5' end that hybridizes to a second complementary region of the target nucleic acid, wherein the second complementary region is 5' with respect to the first complementary region; ii) circularizing the oligonucleotide primer to generate a circular oligonucleotide, wherein circularizing includes extending the 3' end of the oligonucleotide primer (e.g., extending the 3' end of the primer using a polymerase (e.g., a *Thermus thermophilus* (Tth) DNA polymerase) to incorporate one or more nucleotides) along the target nucleic acid to generate a complementary sequence (e.g., complementary to the target nucleic acid, for example a target RNA sequence), and ligating the complementary sequence to the 5' end of the oligonucleotide primer; iii) amplifying the circular oligonucleotide by extending an amplification primer hybridized to the circular oligonucleotide with a strand-displacing polymerase, wherein the amplification primer extension generates an extension product including multiple complements of the circular oligonucleotide; and iv) sequencing the extension product of step (iii).

In embodiments the synthetic target is a chimeric antigen receptor (CAR) or a gene that encodes a chimeric antigen receptor (CAR). In embodiments the synthetic target is a target introduced to the cell by genetic engineering methods (e.g., transcription activator-like effector nucleases (TALENs) or clustered regularly interspaced short palindromic repeats (CRISPR) methods).

EXAMPLES

Example 1: T-Cell and B-Cell Receptor Repertoire Sequencing

The functions of immune cells such as B- and T-cells are predicated on the recognition through specialized receptors of specific targets (antigens) in pathogens. There are approximately $10^{10}$-$10^{11}$ B-cells and $10^{11}$ T-cells in a human adult (Ganusov V V, De Boer R J. Trends Immunol. 2007; 28(12):514-8; and Bains I, Antia R, Callard R, Yates A J. Blood. 2009; 113(22):5480-5487). Immune cells are critical components of adaptive immunity in humans. Immune cells (e.g., T cells, B cells, NK cells, neutrophils, and monocytes) directly bind to pathogens through antigen-binding regions present on the cells. Within lymphoid organs (e.g., bone marrow for B cells and the thymus for T cells) the gene segments variable (V), joining (J), and diversity (D) rearrange to produce a novel amino acid sequence in the antigen-binding regions of antibodies that allow for the recognition of antigens from a range of pathogens (e.g., bacteria, viruses, parasites, and worms) as well as antigens arising from cancer cells. The large number of possible V-D-J segments, combined with additional (junctional) diversity, lead to a theoretical diversity of $>10^{14}$, which is further increased during adaptive immune responses. Overall, the result is that each B- and T-cell expresses a practically unique receptor, whose sequence is the outcome of both germline and somatic diversity. These antibodies also contain a constant (C) region, which confers the isotype to the antibody. In most mammals, there are five antibody isotypes: IgA, IgD, IgE, IgG, and IgM. For example, each antibody in the IgA isotype shares the same constant region.

While parts of the B-cell immunoglobulin receptor (BCR) can be traced back to segments encoded in the germline (i.e., the V, D and J segments), the set of segments used by each receptor is something that needs to be determined as it is coded in a highly repetitive region of the genome (Yaari G, Kleinstein S H. Practical guidelines for B-cell receptor repertoire analysis. Genome Med. 2015; 7:121. (2015)). Additionally, there are no pre-existing full-length templates to align the sequencing reads. Thus, obtaining long-range sequence data is incredibly insightful to gain insights into the adaptive immune response in healthy individuals and in those with a wide range of diseases. Utilizing the methods described herein, comprehensive in situ snapshots of the repertoire diversity for each class of antibody may be realized by using targeted oligonucleotide probes to sequence the C-V-D-J segments in intact B cells.

Figure 1B:
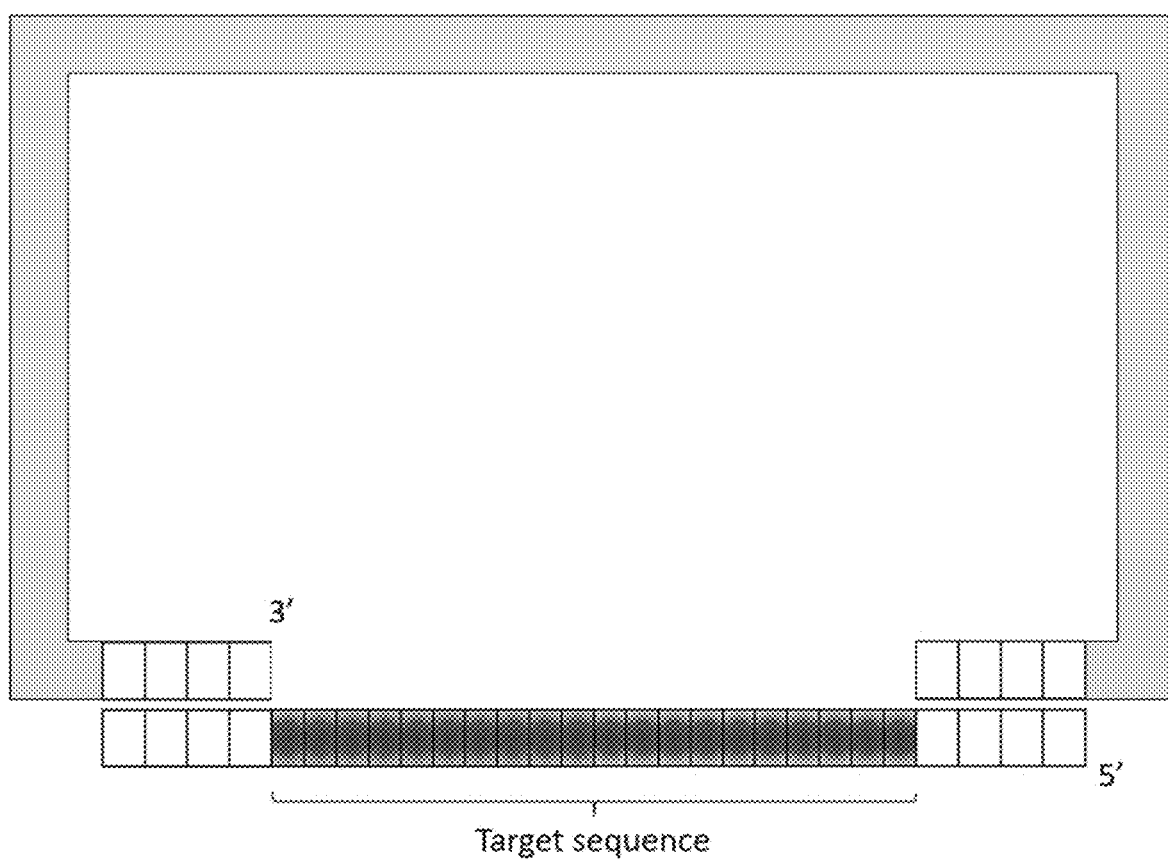
Figure 1C:
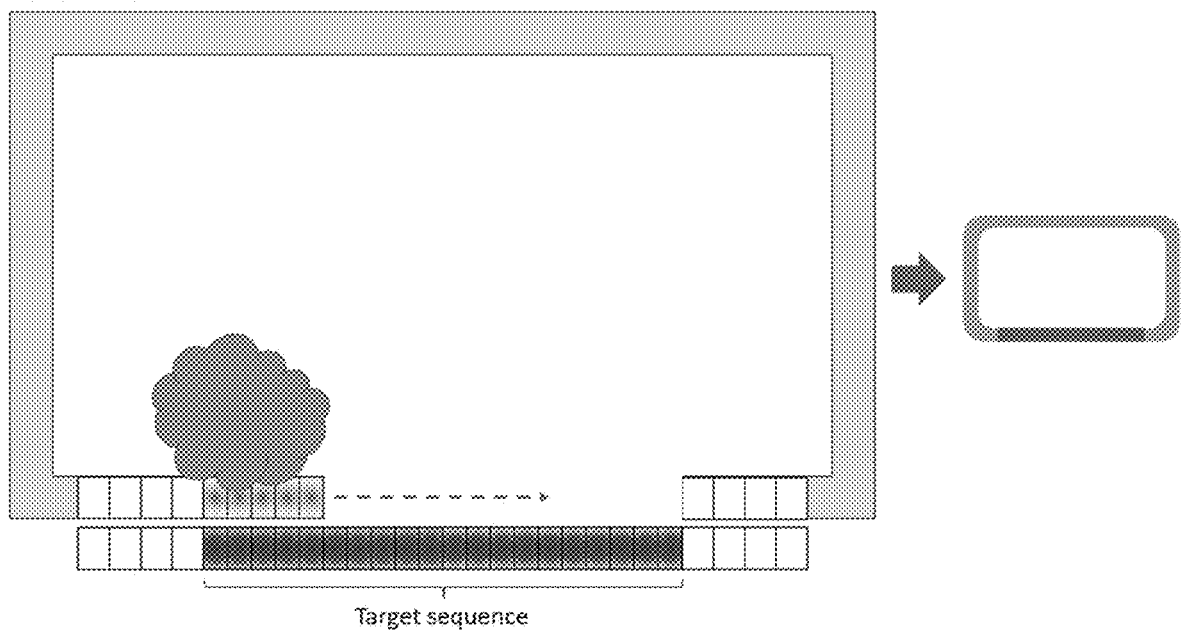
Figure 1D:
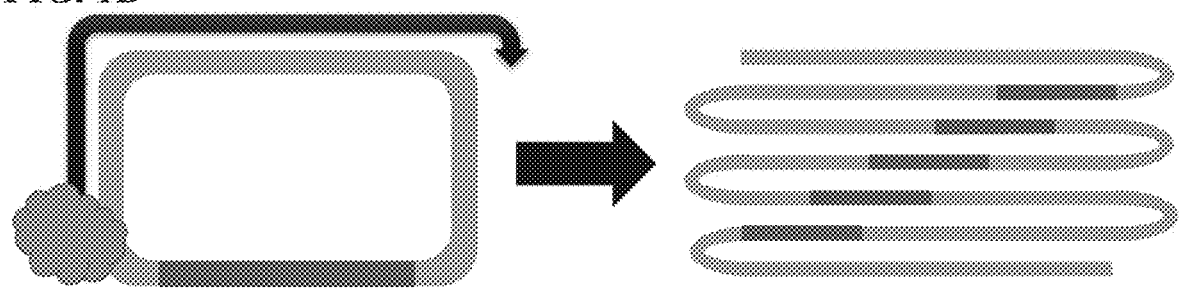
Figure 2:
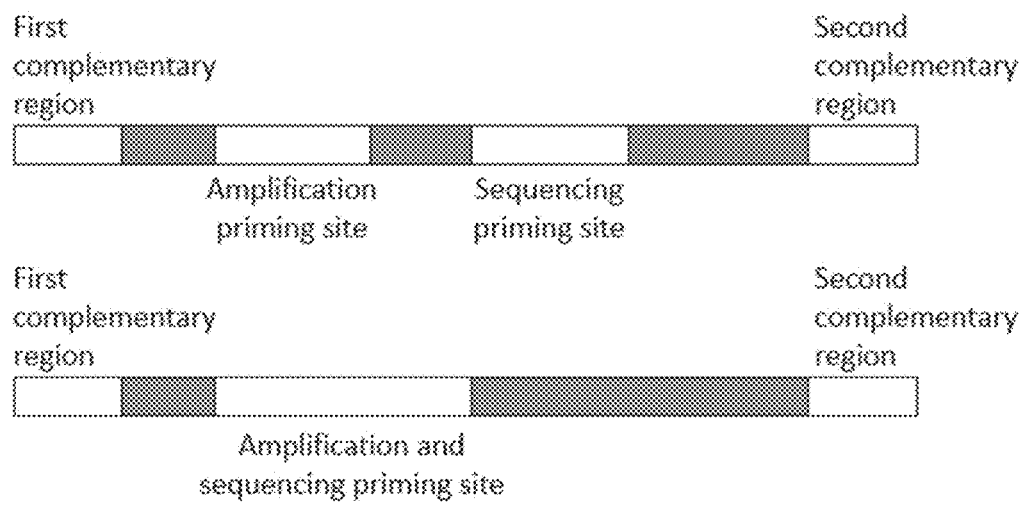
FIG. 2. Schematic illustration of embodiments of the oligonucleotide primer described herein. The oligonucleotide is a single-stranded oligonucleotide containing a first complementary region and a second complementary region (i.e., nucleic acid sequences complementary to nucleic acid sequences flanking the target nucleic acid sequence). In embodiments, the oligonucleotide primer further includes an amplification priming site (i.e., a nucleic acid sequence complementary to an amplification primer) and a distinct sequencing priming site (i.e., a nucleic acid sequence complementary to a sequencing primer). Alternatively, in embodiments, the oligonucleotide primer further includes an amplification priming site and a sequencing priming site that are the same, are partially overlapping, or in which one is internal to the other.

In situ sequencing involves tissue and/or cellular extraction, combined with the fixation and permeabilization of cells, followed by amplification of the target nucleic acid fragments for sequencing. Briefly, cells and their surrounding milieu are attached to a substrate surface, fixed, and permeabilized. Targeted oligonucleotide probes designed for C-V-D-J sequencing are then annealed to complementary regions which flank the nucleic acid of interest or a portion thereof. As shown in FIG. 1B, the oligonucleotide probe hybridizes to regions which flank the target nucleic acid sequence or a portion thereof, referred to as the first and the second complementary regions. In the presence of a polymerase (e.g., a non-strand displacing polymerase), the complement to the target sequence is generated by extending from the first complementary region and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as shown in FIG. 1D. This extension product is then primed with a sequencing primer and subjected to sequencing processes as described herein.

Optionally, one or more nucleotides within the amplification primer sequence, the sequencing primer sequence, and/or the immobilized oligonucleotide primer contains one or more functional moieties (e.g., bioconjugate reactive groups) that serve as attachment points to the cell or the matrix in which the cell is embedded (e.g. a hydrogel). In embodiments, one or more nucleotides within the amplification primer sequence, the sequencing primer sequence, and/or the immobilized oligonucleotide primer contains one or more functional moieties (e.g., bioconjugate reactive groups) that serve as attachment points to complementary bioconjugate reactive groups within the cell (e.g., a protein). In embodiments, a plurality of oligonucleotide primers are provided to the matrix in which the cell is embedded prior to amplification. In embodiments, a plurality of oligonucleotide primers are provided to the matrix in which the cell is embedded concurrently with amplification. In embodiments, the bioconjugate reactive group is located at the 5' or 3' end of the primer. In embodiments, the bioconjugate reactive group is located at an internal position of the primer e.g., the primer contains one or more modified nucleotides, such as aminoallyl deoxyuridine 5'-triphosphate (dUTP) nucleotide(s). In embodiments, the immobilized oligonucleotide primers may be used to aid in tethering the extension product to a confined area and may not be extended. In embodiments, the immobilized oligonucleotide primers may be used to aid in tethering the extension product to a confined area and may also be capable of being extended. For example, one or more immobilized oligonucleotides may be used to aid in tethering the extension product to a localized area and may be extended in an exponential RCA amplification reaction.

Figure 4A:
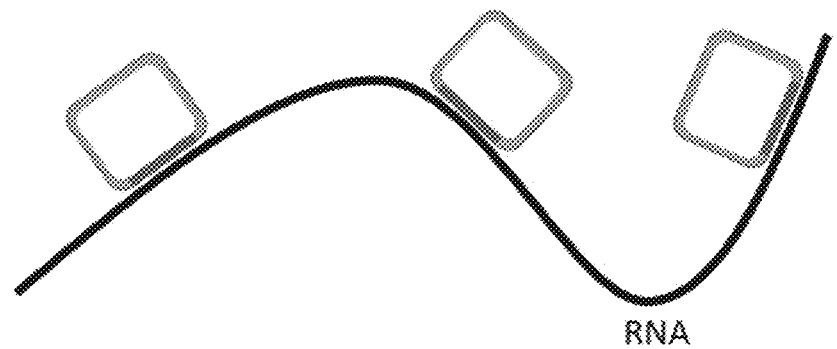
FIGS. 4A-4C illustrate embodiments of sequencing a target RNA sequence in a cell.
Figure 4B:
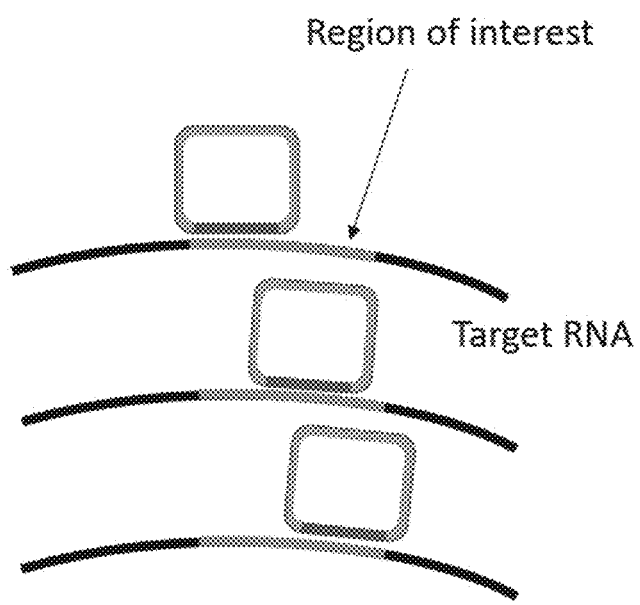
Figure 4C:
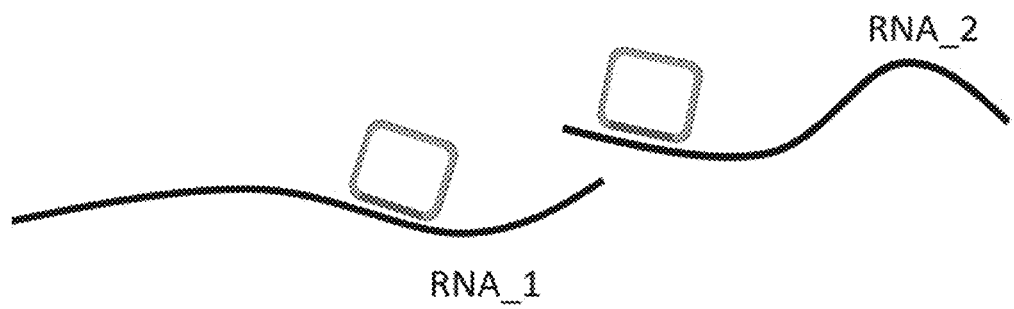

In embodiments, the methods described herein may be utilized for B cell heavy and light chain in situ sequencing by targeting the combination of variable and constant gene segments that make up a given heavy and light chain. These methods provide unique insight into the spatial localization and recombination efforts of a cell's heavy and light chain genes, see for example FIG. 4C. Likewise, the methods can be applied for T-cell receptor (TCR) alpha and beta chain in situ sequencing. The genes encoding alpha (TCRA) and beta (TCRB) chains are composed of multiple non-contiguous gene segments which include V, D, and J segments for TCRB and V and J for TCRA. As with B cell receptor diversity, the enormous diversity of TCR repertoires is generated by random combinatorial gene events. The methods described here can be used to provide a comprehensive in situ view of TCR diversity in intact T cells.

Example 2: Clinical Profiling of Innate Immune Cell Factors

The innate immune system employs germline-encoded pattern-recognition receptors (PRRs) for the initial detection of microbes. PRRs recognize microbe-specific molecular signatures known as pathogen-associated molecular patterns (PAMPs). PRRs activate downstream signaling pathways that lead to the induction of innate immune responses by producing inflammatory cytokines, type I interferon (IFN), and other mediators. These processes trigger immediate host defensive responses such as inflammation and adaptive immune responses critical for the clearance of infecting microbes (Kawasaki and Kawai, 2014, and Akira et al., 2006).

Toll-like receptors (TLRs) are a family of PRRs and part of the first line of defense against invading microbes. Ten different TLRs are expressed to varying degrees in human immune cell subsets, including NK cells, macrophages, B cells, and dendritic cells (DCs) (Nie et al., 2018). TLR activation leads to the production of pro-inflammatory cytokines, triggering an innate immune response and initiating the adaptive immune response (Altfeld and Gale, 2015). Single-cell systems-level analysis of TLR activation has highlighted the cell-to-cell diversity in monocyte responses to TLR ligands, with distinct cytokine patterns correlating to TLR ligand specificity (O'Gorman et al., 2015).

The severe acute respiratory syndrome coronavirus 2 (SARS-CoV-2) resulted in a pandemic in late 2019 and early 2020 with millions of infections of coronavirus disease 2019 (COVID-19). Single-stranded RNA sequences recognized by TLR 7/8 have been identified as PAMPs in the SARS-CoV-2 genome (Moreno-Eutimio et al., 2020). Rare loss-of-function variants of the X-chromosomal TLR7 were recently identified in 4 young male patients with severe COVID-19, indicating a potential genetic predisposition to contract coronavirus infections (van der Made et al., 2020). Utilizing the methods described herein, comprehensive interrogation of innate immune response genes, for example TLR genes in DCs, may be realized and provide insight into the predisposition of an individual to severe pathogen-associated disease and guide clinical decision making. These methods can also provide insight into the single-cell TLR diversity present in an individual.

In situ sequencing involves tissue and/or cellular extraction, combined with the fixation and permeabilization of cells, followed by amplification of the target nucleic acid fragments for sequencing. Briefly, cells and their surrounding milieu are attached to a substrate surface, fixed, and permeabilized using known methods. Targeted oligonucleotide probes designed for TLR sequencing are then annealed to complementary regions which flank the nucleic acid of interest or a portion thereof. As shown in FIG. 1B, the oligonucleotide probe hybridizes to regions which flank the target nucleic acid sequence or a portion thereof, referred to as the first and the second complementary regions. In the presence of a polymerase (e.g., a non-strand displacing polymerase), the complement to the target sequence is generated by extending from the first complementary region and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as shown in FIG. 1D. This extension product is then primed with a sequencing primer and subjected to sequencing processes as described herein and in Example 1.

REFERENCES FOR EXAMPLE 2: Kawasaki T. and Kawai T. Front. Immunol., 2014, 5:461; Akira S. et al. Cell, 2006, 124, 783-801; Nie L. et al. Front. Immunol., 2018, 9:1523; O'Gorman et al. J. Allergy Clin. Immunol., 2015, 136, 1326-1336; Altfeld M. and Gale, Jr. M. Nature Immunol., 2015, 16, 554-562; Moreno-Eutimio M. et al. Microbes Infect., 2020, 22, 226-229; and Van der Made C. et al. JAMA, 2020, 324:7.

Example 3: Metagenomics and Profiling Bacteria

The study of bacterial phylogeny and taxonomy by analyzing the 16S rRNA gene has become popular among microbiologists due to the need to study the diversity and structure of microbiomes thriving in specific ecosystems. Due to its presence in almost all bacteria, the 16S rRNA gene is a core component of the 30S small subunit of prokaryotes. The 16S sequence contains ten conserved (C) regions that are separated by nine variable (V1-V9) regions, wherein the V regions are useful for taxonomic identification. Due to limitations in previous NGS platforms, the entirety of the 16S gene (approximately 1,500 bp) is difficult to accurately sequence.

Clever design of primers have been reported and used for amplifying specific V regions of 16S rRNA; for example, the third, fourth, and fifth variable regions (V3, V4 and V5 regions, respectively) have been used for studies where classification and understanding phylogenic relationships is important (see for example, Baker G. C., et al J. of Microbiological Methods, V55 (2003), 541-555; and Wang, Y., et al. (2014). PloS one, 9(3), e90053). While the information gained from sequencing the V3 or V4 region is valuable, no single variable region can differentiate among all bacteria. For example, the V1 region has been demonstrated to be particularly useful for differentiating among species in the genus *Staphylococcus*, whereas V2 distinguished among Mycobacterial species and V3 among *Haemophilus* species (Chakravorty, S., et al (2007). Journal of microbiological methods, 69(2), 330-339). It would therefore be very beneficial to be able to sequence the entirety of the 16S gene. The methods described herein provide a new method for in situ sequencing of the 16S rRNA gene in its entirety, including the constant and nine variable regions, across an intact microbial population.

Figure 3A:
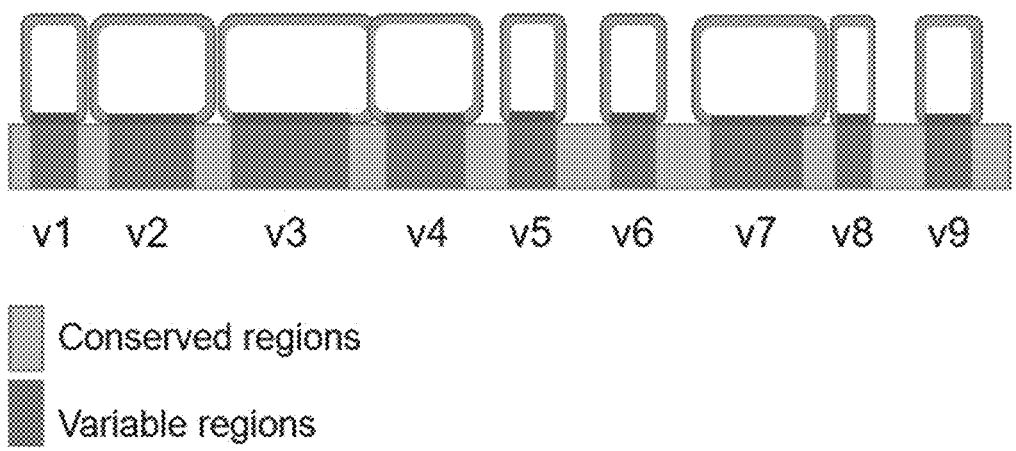
FIGS. 3A-3B illustrates a 16S rRNA variable and conserved gene segment. The 16S sequence contains ten conserved (C) regions that are separated by nine variable (V1-V9) regions, wherein the V regions are useful for taxonomic identification. Using methods described herein to sequence noncontiguous nucleic acid sequences of the same target nucleic acid provides valuable insight into the entirety of the 16S rRNA gene. Above the variable regions in FIG. 3A are the circularized oligonucleotides generated according to the methods described herein.
Figure 3B:
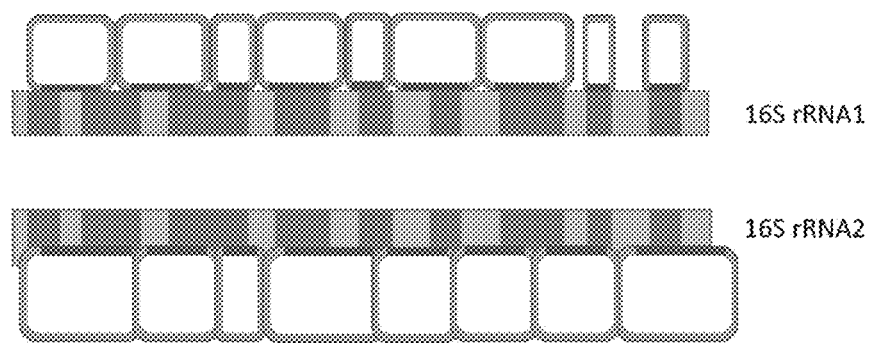

Briefly, a population of microbial cells is attached to a substrate surface, fixed, and permeabilized according to known methods in the art. Targeted oligonucleotide probes designed for 16S rRNA sequencing are then annealed to the nucleic acid region of interest. By careful primer design, the targeted oligonucleotide probes can sequence only the variable regions, or alternatively, the targeted oligonucleotide probes can overlap with conserved regions (see for example FIG. 3B). As shown in FIG. 1B, the oligonucleotide probe hybridizes to regions which flank the target nucleic acid sequence or a portion thereof, referred to as the first and the second complementary regions. In the presence of a polymerase (e.g., a non-strand displacing polymerase), the complement to the target sequence is generated by extending from the first complementary region and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as shown in FIG. 1D. FIGS. 3A-3B illustrates a 16S rRNA variable and conserved gene segment. The 16S sequence contains ten conserved (C) regions that are separated by nine variable (V1-V9) regions, wherein the V regions are useful for taxonomic identification. Using methods described herein to sequence noncontiguous nucleic acid sequences of the same target nucleic acid provides valuable insight into the entirety of the 16S rRNA gene. Above the variable regions are the circularized oligonucleotides generated according to the methods described herein and in Example 1.

Example 4: Detection of Oncogenic Gene Variants

The concept of precision oncology aims to address the need for molecular characterization of individual tumors to enable tailored treatment for each patient. Intratumoral heterogeneity, evident from the varied therapeutic sensitivity existing in multiple subclones from within the same tumor, has made the application of precision oncology more difficult (McGranahan and Swanton, 2017).

Breast cancer has been reported to display both inter- and intra-tumoral genetic heterogeneity with thousands of different mutations uniquely combined in each tumor and subclone (Nik-Zainal et al., 2016, Barretina et al., 2012). Breast cancer diagnostics typically relies on a combined evaluation of histopathogy including tumor grade and immunohistochemical staining of ER, PR, HER2, and Ki67. Additionally, complementary molecular analyses such as NGS, Mammaprint (Wang et al., 2005), OncotypeDX (Paik et al., 2004), and PAM50 (Parker et al., 2009) are done on bulk cell lysates from homogenized tissues. Bulk tissue-based analytical approaches do not provide high levels of resolution into the effects of genetic heterogeneity on complex tumor cell interactions such as epithelial-to-mesynchymal transition, angiogenesis, and invasiveness. Spatially resolving techniques like in situ sequencing as described herein allow for in-depth characterization of the different cellular niches and their signaling pathways within tumor tissue. This spatial information, combined with classical histological diagnostics, can couple molecular features directly to tumor morphology (Svedlund et al., 2019).

Figure 6:
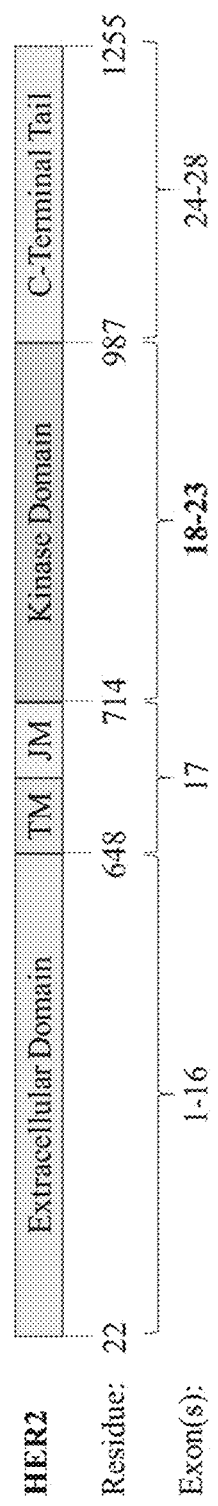
FIG. 6 Illustrates the HER2 protein domains and corresponding exons. The extracellular domain is separated from the kinase domain by the transmembrane (TM) and juxtamembrane (JM) domains. The kinase domain (amino acid residues 714-987 and exons 18-23) harbors the majority of known anti-HER2 therapy resistance mutations. Using methods described herein to sequence the nucleic acid sequence of the kinase domain and adjacent regions provides clinical insight into the presence or development of resistance mutations in the HER2 gene of a cancer patient.

HER2 is a driver gene in breast cancer, and HER2 amplification is the predictive marker and molecular target of anti-HER2 agents such as trastuzumab, pertuzumab, or lapatinib (Montemurro and Scaltriti, 2014). Approximately 20-25% of all breast cancers overexpress HER2 (referred to as HER2-positive) and are linked to an aggressive phenotype (Asif et al., 2016). Oncogenic mutations in HER2 have been suggested to contribute to anti-HER2 therapy resistance. The HER2 gene and its domains and corresponding exons are shown in FIG. 6. Several HER2 mutations in the tyrosine-kinase domain spanning exon 20 have been described as having an impact on the clinical sensitivity to trastuzumab and lapatinib treatment (Robichaux et al., 2018 and Gaibar et al., 2020). Having an in situ transcriptomic profile of a HER2-positive breast cancer with the methods described herein would not only provide spatial expression data, but also inform clinicians regarding the prevalence of mutant oncogene subtypes, such as treatment-resistant HER2 cells.

The methods described herein provide a novel in situ sequencing approach for obtaining detailed genomic information from tumor tissue, connecting genetic heterogeneity to pathological manifestation of a cancer, for example HER2 exon 20 expression and sequence identity in breast cancer tissues and cells. Briefly, a tumor tissue section is attached to a substrate surface, fixed, and permeabilized according to known methods in the art. Targeted oligonucleotide probes designed for HER2 exon 20 sequencing are then annealed to complementary regions which flank the nucleic acid of interest or a portion thereof. As shown in FIG. 1B, the oligonucleotide probe hybridizes to regions adjacent (i.e., the regions that flank the target nucleic acid sequence, or a portion thereof) to the target nucleic acid sequence, referred to as the first and the second complementary regions. In the presence of a polymerase (e.g., a non-strand displacing polymerase), the complement to the target sequence is generated by extending from the first complementary region and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as shown in FIG. 1D. This extension product is then primed with a sequencing primer and subjected to sequencing processes as described herein, thereby providing a high-resolution view of molecular features that can be combined with additional histological findings for clinical decision-making.

As an alternative or companion diagnostic to a tumor tissue biopsy, the methods described herein may also be applied to isolated circulating tumor cells (CTCs). CTCs are the rare metastatic cancer cells shed from the primary tumor into the circulatory system that can ultimately lead to the formation of metastases (Rossi and Zamarchi, 2019). Briefly, CTCs are enriched from whole blood using methods known in the art, then are attached to a substrate surface, fixed, and permeabilized. Targeted oligonucleotide probes designed for genes of interest, e.g., a HER2 gene, a BCL2 gene, an ERG gene, a PTEN gene, are then annealed to flanking complementary regions of the nucleic acid of interest or a portion thereof. Extension, ligation, amplification, and sequencing are then performed as described herein and in Example 1. These methods would help distinguish CTCs from contaminating blood cells in situ and provide insight into tumor molecular heterogeneity.

Example 5: Monitoring Transcriptional Response to Pharmacological Agents

Large projects such as the Cancer Cell Line Encyclopedia (CCLE, Barretina et al., 2012) and Genomics of Drug Sensitivity in Cancer (GDSC, Garnett et al., 2012) have analyzed hundreds of cancer cell lines and generated data on the genotypes and cellular responses to pharmacological treatment. Additional work has combined multi-omics approaches (e.g., RNA-seq and ATAC-seq) from drug-treated lung cancer cell lines to profile cellular responses and identify novel drug targets (Suzuki et al., 2019). Similar approaches using bulk and single-cell transcriptomics in fibroblasts and mononuclear phagocytes, challenged with immune stimuli such as a genetically modifying agent, revealed that transcriptionally diverging genes like cytokines and chemokines varied in expression across cells (Hagai et al., 2018). Studies such as these have taken an initial step at mapping the cellular response to therapeutic agents but lack resolution into the dynamic cellular and subcellular heterogeneity of the cellular programs governing downstream physiological effects.

In gastric cancer (GC), genomic profiling is used to define clinical subtypes based on mutational status of oncogenes such as ERBB2, KRAS, TP53, and PIK3CA (Ho and Tan, 2019). Tumor heterogeneity has profound implications for therapy selection. In a clinical trial testing FGFR2 inhibition in GC, durable responses were observed only in high-level FGFR2 clonally amplified tumors, as assessed by FISH-based in situ heterogeneity mapping (Pearson et al., 2016). A comparison of paired FGFR2 expression at baseline and 15 days post-treatment further showed significant decreases in FGFR2 mRNA only in the sub-clonal, heterogeneously amplified tumor, possibly reflecting clonal selection of non-amplified compartments as a result of therapeutic pressure. The sequencing methods described herein can be applied to the molecular profiling of a GC tumor to monitor whether FGFR2 expression is perturbed during therapy.

Briefly, tumor cells obtained from a GC patient before, during, and/or after pharmacological treatment are attached to a substrate surface, fixed, and permeabilized according to known methods in the art. Targeted oligonucleotide probes for FGFR are then annealed to the nucleic acid of interest. As shown in FIG. 1B, the oligonucleotide probe hybridizes to regions adjacent (i.e., flanking the FGFR nucleic acid sequence) to the target nucleic acid sequence, referred to as the first and the second complementary regions. In the presence of a polymerase (e.g., a non-strand displacing polymerase), the complement to the target sequence is generated by extending from the first complementary region and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as shown in FIG. 1D. This extension product is then primed with a sequencing primer and subjected to sequencing processes as described herein and in Example 1.

Such methods may be applied to assess whether a patient being treated for any physiological or psychological condition that requires a pharmacological agent has a transcriptional response in a target cell type that may be indicative of the clinical efficacy of the treatment. These can also provide temporal information for patients under short- or long-term drug treatment to provide relevant clinical information, for instance, gene signatures indicative of drug resistance. Additionally, the methods herein may be used to detect genetic rearrangements at the RNA level, such as splice variants, gene fusions, and inter- and intrachromosomal translocations, both at baseline and during/after treatment of a subject with a pharmacological agent (e.g., a genetically modifying agent). The presence of such genetic rearrangements can also be informative with regards to drug resistance. Less-invasive options for such a diagnostic tool include isolation of CTCs (Rossi and Zamarchi, 2019), or isolation of immune cells from whole blood or bodily fluids.

REFERENCES FOR EXAMPLES 4 and 5: 1. McGranahan N. and Swanton C. Cell, 2017, 168, 613-628; 2. Nik-Zainal S. et al. Nature, 2016, 534, 47-54; 3. Barretina J. et al. Nature, 2012, 483, 603-607; 4. Wang Y. et al. Lancet, 2005, 365, 671-679; 5. Paik S. et al. New Engl. J. Med., 2004, 351, 2817-2826; 6. Parker J. et al. J. Clin. Oncol., 2009, 27, 1160-1167; 7. Svedlund J. et al. EBioMedicine, 2019, 48, 212-223; 8. Montemurro F. and Scaltriti M. J. Pathology, 2014, 232, 219-229; 9. Asif H. et al. Asian Pac. J. Cancer P., 2016, 17, 1609-1615; 10. Gaibar M. et al. J. Oncol., 2020, 2020, 1-13; 11. Garnett M. et al. Nature, 2012, 483, 570-575; 12. Suzuki A. et al. Sci. Rep., 2019, 9, 19529; 13. Hagai T. et al. Nature, 2018, 563, 197-202; 14. Ho S. and Tan P. Cancer Sci., 2019, 110, 3405-3414; 15. Pearson A. et al. Cancer Discov., 2016, 6, 838-851; 16. Rossi E. and Zamarchi R. Frontiers Genetics, 2019, 10, 958; and 17. Robichaux J. et al. Nat. Med., 2018, 24, 638-646.

Example 6: Profiling Genome Editing Efficiency

The evolution of gene editing towards clinical practice has developed through recent advancements in programmable nucleases, such as zinc-finger nucleases (ZFNs), transcription activator-like effector nucleases (TALENs), and clustered regularly interspaced short palindromic repeat (CRISPR)-Cas-associated nucleases. Targeted DNA alterations begin with the generation of nuclease-induced double-stranded breaks (DSBs), which lead to the stimulation of DNA recombination mechanisms in mammalian cells (Kosicki et al., 2018). Nuclease-induced DNA DSBs can be repaired by one of the two major mechanisms present in eukaryotic cells: non-homologous end joining (NHEJ) and homologous recombination (HR), resulting in gene disruptions or targeted integration, respectively (Kass and Jasin, 2010).

The CRISPR-Cas systems are divided into two classes based on the structural variation of the Cas genes and their organization style. Specifically, class 1 CRISPR-Cas systems consist of multiprotein effector complexes, where class 2 systems includes only a single effector protein; at least six CRISPR-Cas types and 29 subtypes have been reported (Makarova et al., 2015). At present, the most frequently used subtype of CRISPR system is the type 2 CRISPR/Cas9 system, which depends on a single Cas protein from *Streptococcus pyogenes* (SpCas9) targeting DNA sequences (Jiang et al., 2013). A single-stranded guide RNA (sgRNA) and a Cas9 endonuclease form a targeting complex, wherein the sgRNA binds to the target sequence and Cas9 precisely cleaves the DNA to generate a DSB and subsequently activate cellular repair programs. Conveniently, changing the sgRNA sequence allows the targeting of new sites, without requiring changes to the Cas9 protein (Li et al., 2020).

Specific delivery methods have been developed for targeting both Cas9 and sgRNAs directly to the organ of interest in vivo, including direct transfection, lentiviral and adeno-associated virus (AAV)-based transduction, and nanoparticle delivery (Tschaharganeh et al., 2016). Cells may also be isolated from a patient to be treated, edited, and then re-engrafted back to the patient. Such an approach is used in the preparation of chimeric antigen receptor (CAR) T cells for cancer immunotherapy, wherein the patient's T cells are isolated, reengineered and modified with tumor-antigen-specific receptors and costimulating molecules, transduced with a CAR viral vector, amplified, and then infused back into the patient (Li et al., 2020). Furthermore, the development of allogeneic universal "off-the-shelf" CAR T cells has been demonstrated effectively using a one-shot CRISPR protocol to knockout endogenous TCR and HLA class 1 molecules (Ren et al., 2017).

Determining whether the cell of interest has been successfully targeted by a genome editing endonuclease is traditionally performed via bulk harvesting of cell lysate and analysis of total genomic material (Cromer et al., 2018). Some of the current challenges in therapeutic targeting involve increasing the specificity of gene correction, improving the efficiency of nuclease editing, and optimizing the delivery systems (Li et al., 2020). By using the in situ sequencing methods described herein, high-resolution information is obtained to decipher the effectiveness of a genome editing treatment, for example, the production of allogeneic CAR T cells.

Briefly, a population of T cells is subjected to a genome editing technique, for example CRISPR/Cas9, to knockout the TCR and HLA class 1 loci. The cells are then attached to a substrate surface, fixed, and permeabilized according to known methods in the art. Targeted oligonucleotide probes for the TCR and HLA class 1 loci are then annealed to the nucleic acid of interest. As shown in FIG. 1B, the oligonucleotide probe hybridizes to regions adjacent to the target nucleic acid sequence (i.e., the complementary regions that flank the target nucleic acid sequence), referred to as the first and the second complementary regions. In the presence of a polymerase (e.g., a non-strand displacing polymerase), the complement to the target sequence is generated by extending from the first complementary region and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as shown in FIG. 1D. This extension product is then primed with a sequencing primer and subjected to sequencing processes as described herein and in Example 1.

Example 7: Categorization of Neural Cell Diversity

The mammalian nervous system is thought to contain thousands of neural cell types (Bota and Swanson, 2007). Systematic classification of all mammalian neurons is a key goal towards deconstructing the nervous system into its basic components. The glutamatergic excitatory neurons in the cortex are often classified by their projection properties into, for example, intratelencephalic neurons, pyramidal tract neurons, and cortico-thalamic projection neurons (Yamawaki and Shepherd, 2015). Single-cell transcriptomics studies have revealed a high diversity of cells in the brain, with up to hundreds of cell types within individual cortical regions (Saunders et al., 2018 and Tasic et al., 2018).

The most widely employed methods for molecular characterization of neurons at the single-cell level are immuno-labeling, RNA in situ hybridization (ISH), and transgenic approaches, which have been used in large-scale classification projects such as the Allen Brain Atlas (ABA) and the Gene Expression Nervous System Atlas (GENSAT) (Poulin et al., 2016). Recently, spatially resolved transcriptomic methods, such as multiplexed error-robust fluorescence in situ hybridization (MERFISH), have been used to perform in situ gene expression profiling and spatial mapping of individual cells and map their spatial organization in the mouse primary motor cortex (MOp) (Zhang et al., 2020). The MOp has been designated by the BRAIN Initiative Cell Census Network (BICCN) as the initial target for comprehensive cell mapping in the brain (Ecker et al., 2017).

Using the methods as described herein, it is possible to obtain a sequence-level spatial map of the MOp, providing a complete definition of the resident cell population. Briefly, a section of MOp tissue is excised by methods known in the art. The cells are then attached to a substrate surface, fixed, and permeabilized according to known methods in the art. Targeted oligonucleotide probes designed to probe known neuronal factors are then annealed to the nucleic acid of interest. As shown in FIG. 1B, the oligonucleotide probe hybridizes to regions adjacent to the target nucleic acid sequence (i.e., regions which flank the gene of interest), referred to as the first and the second complementary regions. In the presence of a polymerase (e.g., a non-strand displacing polymerase), the complement to the target sequence is generated by extending from the first complementary region and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as shown in FIG. 1D. This extension product is then primed with a sequencing primer and subjected to sequencing processes as described herein and in Example 1.

REFERENCES FOR EXAMPLES 6 and 7: Kosicki M. et al. Nat. Biotechnol., 2018, 36, 765-771; Kass E. and Jasin M. FEBS Lett., 2010, 584, 3703-3708; Makarova K. et al. Nat. Rev. Microbiol., 2015, 13, 722-736; Jiang W. et al. Nat. Biotechnol., 2013, 31, 233-239; Li H. et al. Signal Transduct. Target Ther., 2020, 5, 1-23; Tschaharganeh D. et al. FEBS J., 2016, 283, 3194-3203; Ren J. et al. Oncotarget, 2017, 8, 17002-17011; Cromer M. et al. Mol. Ther., 2018, 26, 2431-2442; Bota M. and Swanson L. Brain Res. Rev., 2007, 56, 79-88; Yamawaki N. and Shepherd G. J. Neurosci., 2015, 35, 2293-2307; Saunders A. et al. Cell, 2018, 174, 1015-1030; Tasic B. et al. Nature, 2018, 563, 72-78; Poulin J. et al. Nat. Neurosci., 2016, 19, 1131-1141; Zhang M. et al. bioRxiv, 2020, 2020.06.04.105700; and Ecker J. et al. Neuron, 2017, 96, 542-557.

Example 8: Profiling Tumor Infiltrating Lymphocytes in a Biopsy

The assessment of tumor infiltrating lymphocytes (TILs) in histopathological specimens can provide important prognostic information in diverse solid tumor types and may also be of value in predicting response to treatments. The altered protein products in cancer cells can function as neoantigens and elicit an immune response (Hendry et al., 2017). This immune response can lead to perturbations in the tumor microenvironment that may play a role in cancer progression and outcome (Coussens et al., 2013). Specifically, the inflammatory tumor microenvironment may pose an obstacle to the efficacy of novel cancer immunotherapies, such as engineered chimeric antigen receptor (CAR) NK and T cells. The infiltration of CAR NK and CAR T cells into a tumor is a critical step in exerting anti-tumor effects that can be inhibited by various features of the tumor microenvironment, including concentrated blood vessels and extracellular matrix (Ma et al., 2019).

CAR cells that target the B-cell antigen CD19 are being investigated in various clinical trials for the treatment of advanced B-cell lymphoma, among other hematological cancers. Next-generation CARs, such as FT596 universal NK immunotherapy, have various engineered anti-tumor functional modalities to overcome the tumor microenvironment and synergistically exert anti-tumor activity (Nayyar et el, 2019). In the case of FT596, one such feature is a CAR optimized for NK cell biology with a NKG2D transmembrane domain, a 2B4 co-stimulatory domain, and a CD3-zeta signaling domain for targeting CD19. In a clinical setting, assessing the extent of TILs would be a significant barometer of treatment efficacy and provide insight into the progression of oncolytic activity, allowing clinicians to learn which antigens are being recognized or what T cell types are capable of infiltrating a tumor, presenting unique opportunities for immunotherapies.

The methods described herein provide a novel in situ sequencing approach for profiling the tumor microenvironment at a transcriptional level, for example, to determine the presence, magnitude, and identity of TILs (e.g., native or allogenic TILs). Briefly, a tumor tissue section is attached to a substrate surface, fixed, and permeabilized according to known methods in the art. Targeted oligonucleotide primers designed for sequencing the CAR variable region are then annealed to complementary regions which flank the nucleic acid of interest or a portion thereof. As shown in FIG. 1B, the oligonucleotide primer hybridizes to regions adjacent (i.e., the regions that flank the target nucleic acid sequence, or a portion thereof) to the target nucleic acid sequence, referred to as the first and the second complementary regions. In the presence of a polymerase (e.g., a non-strand displacing polymerase), the complement to the target sequence is generated by extending from the first complementary region and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as shown in FIG. 1D. This extension product is then primed with a sequencing primer and subjected to sequencing processes as described herein and in Example 1, thereby providing a high-resolution view of infiltrating CAR NK and/or CAR T cell molecular features that can be combined with additional histological and immunohistochemistry modalities to guide clinical decision-making.

REFERENCES FOR EXAMPLE 8: Hendry et al. Adv. Anat. Pathol., 2017, 24, 235-251; Coussens et al. Science, 2013, 339, 286-291; Ma et al. Int. J. Biol. Sci., 2019, 15, 2548-2560; and Nayyar et al. Frontiers Oncol., 2019, 9, 51.

Example 9: Profiling the States of the Tuberculosis Granuloma

Tuberculosis (TB) is one of the top ten causes of death worldwide and the leading cause of death from a single infectious agent (Chakaya J et al. Int. J. Infect. Dis. 2021; S1201-9712(21): 00193-4). TB is caused by the pathogenic bacteria species *Mycobacterium tuberculosis* (MTb), which infects cells of the upper airway of an organism. Macrophages internalize invading MTb cells by phagocytosis, which are then believed to reside within the endosomes of the macrophage. The immune system attempts to isolate the infection and aggregates infected macrophages into a granuloma. In a minority of cases, the integrity of the granuloma is compromised and MTb cells infect other parts of the lung and/or enter the lymph system and reach other organs or systems, rapidly deteriorating patient outcomes. Existing clinical diagnostics, such as Cepheid's Xpert® MTB/RIF, focus on differentiating whether a patient presenting with symptoms of TB is infected with a multi-drug resistant and rifampicin resistant strain, which simultaneously detects both. Such diagnostic tests provide key decision metrics for the type of isolation and treatment that would be most efficacious for a patient. Tests such as these, though useful for point-of-case diagnostic purposes, do not provide information on the factors regulating the development of the granuloma. Rifampicin resistance may occur alone or in association with resistance to isoniazid and other drugs (Steingart K R et al. Cochrane Database Syst. Rev. 2014; 2014 (1): C009593). Rifampicin inhibits bacterial DNA-dependent RNA polymerase, encoded by the RNA polymerase gene rpoB, and resistance has mainly been associated with mutations in an 81-base pair region of the rpoB gene, including the mutations Q513P, Q513K, H256R, S531L, or S531W (Al-Mutairi N M et al. BMC Infect. Dis. 2019; 19: 3). Resistance to ethambutol (EMB), isoniazid (INH), and pyrazinamide (PZA) include mutations in the embB, inhA, and pncA genes, respectively. Mutations in one or more of these genes are frequently found in multi-drug resistant MTb strains.

It is known that cytokines such as IFNγ, TGF-beta and other signaling systems are involved in the establishment and maintenance of the TB granuloma (Gem B H et al. Cell Host Microbe. 2021; 29(4): 594-606). In situ sequencing of TB granulomas in lungs from mice at different times after infection have shown that the necrotic centers of encapsulated granulomas express transcripts associated with immunosuppression (Foxp3, IL10), whereas those transcripts in the granuloma periphery associate with activated T cells and macrophages (Carow B et al. Nature Comm. 2019; 10: 1823). Considering these recent discoveries, there is still a need for improved models of the factors that control granuloma integrity, maintenance, and evolution over time. Developing an improved understanding of the factors regulating an individual patient's infection and the mechanisms driving disease progression may aid earlier intervention and lead to targeted therapeutics and improved patient outcomes.

The methods described herein provide a novel in situ sequencing approach for profiling the TB granuloma at a transcriptional level enabling scientists and clinicians to monitor the disease state, for example, to determine how its regulation, integrity, and function evolve over time. Briefly, a TB granuloma sample (e.g., from a subject biopsy or an in situ TB model) is attached to a substrate surface, fixed, and permeabilized according to known methods in the art. Optionally, the sample is cleared (e.g., digested) of proteins, lipids, or proteins and lipids. The granuloma sample is obtained from one or more regions of the granuloma, for example, the necrotic center and the granuloma rim. Samples are obtained from the subject at various time points of TB infection, for example, before symptoms appear, early in disease progression (about 3 weeks post-infection), and late in disease progression (about 8 to 12 weeks post-infection). Targeted oligonucleotide primers designed for sequencing are then annealed to complementary regions which flank the nucleic acid or a portion thereof (e.g., rpoB, IFNγ, TGF-beta, FOX3P and/or IL10 genes). As shown in FIG. 1B, the oligonucleotide primer hybridizes to regions adjacent (i.e., the regions that flank the target nucleic acid sequence, or a portion thereof) to the target nucleic acid sequence, referred to as the first and the second complementary regions. In the presence of a polymerase (e.g., a non-strand displacing polymerase), the complement to the target sequence is generated by extending from the first complementary region and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as shown in FIG. 1D. This extension product is then primed with a sequencing primer and subjected to sequencing processes as described herein and in Example 1, thereby providing a high-resolution view of granuloma molecular features that can be combined with additional histological and immunohistochemistry modalities to guide clinical decision-making.

Example 10: Differentiation of Triple Negative Breast Cancer States

Triple negative breast cancer (TNBC) is a subtype of breast cancer that accounts for 15-20% of all breast cancers and is characterized by loss of progesterone receptor, estrogen receptor, and epidermal growth factor receptor (HER2). Patients diagnosed with TNBC have the highest risk of metastasis of any breast cancer and have a 40-80% risk of recurrence after therapy. TNBCs are highly heterogeneous and there is evidence that suggests this heterogeneity contributes to resistance to chemotherapy and relapse (Garrido-Castro A C et al. Cancer Discov. 2019; 9(2): 176-198). Development of resistance to chemotherapy appears to occur through epigenetic changes that modify the activity of key regulators of cell state and produce "persister" cells that can survive prolonged treatment with chemotherapy (Risom T et al. Nat. Commun. 2018; 9(1): 3815 and Echeverria G V et al. Sci. Transl. Med. 2019; 11(488): eaav0936). There is a lack of understanding regarding the cellular factors that lead to the production and maintenance of these persister cells. Specifically, there is a clinical need to differentiate TNBC states and state transitions in response to chemotherapeutic treatment (e.g., doxorubicin combined with cyclophosphamide).

The methods described herein provide a novel in situ sequencing approach for profiling TNBC tumors at a transcriptional level and monitor the disease state, for example, to determine how different tumors evolve over time and in response to pharmacological treatment. Briefly, tumor cells obtained from a TNBC patient (or from a patient-derived xenograft model) before, during, and/or after pharmacological treatment (e.g., chemotherapy) and are attached to a substrate surface, fixed, and permeabilized according to known methods in the art. Optionally, the sample is cleared (e.g., digested) of proteins, lipids, or proteins and lipids. Targeted oligonucleotide primers designed for sequencing are then annealed to complementary regions which flank the nucleic acid of interest or a portion thereof (e.g., genes characteristic in a chemotherapeutic resistance signature such as TNF, VEGFA, IL-6, TNFSF10, CLU, ABCC6, EGR1, SNAIL ABCC3, EPHX1, FASN, CXCL1, IL24, JUNB, and/or TP53I11 (see, e.g., Ciocan-Cartita C A et al. J. Exp. Clin. Cancer Res. 2020; 39(1): 241, and Nedeljkovic M et al. Cells. 2019; 8(9): 957)). As shown in FIG. 1B, the oligonucleotide primer hybridizes to regions adjacent (i.e., the regions that flank the target nucleic acid sequence, or a portion thereof) to the target nucleic acid sequence, referred to as the first and the second complementary regions. In the presence of a polymerase (e.g., a non-strand displacing polymerase), the complement to the target sequence is generated by extending from the first complementary region and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as shown in FIG. 1D. This extension product is then primed with a sequencing primer and subjected to sequencing processes as described herein and in Example 1, thereby providing temporal information for patients under short- or long-term drug treatment to provide relevant clinical information, for instance, gene signatures indicative of drug resistance that can be combined with additional histological and immunohistochemistry modalities to guide clinical decision-making.

Example 11: Profiling the Glioblastoma Multiforme Tumor Microenvironment

Glioblastoma multiforme (GBM) is an extremely aggressive brain tumor and one of the deadliest forms of cancer, with a two-year survival rate of less than 1 in 3 (Aldape K et al. Nat. Rev. Clin. Oncol. 2019; 16(8): 509-520). Classification of GBM based on specific gene mutations (isocitrate dehydrogenase-1) or DNA methylation (promoter region of the MGMT DNA repair enzyme) provides an accurate prognosis but has yielded limited clinical improvement in patient outcomes. Defining features of GBM include infiltration of activated microglia and an abundant variety of immune cells not normally found in the brain, e.g., monocyte-derived macrophages, neutrophils, and T-cells (Klemm F et al. Cell. 2020; 181(7): 1643-1660). Understanding the complex cellular milieu of the GBM tumor microenvironment will shed crucial insight into the development of targeted therapeutics.

Single cell profiling of RNA and protein in patient biopsies have recently revealed as many as 14 distinct transcriptional states of microglia within the tissue and tumor microenvironment (Sankowski R et al. Nat. Neurosci. 2019; 22(12): 2098-2110). The fact that intratumor cell heterogeneity is strongly correlated with patient survival underscores the need to determine how tumor and healthy cell functions are coordinated at the tissue level, and how the tumor microenvironment responds to therapeutic intervention (Patel A P et al. Science. 2014; 344(6190): 1396-401). A major obstacle to treating GBM is recurrence after tumor resection. The ability to accurately define and predict tissue state transitions after removal of the tumor would pave the way for novel therapeutics with greater efficacy and reduced toxicity. Defining tissue states based on the properties of tissue resident and infiltrating leukocytes may also provide complementary information regarding the tissue microenvironment.

The methods described herein provide a novel in situ sequencing approach for profiling the GBM tumor microenvironment at a transcriptional level and monitor the disease state, for example, to accurately define and predict tissue state transitions after removal of the tumor and/or in response to pharmacological treatment. Briefly, tumor and/or surrounding cell sample is obtained from a GBM patient (or from a patient-derived xenograft model) before, during, and/or after tumor resection/pharmacological treatment (e.g., chemotherapy) and are attached to a substrate surface, fixed, and permeabilized according to known methods in the art. Optionally, the sample is cleared (e.g., digested) of proteins, lipids, or proteins and lipids. Targeted oligonucleotide primers designed for sequencing are then annealed to complementary regions which flank the nucleic acid of interest or a portion thereof (e.g., cell-specific factors to identify infiltrating lymphocyte, microglia, neutrophils, macrophages, etc. (see, e.g., Huang S et al. Front. Immunol. 2020; 11: 585034)); or, a microglial homeostatic gene, e.g., CX3CR1, TMEM119, CSF1R, P2RY12, P2RY13, SELPLG, GLUT5, CD64, HLA-DR, TREM2, APOE, GPR56 and/or MARCKS). As shown in FIG. 1B, the oligonucleotide primer hybridizes to regions adjacent (i.e., the regions that flank the target nucleic acid sequence, or a portion thereof) to the target nucleic acid sequence, referred to as the first and the second complementary regions. In the presence of a polymerase (e.g., a non-strand displacing polymerase), the complement to the target sequence is generated by extending from the first complementary region and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as shown in FIG. 1D. This extension product is then primed with a sequencing primer and subjected to sequencing processes as described herein and in Example 1, thereby providing temporal information for patients under short- or long-term drug treatment to provide relevant clinical information, for instance, gene signatures indicative of drug resistance that can be combined with additional histological and immunohistochemistry modalities to guide clinical decision-making.

The described methods within the Examples can be applied to single cells affixed to a transparent substrate, as well as to sections of tissue on a similar substrate. In both cases (individual cells or cells in tissue), the cells are fixed and permeabilized for delivering probes, enzymes, nucleotides and other components required for the reactions. The Examples recite RNA transcripts, however one having ordinary skill in the art would immediately understand that the methods are applicable to proteins using the methods described herein (e.g., associating an oligonucleotide primer with each of the plurality of targets by contacting each of the targets with a specific binding reagent, such as an antibody). Thus, the methods in the present Examples may be applied, mutatis mutandis, to detecting a plurality of different proteins of a cell in situ.

Example 12: Pharmacodynamic and Biomarker Analysis of a T Cell Immunomodulatory Molecule A wealth of information is reflected in the temporal and spatial variation of gene and protein expression among cells. Cellular macromolecules such as nucleic acids and proteins, occupy precise positions in cells and tissues, and a great deal of information is lost when these molecules are extracted. The methods available today for RNA sequence analysis (RNA-Seq) have the capacity to quantify the abundance of RNA molecules in a population of cells with great sensitivity. Current methods for single-cell RNA and protein analysis typically involve some method for "barcoding" the content of individual cells, followed by pooling the content and sequencing on a commercial DNA sequencing device (e.g., Illumina NextSee™ 500/550, MiSeq™, HiSeq™ 2500/3000/4000, or NovaSeq™). These methods have found wide application dissecting transcriptomic heterogeneity, and can handle upwards of 10,000 cells in an automated format, however they have several limitations and drawbacks. For example, if the cells of interest originate from a tissue sample, all information about the spatial distribution of the cells within the tissue is lost in the process of dissociating and isolating the cells prior to barcoding them. Often information about the intracellular distribution of analytes within the cellular microenvironment is also lost. This information can be vital to designing therapeutic approaches to cancers, for example, where the tumor microenvironment often creates spatial gradients of nutrients and metabolic byproducts.

In situ sequencing typically involves tissue and/or cellular extraction, combined with the fixation and permeabilization of cells, followed by amplification of the target nucleic acid fragments for sequencing. Briefly, cells and their surrounding milieu are attached to a substrate surface, fixed, and permeabilized. Targeted oligonucleotide probes designed for C-V-D-J sequencing are then annealed to complementary regions which flank the nucleic acid of interest or a portion thereof. As shown in FIG. 1B, the oligonucleotide probe hybridizes to regions which flank the target nucleic acid sequence or a portion thereof, referred to as the first and the second complementary regions. In the presence of a polymerase (e.g., a non-strand displacing polymerase), the complement to the target sequence is generated by extending from the first complementary region and is ligated (not shown) to the second complementary region to form a circularized oligonucleotide, as found in FIG. 1C. The resulting circularized oligonucleotide is primed with an amplification primer and extended with a strand-displacing polymerase to generate a concatemer containing multiple copies of the target nucleic acid sequence, as shown in FIG. 1D. This extension product is then primed with a sequencing primer and subjected to sequencing processes as described herein.

In embodiments, the methods described herein may be utilized for B cell heavy and light chain in situ sequencing by targeting the combination of variable and constant gene segments that make up a given heavy and light chain. These methods provide unique insight into the spatial localization and recombination efforts of a cell's heavy and light chain genes. Likewise, the methods can be applied for T-cell receptor (TCR) alpha and beta chain in situ sequencing. The genes encoding alpha (TCRA) and beta (TCRB) chains are composed of multiple non-contiguous gene segments which include V, D, and J segments for TCRB and V and J for TCRA. As with B cell receptor diversity, the enormous diversity of TCR repertoires is generated by random combinatorial gene events. The methods described here can be used to provide a comprehensive in situ view of TCR diversity in intact T cells.

Non-adherent cells may also serve as an important source of information for assessing the activity of candidate therapeutic agents. Immunomodulatory agents, for example, (alternatively referred to herein as cell modifying agents) have wide utility to the treatment of cancer, infectious and autoimmune disease, and may act upon adherent and non-adherent cell types. In the context of cancer immunotherapy, immunomodulatory agents may function by directly altering the activity of relevant immune cells (e.g., repression of immune suppressive cells or activation of anti-tumor cells), or indirectly eliciting immune cell responses by altering the immunogenicity of the cancer. For each modality there are numerous agents in active development or approved for clinical use. The number of potential treatment strategies is further increased by combinatorial immunotherapy strategies, where two or more agents are contemporaneously applied to enhance efficacy through complementary modes of action. Each immunomodulatory agent may give rise to one or more unique signatures that are detectable through the analysis of single cell gene expression, protein expression, and cell morphology. Here we describe methods for identifying agent-specific activity signatures. The methods have utility for the assessment of the pharmacodynamic activity of a therapeutic agent and as a means to identify predictive and prognostic biomarkers of response following a therapeutic intervention.

Figure 8:
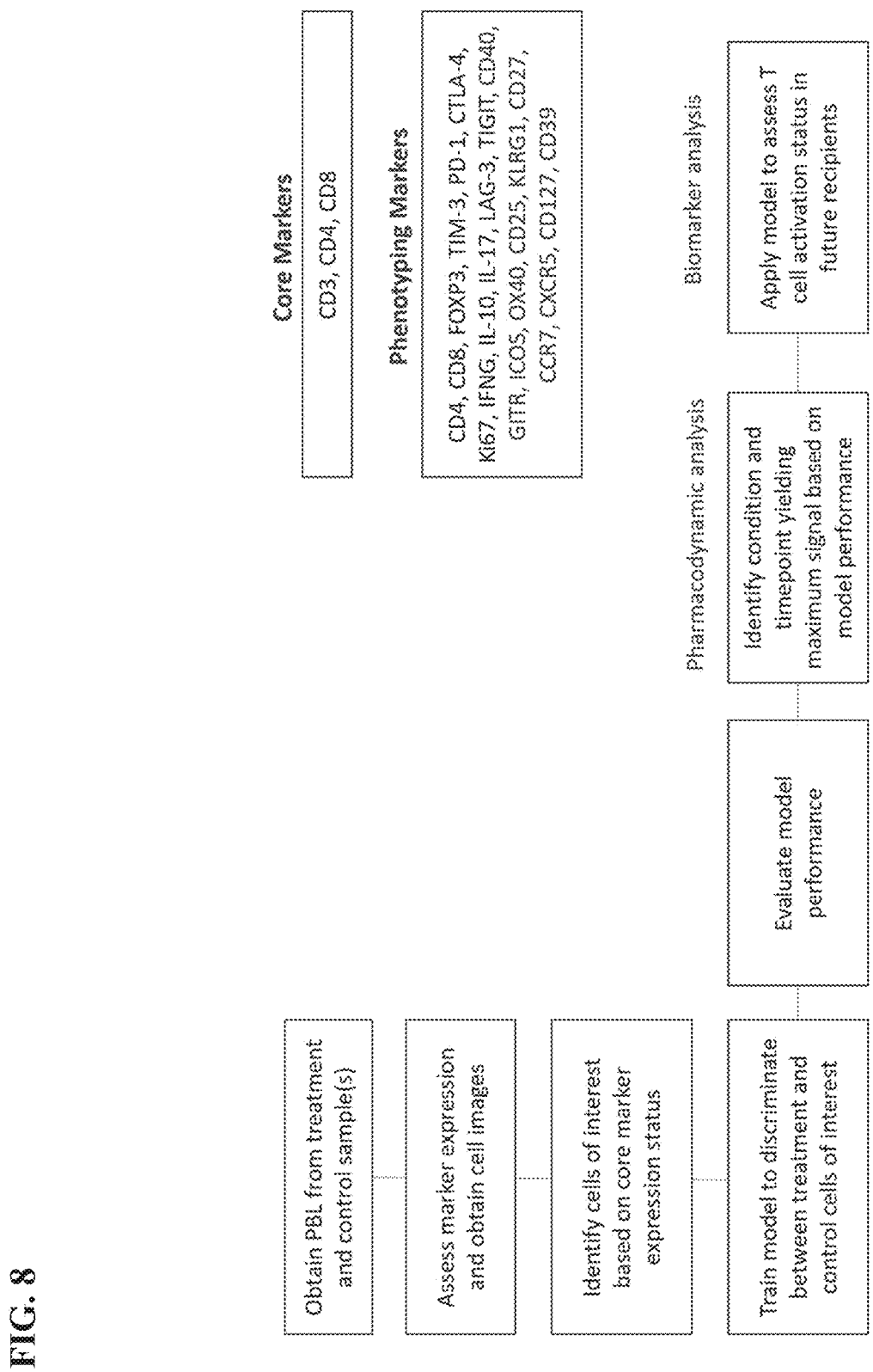
FIG. 8 provides an embodiment of a method for pharmacodynamic and biomarker analysis of a T cell modulating immunotherapy.

Checkpoint blockade immunotherapy may elicit durable anti-tumor responses that may be mediated in part by modulation of T cell activity. Methods to quantify the activity of a therapeutic agent are useful for understanding dose/exposure-response relationships and may reveal predictive and prognostic biomarkers of response (Agrawal, S., Feng, Y., Roy, A. et al. j. immunotherapy cancer 4, 72 (2016)). FIG. 8 provides an overview of a workflow using the methods as described herein to evaluate pharmacodynamics and identify biomarkers of response for a candidate T cell immunomodulating agent (e.g., a checkpoint blockade inhibitor) as part of a human dose escalation study (FIG. 8). Peripheral blood leukocytes are obtained from individuals receiving from 0.1-10 mg/kg of the agent over timepoints ranging from time of administration (day 0) to 30 days post administration. In parallel, peripheral blood leukocytes are obtained from matched controls. Cells are analyzed for expression of one or more marker genes (e.g., CD3, CD4, CD8, FOXP3, TIM-3, PD-1, CTLA-4, Ki67, IFNG, IL-10, IL-17, LAG-3, TIGIT, CD40, GITR, ICOS, OX40, CD25, KLRG1, CD27, CCR7, CXCR5, CD127, CD39) and cell images are acquired for analysis of cell morphology. In some embodiments, morphology analysis is performed in conjunction with application of cell staining or other contrast enhancing approaches known in the art (e.g., H&E staining, etc). Data from CD4 or CD8 positive T cells (cells expressing CD3 in combination with either CD4 or CD8; referred to herein as "core" markers) is retained for training of a model to discriminate treatment cells from control cells.

Following training, model performance is assessed using methods known in the art (e.g., cross-validation) to produce an area under the receiver-operator characteristic curve (AUC) summarizing the model performance for each dose and timepoint. An example of the results is presented in FIG. 9. Higher AUC values indicate the model can better discriminate treatment from control. AUC thus serves as a proxy for agent-mediated modulation of T cells. In FIG. 9, based on AUC analysis, a dose of 3 mg/kg or higher and a sampling timepoint of 10 days post administration appears to be the optimal combination for detecting an effect of the agent.

Figure 10:
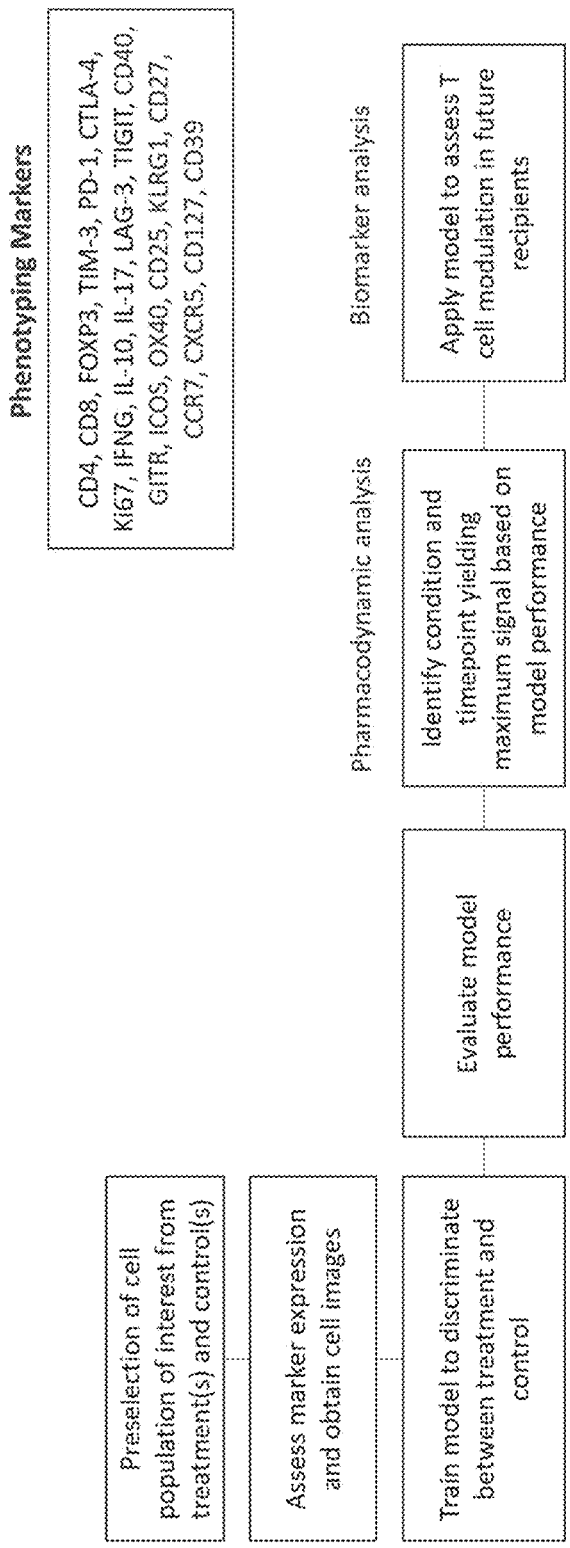
FIG. 10 provides an embodiment of a method for pharmacodynamic and biomarker analysis of a T cell modulating immunotherapy using presorted cells.

Following pharmacodynamic analysis, the model may be applied to evaluate response in individuals receiving the therapy. In a hypothetical example, a group of individuals receives the agent at 3 mg/kg. Peripheral blood lymphocytes (PBLs) are extracted at day 10 post-administration and analyzed via the methods described herein, then T cell modulation is quantified using the corresponding dose-timepoint model trained as part of pharmacodynamic analysis. The magnitude of T cell modulation is then correlated with clinical endpoints (e.g., progression free survival, objective response rate, etc.) to validate the predictive or prognostic utility of the metric. Finally, the validated metric is applied to predict outcomes for future recipients of the agent. FIG. 10 illustrates a variation of the above workflow where T cells of interest are preselected. Preselection eliminates the need to identify the relevant cell subpopulation by core marker analysis and minimizes analysis of irrelevant cell types.

Example 13: Measurable Residual Disease Monitoring of Acute Myeloid Leukemia

Measurable residual disease (MRD) is an important prognostic indicator with relevance to treatment planning and risk stratification for Acute Myeloid Leukemia (AML) (Wilson C S, Davidson G S, Martin S B, et al. Blood. 2006; 108(2):685-696; Bullinger et al. N Engl J Med 2004; 350: 1605-1616). Flow cytometric based detection of AML is an established method for detection and phenotyping of AML. The limit of detection for flow cytometry-based MRD assessment for AML is typically between 0.1-0.01% and is limited in part by the specificity of markers used for identification of the malignant cells (Peters J M, Ansari M Q. Multiparameter flow cytometry in the diagnosis and management of acute leukemia. Arch Pathol Lab Med. 2011 January; 135(1):44-54).

There is an urgent need for methods to assess residual disease for precision medicine. Technical challenges of residual disease detection include the need for a high sensitivity and specificity at a low limit of detection. Personalized cancer monitoring strategies aim to improve sensitivity and specificity by identifying and tracking patient-specific cancer mutations. Such methods require custom reagents, increasing testing complexity, cost, and turnaround time, ultimately reducing clinical utility. Herein we present methods for personalized cancer monitoring, for example, where the personalization is at the level of patient specific cancer cell image analysis morphology and is achieved through machine learning based image analysis. A patient specific neural network optimized to detect the patient's cancer obviates the need for custom reagents. The methods enable high sensitivity and specificity at a low limit of detection, while reducing the need for custom reagents. Utilizing the methods described herein, that is, combining cell morphology information with marker-based assessment, provides improved specificity of detection, thereby enabling a lower limit of detection.

Figure 7:
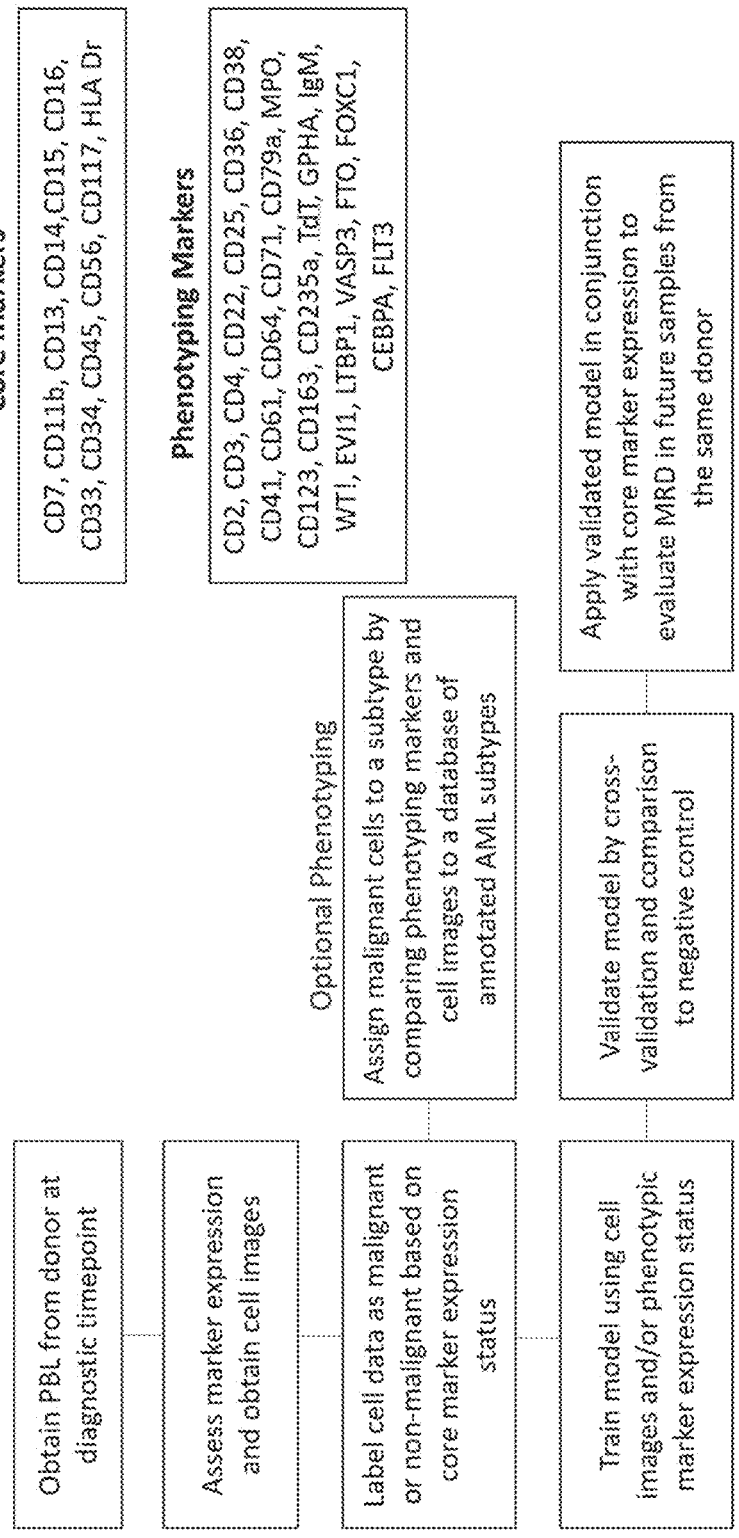
FIG. 7 provides an embodiment of a method for MRD assessment of AML using marker gene status and cell imaging.

A non-limiting example of a workflow for MRD monitoring of AML using the device described herein is presented in FIG. 7. The workflow begins by selection of a set of 'core' markers for identification of the malignant AML cells from a donor peripheral blood leukocyte (PBL) sample (FIG. 7). Relevant markers are known to those in the art and may include one or more of the following genes: CD7, CD11b, CD13, CD14, CD15, CD16, CD33, CD34, CD45, CD56, CD117, HLA Dr (Agrawal, S., Feng, Y., Roy, A. et al. j. immunotherapy cancer 4, 72 (2016)). Additional gene expression or mutation hotspot markers (e.g., determining the presence of one or more recurrent mutations from RNA/cDNA) may be included to aid in phenotyping of malignant cells. Phenotyping markers may include one or more of the following CD2, cCD3, CD4, cCD22, CD25, CD36, CD38, CD41, CD61, cCD61, CD64, CD71, cCD79a, cMPO, CD123, CD163, CD235a, TdT, GPHA, cIgM, WT1, EVI1, LTBP1, VASP3, FTO, FOXC1, CEBPA, FLT3, among others.

PBL cells from the donor are isolated, then analyzed using the methods described herein to determine the nucleic acid (e.g., RNA or cDNA) and/or protein expression of each selected marker (i.e., core and phenotyping markers), assess mutations, and obtain cell images for analysis of cell morphology. In some embodiments, morphology analysis is performed in conjunction with application of cell staining or other contrast enhancing approaches known in the art (e.g., H&E staining, etc). In some embodiments, more than about 1000 cells are analyzed in a single experiment. The expression status of the core markers is used to categorize each cell dataset as belonging to a malignant or non-malignant cell. Optionally, the set of identified malignant cells may be assigned to an AML subtype (e.g., AML-M0, AML-M1, AML-M2, etc.) by evaluating the status of the phenotyping markers and comparing malignant cell images to an image database of classified AML subtypes.

Next, labeled data is used to train a machine learning model to identify cell image features that distinguish malignant cells from non-malignant cells. Optionally, the model is trained using both the status of the phenotyping markers and the cell images. Training is performed using methods known in the art. Following training, model performance and validation is assessed using methods known in the art (e.g., cross-validation). This may include application of the model to additional labeled cell datasets, or applying the model to a control, such as a negative control dataset (e.g., data derived from the analysis of healthy donor PBL). Finally, the validated model is applied in conjunction with the analysis of the core marker set to determine the presence of malignant cells in future samples derived from the same donor.

Example 14: In Situ Sequencing with cDNA Intermediate

Figure 14:
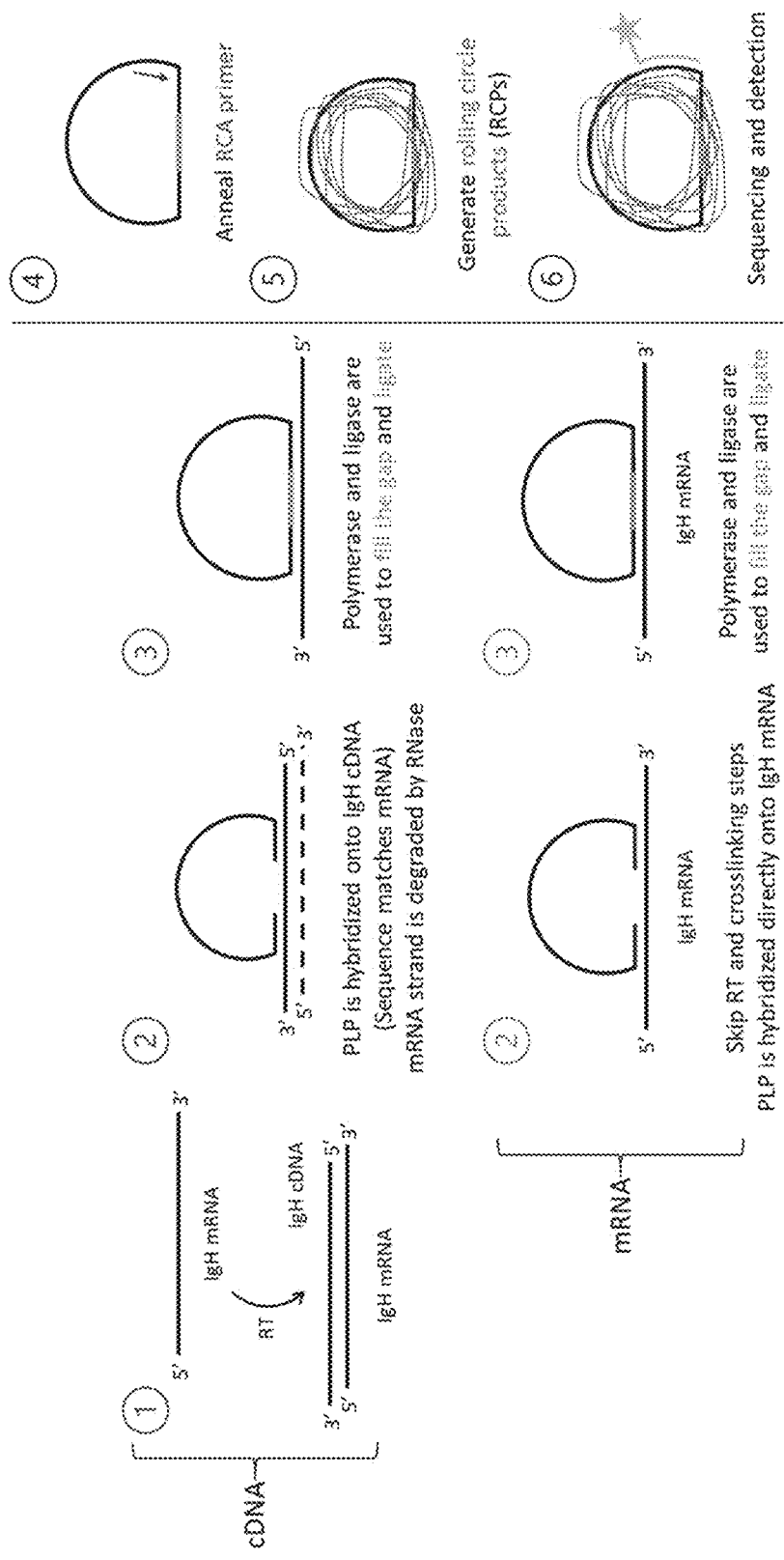
FIG. 14 is an illustration of the gap fill process using padlock probes targeting either cDNA or mRNA for in situ spatial sequencing in Ramos Burkitt's lymphoma cells. For cDNA (steps 1-3; top row), mRNA, for example, IgH mRNA is reverse transcribed to cDNA, followed by hybridization of a gapped padlock probe onto the cDNA and degradation of the mRNA strand by RNase. Subsequently, a polymerase extends the end of the padlock probe and fills the gap, copying the target sequence into the probe, and a ligase seals the gap. In contrast, when performing gap fill directly on mRNA (steps 2-3; bottom row), the reverse transcription and first crosslinking steps are skipped, and the padlock probe is directly hybridized onto the IgH mRNA. Following circularization of either cDNA or mRNA padlock probe, a rolling circle amplification (RCA) primer is annealed to the probe (step 4) and rolling circle amplification performed to generate rolling circle products (step 5). Finally, sequencing and detection is performed (step 6).

We proceeded to use the methods described herein to perform in situ spatial sequencing using gapped padlock probes targeted to a cDNA intermediate. The workflow that we followed for targeting a cDNA intermediate is illustrated in FIG. 14 (steps 1-3; top row). As illustrated, for example, IgH mRNA is reverse transcribed (using, e.g., SuperScript IV™ reverse transcriptase) to cDNA, followed by hybridization of a gapped padlock probe onto the cDNA and degradation of the mRNA strand by RNase. Subsequently, a polymerase (e.g., T4 DNA polymerase) extends the end of the padlock probe and fills the gap, copying the target sequence into the probe, and a ligase (e.g., T4 DNA ligase) seals the gap. Following circularization of either cDNA or mRNA padlock probe, a rolling circle amplification (RCA) primer is annealed to the probe (step 4) and rolling circle amplification performed to generate rolling circle products (step 5). Finally, sequencing and detection is performed using methods known in the art and described herein (step 6). Sequences for the first domain complementary to the first target sequence and second domain complementary to the second target sequence used in the padlock probes described herein were adapted from PCR primer sequences described in van Dongen J J M et al. Leukemia. 2003; 17: 2247-2317, which is incorporated herein by reference in its entirety.

Plating and Fixation: All steps were performed in 96-well plate format. Cell suspensions were centrifuged for 5 min at 0.3 rcf and resuspended in 1×PBS prior to plating. Cells were plated at a density of 100,000 live cells/well and allowed to settle at the bottom of the plate for at least 30 min at 4° C. Cells were then fixed with 4% formaldehyde in 1×PBS for 15 min at room temperature (RT), and washed 3 times with 1×PBS to remove the formaldehyde. Cells were then permeabilized with 0.5% Triton X-100 in 1×PBS for 20 min at RT, then washed 1× with 1×PBS and 2× with hybridization buffer (20% formamide and 2×SSC in water).

Reverse Transcription: To convert mRNA to cDNA, SuperScript IV™ reverse transcriptase (Thermo Fisher Catolog #18090010) was added at a final concentration of 10 U/uL with dNTPs (0.5 mM each), 0.125 mM aminoallyl-dUTP, 5 mM DTT, 0.2 ug/uL BSA, 1 uM reverse primer for the target gene, and 0.2 U/uL SUPERase-In™ RNase inhibitor (Thermo Fisher Catalog #AM2694) in 1× SuperScript IV™ buffer and incubated for 2 hrs at 37° C. Cells were then washed 3× with 1×PBS.

Crosslinking: BS(PEG)9 was then added at a final concentration of 5 mM in 1×PBS and incubated for 30 min at RT. Cells were then washed 1× with 1×PBS, and 1 M Tris (pH 8.0) added and incubated for 15 min at RT. Cells were then washed 1× with 1×PBS and 2× with hybridization buffer.

Hybridization, Gap Fill, and Probe Ligation: Padlock probes (PLPs) were added at a final concentration of 100 nM each with 10 mM ribonucleoside vanadyl complex (RVC) in hybridization buffer. PLPs were then allowed to hybridize overnight at 37° C. The cells were then washed 1× with hybridization buffer for 5 min at 37° C. and 2× with 1×PBS for 5 min each at 37° C. Following the washes, T4 DNA ligase (New England Biolabs Catalog #M0202S) was added at a final concentration of 24 U/uL and T4 DNA polymerase (New England Biolabs Catalog #M0203S) was added at a final concentration of 0.06 U/uL with dNTPs (0.125 mM each) and 10% PEG4000 in DEPC-treated water for 3 hrs at 37° C. to fill in the gap and circularize the probe. Cells were then washed 1× with 1×PBS and 2× with hybridization buffer.

Rolling Circle Amplification: Phosphorothioated amplification primer was added at a final concentration of 0.5 uM in hybridization buffer and incubated for 1 hr at 37° C. Cells were then washed 1× with hybridization buffer and 2× with 1×PBS. A mutant version of phi29 DNA polymerase was then added at a final concentration of 0.45 uM with 1 M betaine, dNTPs (0.5 mM each), 0.125 mM aminoallyl-dUTP, 0.2 mg/mL BSA, 4 mM DTT, and 0.2 U/uL SUPERase-In™ RNase inhibitor in DEPC-treated water and incubated for 1 hr at 37° C. Cells were then washed 3× with 1×PBS.

Crosslinking: BS(PEG)9 was then added at a final concentration of 5 mM in 1×PBS and incubated for 30 min at RT. Cells were then washed 1× with 1×PBS, and 1 M Tris (pH 8.0) added and incubated for 15 min at RT. Cells were then washed 3× with flow cell wash buffer (20 mM Tris, 0.025% Triton X-100, 0.1 mM EDTA, 100 mM NaCL, pH 8.04) and detection was performed.

Detection: TetraSpeck™ microspheres were added to crosslinked cells at a final concentration of 0.1 nM in PBST (0.1% Tween-20 in 1×PBS) and allowed to settle for at least 30 min at RT, or centrifuged for 3 min at 2,000 RPM. Sequencing primer was then added at a final concentration of 0.5 uM in hybridization buffer and incubated for 30 min at 37° C. The cells were then washed 3× with flow cell wash buffer, and sequencing-by-synthesis with detectable nucleotides was performed.

Figure 11:
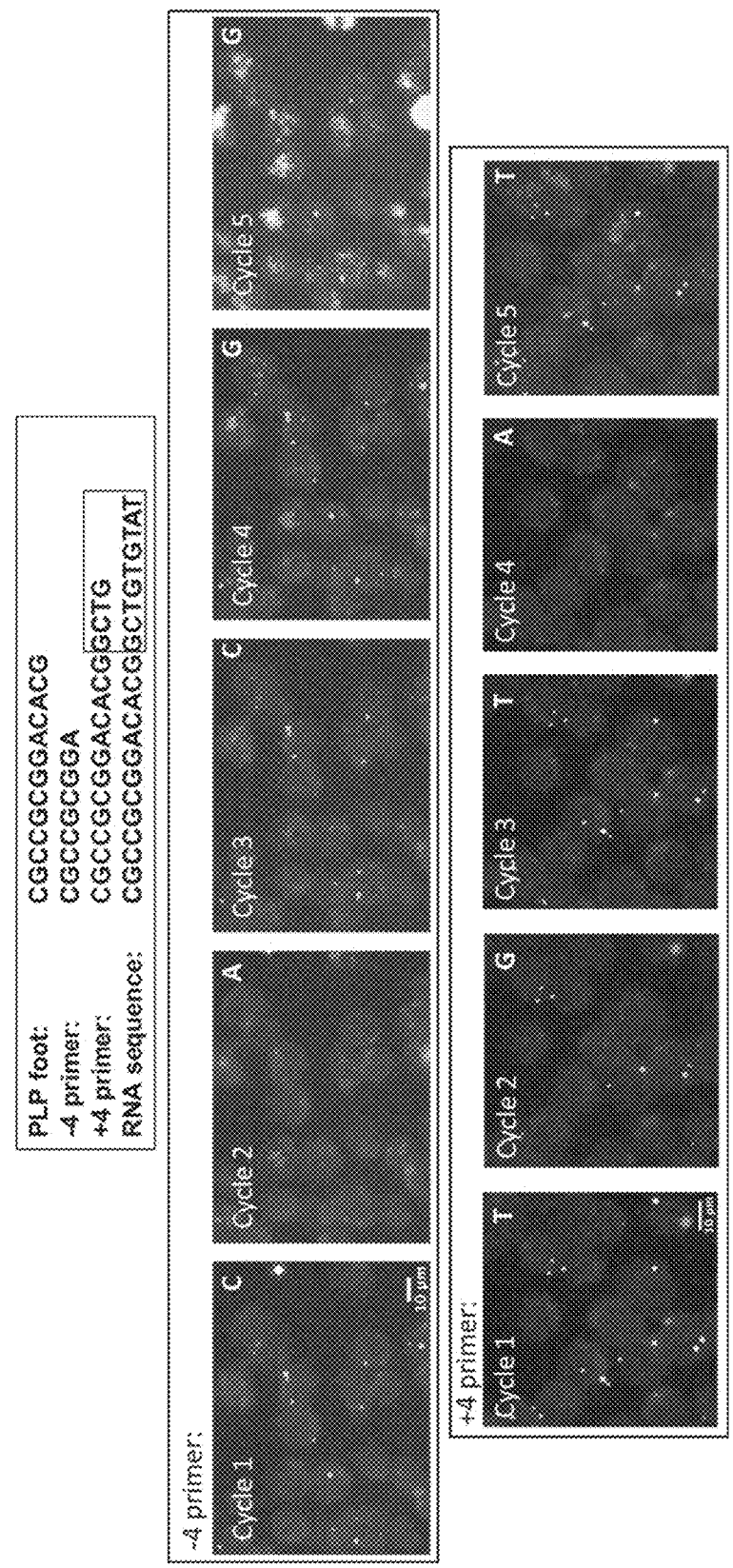
FIG. 11 presents a set of fluorescence microscopy images of in situ transcript sequencing through five sequencing cycles performed in one well of a 96-well plate, wherein a gapped padlock probe was targeted to a cDNA product of an IgH transcript in Ramos Burkitt's lymphoma cells. Each tile represents each of the first five sequencing cycles determined using a sequencing primer targeting 4 bases from the end of the padlock probe foot (−4 primer; top row), or a sequencing primer targeting 4 bases beyond the end of the padlock probe foot (+4 primer; bottom row). The sequences of the padlock probe (PLP) foot (SEQ ID NO: 1), −4 sequencing primer (SEQ ID NO: 2), +4 sequencing primer (SEQ ID NO: 3), and target RNA sequence (SEQ ID NO: 4) are annotated at the top of the figure. The portion of the +4 sequencing primer that corresponds to the gap-filled sequence is denoted by a small box.

Following the workflow outlined above, we performed in situ sequencing of an IgH transcript in Ramos Burkitt's lymphoma cells, as shown in FIG. 11. Five sequencing cycles were performed in one well of a 96-well plate, wherein the gapped padlock probe was targeted to a cDNA product of an IgH transcript. Each tile of FIG. 11 represents each of the first five sequencing cycles using a sequencing primer targeting 4 bases from the end of the padlock probe first hybridization domain (also known as "foot" or "pad") (−4 primer; top row), or a sequencing primer targeting 4 bases beyond the end of the padlock probe first hybridization domain (+4 primer; bottom row). The sequences of the padlock probe foot, +4 sequencing primer, −4 sequencing primer, and the resulting RNA sequence (as cDNA) are shown at the top of FIG. 11, with the target sequence that was filled in the gap highlighted by a small box. By changing the sequence of the sequencing primer (i.e., the sequence that the sequencing primer hybridizes to) we can shift what is readout within the same cell line and padlock probe. In this example, we used two sequencing primers on two samples of the same cell line and padlock probe. The first sequencing primer (−4 sequencing primer) was recessed 4 bases from the end of the padlock probe foot, such that the first 4 bases readout are confirmed by the padlock probe itself, and the 5th base is in the gap (see FIG. 11). Sequencing any portion of the padlock probe foot itself can be included as a quality control step for sequencing analysis. The second primer used (+4 sequencing primer) is located 4 bases into the gap beyond the foot of the PLP (see FIG. 11, bottom row), such that all bases readout were incorporated into the circular template during the gap fill process. The sequencing primer may be customized to suit individual sequencing needs, for example, to target the end of the padlock probe foot, or to target a −1 or −2 position with respect to the end of the padlock probe foot.

Figure 12:
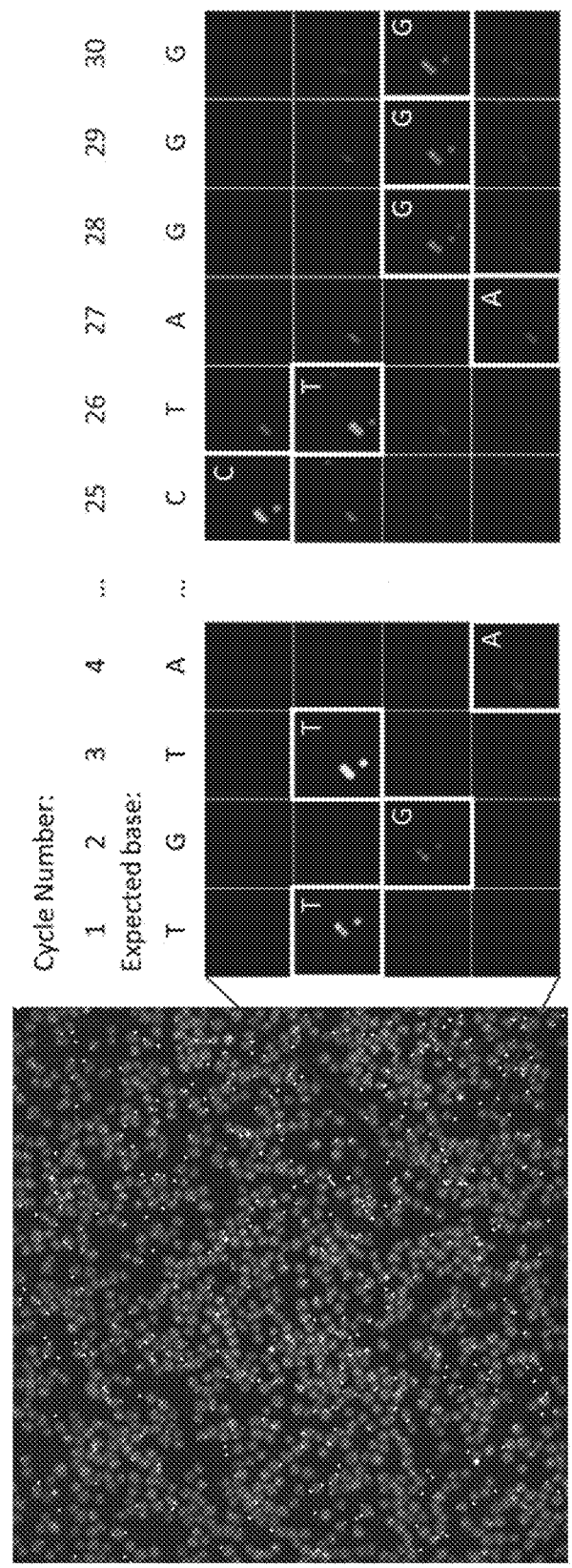
FIG. 12 is a set of fluorescence microscopy images of in situ transcript sequencing through 30 sequencing cycles performed in one well of a 96-well plate in Ramos Burkitt's lymphoma cells. As shown in the bottom row of FIG. 11, the sequencing primer used was targeted 4 bases beyond the foot of the PLP, such that all 30 bases sequenced were incorporated into the padlock probe during the gap fill extension step. The full 30-base target sequence is (SEQ ID NO: 5)
TGTATTACTGTGCGAGAGTTATTACTAGGG.

Next, we expanded upon the results described in FIG. 11 by performing in situ transcript sequencing through 30 sequencing cycles performed in one well of a 96-well plate. As shown in FIG. 12, the sequencing primer used was targeted 4 bases beyond the foot of the padlock probe, such that all 30 bases sequenced were incorporated into the padlock probe during the gap fill extension step. The highlighted tiles shown in FIG. 12 indicate the base detected during each sequencing cycle in the outlined cell. This example demonstrates the ability to perform at least 30 in situ sequencing cycles in a single-cell. We estimate that each well of a 96-well plate (as shown in FIG. 12) can hold approximately 55,000 cells, so these methods could be applied to sequencing about 5.3 million cells in a single 96-well plate, which can be automated for high-throughput processing.

Figure 13:
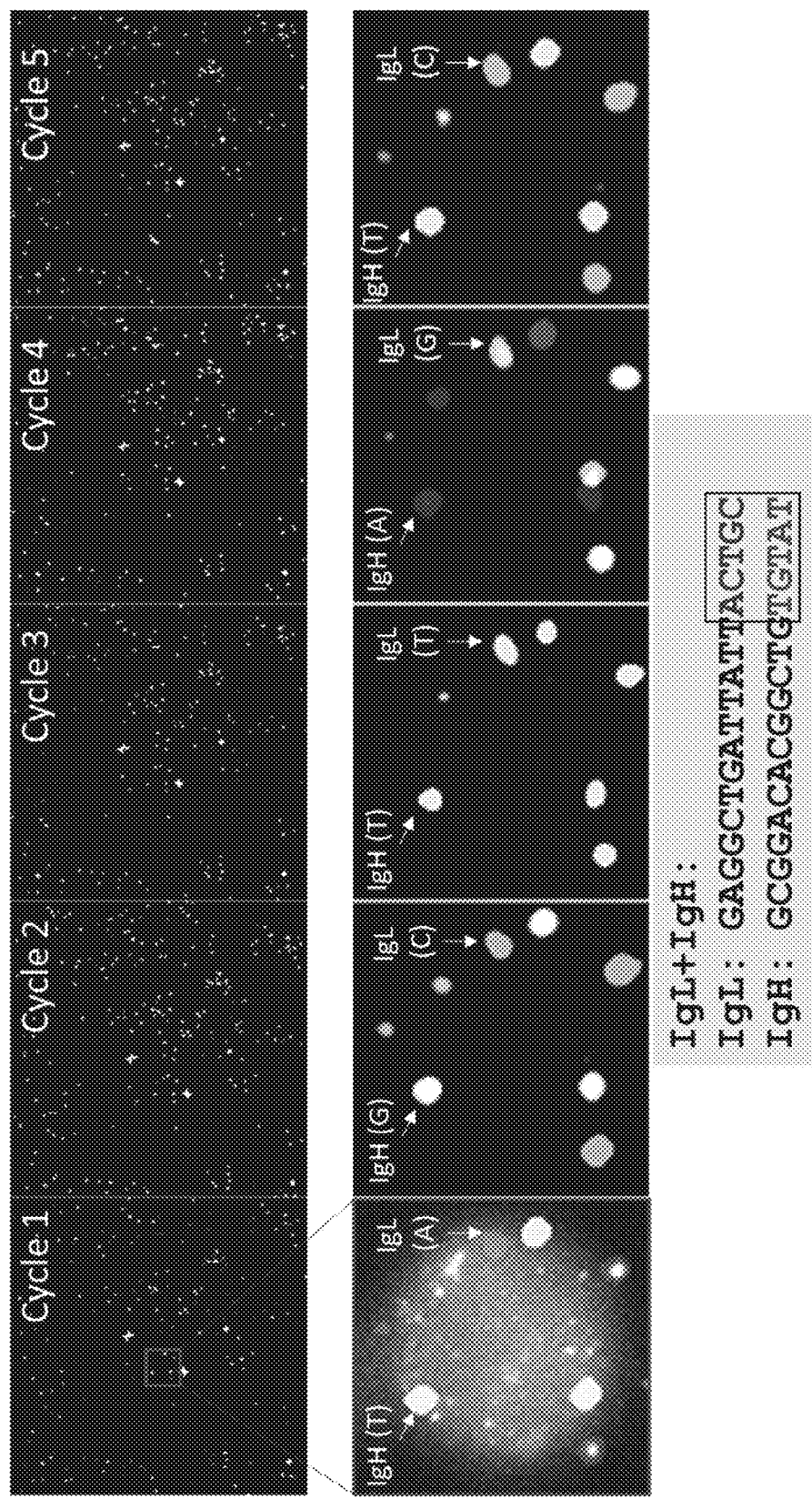
FIG. 13 is a set of fluorescence microscopy images of in situ transcript sequencing through 5 sequencing cycles demonstrating multiplexed sequencing in Ramos Burkitt's lymphoma cells. Gapped padlock probes were targeted to incorporate the CDR3 region of IgL and IgH in B cells. At the bottom is the sequence of the primers for IgL (SEQ ID NO: 6) and IgH (SEQ ID NO: 7) followed by the sequence that is being read out in each cycle (enclosed by the box). The bottom left panel shows the first cycle of sequencing for a single B cell overlaid on a cell body stain. In the subsequent panels only the sequencing results are shown. Following any dot across the 5 cycles results in the sequence associated with the CDR3 region of IgL or IgH targeted. The top row demonstrates a larger field of view from where the bottom row was obtained, as indicated in the first panel. The sequencing primer target sequence for each of the IgL and IgH padlock probes is located in the gap, thus all 5 bases sequenced represent the sequence incorporated into the padlock probe during gap fill. These padlock probes are targeted to the cDNA, so the sequence retrieved is exactly that of the mRNA transcript.

We proceeded to demonstrate that we can use these methods to perform multiplexed in situ sequencing. As shown in FIG. 13, using the methods described herein with gapped padlock probes targeted to incorporate the CDR3 region of IgL and IgH in Ramos B cells, we performed multiplexed sequencing across five sequencing cycles. At the bottom of FIG. 13 are the annotated sequences of each primer followed by the sequence that is being read out in each cycle (enclosed by the box). The bottom left panel shows the first cycle of sequencing for a single B cell overlaid on a cell body stain. In the subsequent panels only the sequencing results are shown. Following any dot across the five cycles results in the sequence associated with the CDR3 region of IgL or IgH. The top row demonstrates a larger field of view from where the bottom row was obtained, as indicated in the first panel. The sequence for each of the IgL and IgH padlock probe sequencing primers are located in the gap, thus all 5 bases represent the sequence incorporated into the padlock probe during the gap fill extension. These padlock probes are targeted to the cDNA, so the sequence retrieved is exactly that of the mRNA transcript.

Example 15: Direct In Situ Sequencing of mRNA Transcripts

We proceeded to use the methods described herein to perform in situ spatial sequencing using gapped padlock probes targeting mRNA transcripts directly. The workflow that we followed for targeting mRNA is illustrated in FIG. 14 (steps 2-3; bottom row). As illustrated, for example, a gapped padlock probe is directly hybridized onto the IgH mRNA. Subsequently, a polymerase (e.g., Tth DNA polymerase) extends the end of the padlock probe and fills the gap, copying the target sequence into the probe, and a ligase (e.g., SplintR ligase) seals the gap. Following circularization of either cDNA or mRNA padlock probe, a rolling circle amplification (RCA) primer is annealed to the probe (step 4) and rolling circle amplification performed to generate rolling circle products (step 5). Finally, sequencing and detection is performed using methods known in the art and described herein (step 6).

Plating and Fixation: All steps were performed in 96-well plate format. Cell suspensions were centrifuged for 5 min at 0.3 rcf and resuspended in 1×PBS prior to plating. Cells were plated at a density of 100,000 live cells/well and allowed to settle at the bottom of the plate for at least 30 min at 4° C. Cells were then fixed with 4% formaldehyde in 1×PBS for 15 min at room temperature (RT), and washed 3 times with 1×PBS to remove the formaldehyde. Cells were then permeabilized with 0.5% Triton X-100 in 1×PBS for 20 min at RT, then washed 1× with 1×PBS and 2× with hybridization buffer (20% formamide and 2×SSC in water).

Hybridization, Gap Fill, and Probe Ligation: Padlock probes (PLPs) were added at a final concentration of 100 nM each with 10 mM ribonucleoside vanadyl complex (RVC) in hybridization buffer. PLPs were then allowed to hybridize overnight at 37° C. The cells were then washed 1× with hybridization buffer for 5 min at 37° C. and 2× with 1×PBS for 5 min each at 37° C. Following the washes, Tth DNA polymerase was added at a final concentration of 0.125 U/uL with dNTPs (0.3 mM each) and 2.5 mM Mn(OAc)$_2$ in 1×RT-PCR buffer and incubated for 1 hr at 60° C. to fill in the gap. The cells were then washes 3× in 1×PBS. Following the washes, SplintR® ligase (New England Biolabs Catalog #M0375S) was added at a final concentration of 2.5 U/uL with 0.2 U/uL SUPERase-In™ RNase inhibitor (Thermo Fisher Catalog #AM2694) in 1× SplintR ligase buffer and incubated for 30-60 min at 37° C. Cells were then washed 1× with 1×PBS and 2× with hybridization buffer.

Rolling Circle Amplification: Phosphorothioated amplification primer was added at a final concentration of 0.5 uM in hybridization buffer and incubated for 1 hr at 37° C. Cells were then washed 1× with hybridization buffer and 2× with 1×PBS. A mutant version of phi29 DNA polymerase was then added at a final concentration of 0.45 uM with 1 M betaine, dNTPs (0.5 mM each), 0.125 mM aminoallyl-dUTP, 0.2 mg/mL BSA, 4 mM DTT, and 0.2 U/uL SUPERase-In™ RNase inhibitor in DEPC-treated water and incubated for 1 hr at 37° C. Cells were then washed 3× with 1×PBS.

Crosslinking: BS(PEG)9 was then added at a final concentration of 5 mM in 1×PBS and incubated for 30 min at RT. Cells were then washed 1× with 1×PBS, and 1 M Tris (pH 8.0) added and incubated for 15 min at RT. Cells were then washed 3× with flow cell wash buffer (20 mM Tris, 0.025% Triton X-100, 0.1 mM EDTA, 100 mM NaCL, pH 8.04) and detection was performed.

Detection: TetraSpeck™ microspheres were added to crosslinked cells at a final concentration of 0.1 nM in PBST (0.1% Tween-20 in 1×PBS) and allowed to settle for at least 30 min at RT, or centrifuged for 3 min at 2,000 RPM. Sequencing primer was then added at a final concentration of 0.5 uM in hybridization buffer and incubated for 30 min at 37° C. The cells were then washed 3× with flow cell wash buffer, and sequencing-by-synthesis with detectable nucleotides was performed.

Figure 15:
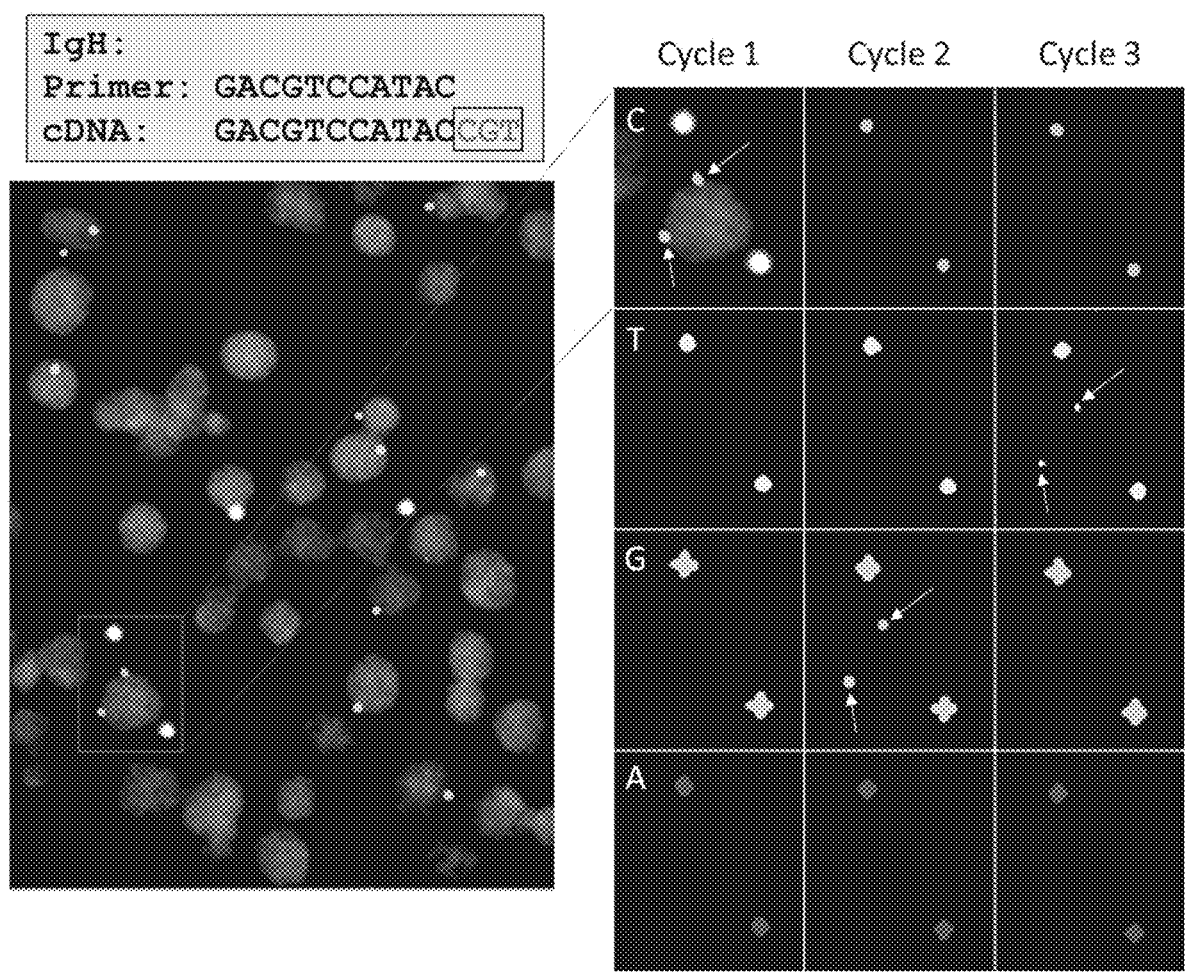
FIG. 15 is a set of fluorescence microscopy images using a gapped padlock probe targeting mRNA transcripts directly for in situ spatial sequencing without a cDNA intermediate in Ramos Burkitt's lymphoma cells. Panels for each of the first 3 sequencing cycles are shown for each of the 4 detectable bases. A sequencing primer for IgH (SEQ ID NO: 8) that targets 4 bases beyond the end of the padlock probe foot was used, therefore all of the bases sequenced are those that were incorporated into the padlock probe during the gap fill extension step. In this example, the sequence read out is the reverse complement of the mRNA sequence (as there is no cDNA intermediary), so the detected sequence is compared to the "cDNA" sequence that would be present if a cDNA step had occurred (highlighted by small box). The white dots in the left panel and the bigger dots in the right panels are focusing beads. The top left sub-panel of the right panel shows the overlay on a cell body stain. Arrows indicate the location of the detected signal in each sequencing cycle.

Here we describe the results of targeting a gapped padlock probe directly to mRNA transcripts of IgH (rather than with a cDNA intermediary) as outlined in FIG. 14. FIG. 15 is a set of fluorescence microscopy images using a gapped padlock probe targeting mRNA transcripts directly for in situ spatial sequencing without a cDNA intermediate in Ramos Burkitt's lymphoma cells. Panels for each of the first three sequencing cycles are shown for each of the 4 detectable bases. A sequencing primer that targets 4 bases beyond the end of the padlock probe foot was used, therefore all of the bases sequenced are those that were incorporated into the padlock probe during the gap fill extension step. In this example, the sequence read out is the reverse complement of the mRNA sequence (as there is no cDNA intermediary), so the detected sequence is compared to the "cDNA" sequence that would be present if a cDNA step had occurred (highlighted by small box). The white dots in the left panel and the bigger dots in the right panels are focusing beads. The top left sub-panel of the right panel shows the overlay on a cell body stain. Arrows indicate the location of the detected signal in each sequencing cycle. This data demonstrates that we can incorporate a de novo sequence into a padlock probe without a cDNA molecule intermediary.

What is claimed is:

1. A method of sequencing a plurality of target RNA molecules of a cell in situ, said method comprising:
   i) hybridizing an oligonucleotide primer consisting of DNA to each of the plurality of target RNA molecules in a cell, wherein the oligonucleotide primer comprises a first region at a 3' end that hybridizes to a first complementary region of the RNA molecule, and a second region at a 5' end that hybridizes to a second complementary region of the RNA molecule, wherein the second complementary region is about 10 to about 150 nucleotides in the 5' direction with respect to the first complementary region;
   ii) extending the 3' end of the oligonucleotide primer along the RNA molecule to generate a complementary sequence, wherein extending consists of incorporating deoxyribonucleotides into the 3' end of the oligonucleotide primer, and ligating the complementary sequence to the 5' end of the oligonucleotide primer thereby forming a circular oligonucleotide consisting of DNA;
   iii) amplifying the circular oligonucleotide by extending an amplification primer hybridized to the circular oligonucleotide with a strand-displacing polymerase, wherein the amplification primer extension generates an extension product comprising multiple complements of the circular oligonucleotide; and
   iv) sequencing the extension product of step (iii) in the cell, wherein sequencing comprises sequencing by synthesis.

2. The method of claim 1, wherein the cell is a bacterial cell, a fungal cell, a plant cell, a mammalian cell, a stem cell, an immune cell, a cancer cell, a viral-host cell, or a cell that selectively binds to a desired target.

3. The method of claim 2, wherein the cell is a bacterial cell, a fungal cell, or a viral-host cell comprising a viral nucleic acid sequence, wherein the bacterial cell is a *Bacteroides, Clostridium, Faecalibacterium, Eubacterium, Ruminococcus, Peptococcus, Peptostreptococcus, Bifidobacterium, Enterococcus faecalis, Escherichia coli, Enterobacter* sp., *Klebsiella* sp., *Staphylococcus aureus, Lactobacillus, Proteus mirabilis, Pseudomonas aeruginosa, Salmonella enterica,* or *Peptostreptococcus* sp. cell, wherein the fungal cell is a *Candida, Saccharomyces, Aspergillus, Penicillium, Rhodotorula, Trametes, Pleospora, Sclerotinia, Bullera,* or a *Galactomyces* cell, and optionally wherein the viral nucleic acid sequence is from a Hepadnaviridae, Adenoviridae, Herpesviridae, Poxviridae, Parvoviridae, Reoviridae, Coronaviridae, or a Retroviridae virus.

4. The method of claim 1, wherein the plurality of target RNA molecules comprise variable regions and constant regions of a nucleic acid molecule.

5. The method of claim 4, wherein the variable regions and constant regions comprise regions of a VDJ recombination of a B cell or T cell.

6. The method of claim 1, wherein the cell is a neuronal cell, an endothelial cell, epithelial cell, germ cell, plasma cell, a muscle cell, peripheral blood mononuclear cell (PBMC), a myocardial cell, cancer cell, or a retina cell.

7. The method of claim 1, wherein the cell is permeabilized and immobilized to a solid support surface.

8. The method of claim 7, wherein the surface comprises a patterned surface suitable for immobilization of a plurality of cells in an ordered pattern.

9. The method of claim 1, wherein the oligonucleotide primer is about 50 to about 500 nucleotides in length.

10. The method of claim 1, wherein the oligonucleotide primer is a single-stranded polynucleotide comprising at least one amplification primer binding sequence, at least one sequencing primer binding sequence, or both one amplification primer binding sequence and one sequencing primer binding sequence.

11. The method of claim 1, wherein the circular oligonucleotide is about 100 to about 1000 nucleotides in length, about 100 to about 300 nucleotides in length, about 300 to about 500 nucleotides in length, or about 500 to about 1000 nucleotides in length.

12. The method of claim 1, wherein the first complementary region of the oligonucleotide primer or the second complementary region of the oligonucleotide primer comprises about 5 to about 15 nucleotides.

13. The method of claim 1, wherein amplifying comprises rolling circle amplification (RCA) or rolling circle transcription (RCT).

14. The method of claim 1, wherein the extension product comprises three or more copies of the circular oligonucleotide.

15. The method of claim 1, wherein sequencing comprises extending one or more sequencing primers hybridized to the extension product.

16. The method of claim 1, wherein sequencing comprises extending a sequencing primer by incorporating a labeled nucleotide, or labeled nucleotide analogue and detecting the label to generate a signal for each incorporated nucleotide or nucleotide analogue, wherein the sequencing primer is hybridized to the extension product.

17. The method of claim 16, wherein detecting comprises two-dimensional (2D) or three-dimensional (3D) fluorescent microscopy.

18. The method of claim 16, wherein detecting comprises confocal microscopy, light sheet microscopy, or multi-photon microscopy.

19. A method of sequencing an agent-mediated nucleic acid sequence of a cell, said method comprising administering a genetically modifying agent to the cell, and sequencing an agent-mediated nucleic acid sequence of the cell in situ according to claim 1.

20. A method of identifying a nucleic acid sequence as an agent-mediated nucleic acid sequence, said method comprising administering a genetically modifying agent to a cell, detecting whether an agent-mediated nucleic acid sequence is present in the cell by sequencing a plurality of target nucleic acids according to claim 1, and identifying the nucleic acid sequence as an agent-mediated nucleic acid sequence when the presence of the agent-mediated nucleic acid is detected in the cell.

21. A method of identifying a cell that responds to a genetically modifying agent, said method comprising administering a genetically modifying agent to the cell, detecting whether an agent-mediated nucleic acid sequence is present in the cell by sequencing a plurality of target nucleic acids according to claim 1, and identifying a cell that responds to a genetically modifying agent when the presence of the agent-mediated nucleic acid is detected in the cell.

22. A method of identifying an agent as a genetically modifying agent, said method comprising administering an agent to a cell, detecting whether an agent-mediated nucleic acid sequence is present in the cell by sequencing a plurality of target nucleic acids according to claim 1, and identifying the agent as a genetically modifying agent when the presence of the agent-mediated nucleic acid is detected in the cell.

23. The method of claim 1, wherein the extending of step ii) is performed with a M-MLV reverse transcriptase, or a *Thermus thermophilus* (Tth) DNA polymerase or mutant thereof.

24. The method of claim 1, wherein the first complementary region and the second complementary region are about 10 to about 50 nucleotides apart.

25. The method of claim 1, wherein all steps are performed in one or more wells of a multiwell container.

26. The method of claim 1, wherein two or more oligonucleotide primers hybridize to different complementary regions of the same RNA molecule.

27. The method of claim 1, further comprising identifying a protein in the cell, wherein detecting the protein comprises contacting the cell with a specific binding reagent and detecting said specific binding reagent, thereby identifying the protein in the cell.

28. The method of claim 1, wherein amplifying the circular oligonucleotide comprises extending the amplification primer hybridized to the circular oligonucleotide with a strand-displacing polymerase and one or more modified nucleotides comprising a bioconjugate reactive group, wherein the amplification primer extension generates an extension product comprising one or more modified nucleotides comprising a bioconjugate reactive group.

* * * * *